(12) United States Patent
Zask et al.

(10) Patent No.: US 7,390,910 B2
(45) Date of Patent: Jun. 24, 2008

(54) COMPOUNDS FOR TREATING TUMORS

(75) Inventors: Arie Zask, New York, NY (US); Joshua Kaplan, Nyack, NY (US); Ayako Yamashita, Englewood, NJ (US); Chuan S. Niu, Cheshire, CT (US); Gary Harold Birnberg, Tuxedo Park, NY (US); Emily Norton, Nanuet, NY (US); Kinwang Cheung, Harrington Park, NJ (US); Ronald Suayan, Waldwick, NJ (US); Vincent Sandanayaka, Northboro, MA (US); Philip Ross Hamann, Thiells, NY (US); Semiramis Ayral-Kaloustian, Tarrytown, NY (US)

(73) Assignee: Wyeth, Madison, NJ (US)

( * ) Notice: Subject to any disclaimer, the term of this patent is extended or adjusted under 35 U.S.C. 154(b) by 233 days.

(21) Appl. No.: 10/911,300

(22) Filed: Aug. 4, 2004

(65) Prior Publication Data
US 2005/0037977 A1 Feb. 17, 2005

Related U.S. Application Data

(60) Provisional application No. 60/493,841, filed on Aug. 8, 2003.

(51) Int. Cl.
*C07D 207/04* (2006.01)
*A61K 31/40* (2006.01)

(52) U.S. Cl. .................. 548/532; 548/533; 514/423

(58) Field of Classification Search ............. 548/532, 548/533; 514/423
See application file for complete search history.

(56) References Cited

U.S. PATENT DOCUMENTS

2005/0239870 A1* 10/2005 Kowalczyk et al. ......... 514/423

FOREIGN PATENT DOCUMENTS

| WO | WO 99/32509 | 7/1999 |
|---|---|---|
| WO | WO 03/072754 A2 | 9/2003 |
| WO | WO 03/082268 A2 | 10/2003 |
| WO | WO 2004/026293 A2 | 4/2004 |

OTHER PUBLICATIONS

Zask, A.; et al.; D-Piece Modifications of the Hemiasterlin Analog HTI-286 Produce Potent Tubulin Inhibitors; Bioorganic and Medicinal Chemistry Letters, 14:4353-4358, 2004.

* cited by examiner

*Primary Examiner*—Shailendra Kumar
(74) *Attorney, Agent, or Firm*—Stephen E. Johnson

(57) ABSTRACT

The invention provides compounds of formula (I):

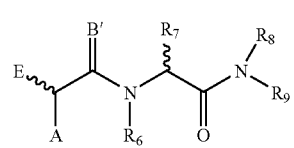

wherein E, A, B', $R_6$, $R_7$, $R_8$, and $R_9$ are defined in the specification which compounds exhibit anticancer activity and are useful for treating cancer.

45 Claims, No Drawings

COMPOUNDS FOR TREATING TUMORS

This application claims priority from copending provisional application Ser. No. 60/493,841, filed Aug. 8, 2003, the entire disclosure of which is hereby incorporated by reference.

FIELD OF THE INVENTION

The present invention relates to new hemiasterlin derivatives and salts thereof which demonstrate anti-mitotic and cytotoxic activity and are useful for treating cancer. The present invention further relates to a method of treating or inhibiting the growth of cancerous tumour cells and associated diseases in a mammal and additionally relates to pharmaceutical compositions containing compounds of the invention and salts thereof, and novel processes for preparing compounds of the invention and salts thereof.

BACKGROUND OF THE INVENTION

Drug resistance is a major impediment in cancer chemotherapy. Patients may acquire resistance during multiple cycles of therapy. Alternatively, patients may not respond at the onset of therapy (inherent resistance). Resistance to virtually all approved cancer cytotoxic chemotherapy has been reported including antimitic agents (paclitaxel and docetaxel, vinblastine, vincristine or vinorelbine), topoisomerase inhibitors (etoposide, teniposide, topotecan, camptothecin, doxorubicin and duanorubicin), antimetabolities (methotrexate, 5-flurouracil, gemcitabine), alkylating agents (melphalan, chlorambucil), and other DNA damaging agents (cisplatin and its analogs). (Goldstein, L. J., Ozols, R. F. Anticancer Drug Resistance, p. 294. Boston: Kluwer Academic Publishers, 1994.) The mechanisms mediating resistance are highly diverse. Finding and developing chemical compounds having novel structures for use in tumor therapy and which overcome resistance is important.

Hemiasterlins are natural products derived from sponges that induce microtubule depolymerization, $G_2$/M cell cycle arrest, and ultimately cell death.

Finding and developing chemical compounds having novel structures for use in tumor therapy and which overcome resistance is important. (Anderson, H. J., Coleman, J. E., Andersen, R. J., Roberge, M. Cytotoxic peptides hemiasterlin, hemiasterlin A and hemiasterlin B induce mitotic arrest and abnormal spindle formation, Cancer Chemother. Pharmacol. 39: 223-226, 1997. Talpir, R., Benayahu, Y., Kashman, Y., Pannell, L., Schleyer, M. Hemiasterlin and geodiamolide TA: two new cytotoxic peptides from the marine sponge hemiasterellaminor (kirkpatrick), Tetrahedron Letters 35: 4453-4456, 1994). Hemiasterlins in cancer therapy have been reported (WO 99/32509, WO 96/33211 and U.S. Pat. No. 6,153,590). Further, Hemiasterlin may be obtained from marine sponges (U.S. Pat. No. 5,661,175 (1997) and U.S. Pat. No. 6,153,590 (2000)) or synthesized (Andersen, R. J., Coleman, J. E. Tetrahedron Letters 38: 317-320, 1997). Synthetic analogs of hemiasterlin have also been prepared (WO 99/32509), and Hemiasterlin and the synthetic analogs thereof are reported to have cytotoxic and anti-mitotic activities.

The mechanisms that may mediate resistance to known antimitotic agents include drug efflux pumps (MDR1 and possibly MXR), tubulin mutations, alternative isotypes expression of tubulin isomers, alteration in the expression or function of genes that mediate apoptosis (e.g. p53 and bcl-2), and overexpression of growth factors such as HER-2. (Rowinsky, E. K., Tolcher, A. W. Antimicrotubule agents. In: J. Devita, V. T., Hellman, S., Rosenberg, S. A. (ed.) Cancer Principles and Practice, 6th edition edition, pp. 431-452. Philadelphia: Lippincott Williams and Wilkins, 2001) Resistance mediated by the multidrug drug resistance gene, MDR-1, has been intensively studied, mainly because it is frequently encountered in experimental models. (Greenberger, L. M., Cohen, D., and Horwitz, S. B. In vitro models of multiple drug resistance. In: a. R. F. O. L. J. Goldstein (ed.) Anticancer Drug Resistance, pp. 69-106. Norwell, Mass.: Kluwer Academic Publishers, 1994) MDR-1 is implicated in resistance to anti-microtubule agents since: 1) selection of tissue culture cells for resistance to vinca alkaloids or taxanes leads to marked overexpression of MDR-1, 2) cells that overexpress MDR-1 have low drug accumulation of taxanes or vinca alkaloids, 3) transfection of cells with MDR-1 induces resistance to these agents, 4) photoaffinity probes for vinca alkaloids or taxanes bind to the MDR-1 gene product, P-glycoprotein, 5) transgenic mice devoid of MDR gene family members have altered pharmacokinetic profiles for taxanes and 5) agents that inhibit P-glycoprotein resensitize resistant cells to taxanes or vinca alkaloids. The clinical relevance of MDR-1 overexpression is not clear in most solid tumor types and its association with lack of patient response or poor prognosis is controversial. (Bradshaw, D. M., Arceci, R. J. Clinical relevance of transmembrane drug efflux as a mechanism of multidrug resistance, J. Clin. Oncol. 16: 3674-3690, 1998) Nevertheless, overexpression of MDR1 has been clearly associated with response to chemotherapy and prognosis in leukemias. Low level resistance to vinca alkaloids (but not taxanes) has also been found in cells transfected with another efflux pump, MRP. (Breuninger, L. M., Paul, S., Gaughan, K., Miki, T., Chan, A., Aaronson, S. A., Kruh, G. D. Expression of multidrug resistance-associated protein in NIH/3T3 cells confers multidrug resistance associated with increased drug efflux and altered intracellular drug distribution., Cancer Res. 55: 5342-5347, 1995; Zaman, G. J. R., Flens, M. J., van Leusden, M. R., de Haas, M., Mulder, H. S., Lankelma, J., Pinedo, H. M., Scheper, R. J., Baas, F., Broxterman, H. J., and Borst, P. The human multidrug resistance-associated protein MRP is a plasma membrane drug-efflux pump, Proc. Natl. Acad. Sci. USA. 91: 8822-8826,1994.) Tubulin mutations have been found in cells selected for resistance to agents that polymerize microtubules, paclitaxel or epothilones. (Giannakakou, P., Gussio, R., Nogales, E., Downing, K. H., Zaharevitz, D., Bolbuck, B., Poy, G., Sackett, D., Nicolauo, K. C., Fojo, T. A common pharmacophore for epithilone and taxanes: molecular basis for drug resistance conferred by tubulin mutations in human cancer cells, Proc. Natl. Acad. Sci. USA. 97: 2904-2909, 2000; Giannakakou, P., Sackett, D. L., Kang, Y.-K., Zhan, A., Buters, J. T., M., Fojo, T., Poruchynsky, M. S. Paclitaxel-resistant human ovarian cancer cells have mutant b-tubulins that exhibit impaired paclitaxel-driven polymerization, J. Biol. Chem. 272: 17118-17125, 1997.) For paclitaxel resistance of this type, selection must be done with paclitaxel in the presence of an MDR-1 inhibitor to avoid the preferential overexpression of MDR1. Based on crystallographic data and molecular modeling of tubulin, the mutations occur in regions of tubulin thought to interact with taxanes. (Giannakakou, P., Gussio, R., Nogales, E., Downing, K. H., Zaharevitz, D., Bolbuck, B., Poy, G., Sackett, D., Nicolauo, K. C., Fojo, T. A common pharmacophore for epithilone and taxanes: molecular basis for drug resistance conferred by tubulin mutations in human cancer cells, Proc. Natl. Acad. Sci. USA. 97: 2904-2909, 2000.) While clinical significance is still being evaluated, one report found that 33% of patients with non-small cell carcinomas had tumors with tubulin mutations and such mutations are correlated with poor response to paclitaxel therapy. (Monzo, M., Rosell, R., Sanchez, J. J., Lee, J. S., O'Brate, A., Gonzalez-Larriba, J. L., Alberola, V., Lorenzo, J. C., Nunez, L., Ro, J. Y., Martin, C. Paclitaxel resistance in son-small cell lung cancer associated with beta-tubulin gene mutations, J. Clin. Oncol. 17: 1786-179, 1999.) Differential expression of tubulin isoforms has been found in some cell lines selected for paclitaxel or vinca alkaloid resistance. (Burkart, C. A., Kavallaris, M., Horwitz, S. B. The role of b-tubulin isotypes in resistance to antimitotic drugs, Biochim. Biophys. Acta. 1471: 01-09, 2001.) The clinical association with isotype alterations has not been fully studied, but alterations in isotype expression in patients resistant to paclitaxel have been found. (Kavallaris, M., Kuo, D. Y-.S., Burkhart, C. A., Regf, D. L., Norris, M. D., Haber, M., Horwitz, S. B. Taxol-resistant epithelial ovarian tumors are associated with altered expression of specific b-tubulin isotypes, J. Clin. Invest. 100: 1282-1293,1997.)

There is still a need for novel compounds which have chemical structures other than paclitaxel, which further have anticancer activity and in particular which have antimicrotubule activity against resistant cell lines and are useful for the treatment of cancer.

BRIEF SUMMARY OF THE INVENTION

In accordance with the present invention, there is provided compounds represented by Formula I:

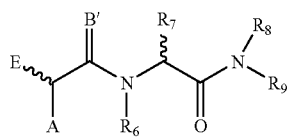

I wherein:
A is selected from the group consisting of an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms are optionally substituted with: =O, =S, OH, —$OR_{10}$, —$O_2CR_{10}$, —SH, —$SR_{10}$, —$SOCR_{10}$, —$NH_2$, —$NR_{10}H$, —$N(R_{10})_2$, —$NHCOR_{10}$, —$NR_{10}COR_{10}$, —I, Br, —Cl, —F, —CN, —$CO_2H$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, —$SO_2R_{10}$, wherein $R_{10}$ is a alkyl moiety of 1 to 10 carbon atoms, alkenyl moiety of 2 to 10 carbon atoms, aryl and a cyclic hydrocarbon moiety of 3 to 10 carbon atoms, aryl-R— and heteroaryl-R; or A is OR, S(O)R, S(O)$_2$R, SO$_2$NR$_2$, NR$_1$R$_2$ or N$_3$;

R is selected from the group consisting of H, an alkyl moiety of 1 to 18 carbon atoms, alkenyl moiety of 2 to 18 carbon atoms, aryl and a cyclic hydrocarbon moiety of 3 to 18 carbon atoms, wherein carbon atoms may optionally be replaced with 0 to 4 nitrogen atoms, 0 to 4 oxygen atoms, and 0 to 4 sulfur atoms, and the carbon atoms are optionally substituted with: =O, =S, OH, —$OR_{10}$, —$O_2CR_{10}$, —SH, —$SR_{10}$, —$SOCR_{10}$, —$NH_2$, —$NR_{10}H$, —$N(R_{10})_2$, —NHCOR$_{10}$, —NR$_{10}$COR$_{10}$, —I, Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, or —$SO_2R_{10}$;

B' is O or H$_2$;
E is the moiety

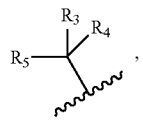

or aryl, a 5 to 14-membered monocyclic, bicyclic or tricyclic saturated or unsaturated hydrocarbon ring moiety wherein carbon atoms may optionally be replaced with 0 to 4 nitrogen atoms, 0 to 4 oxygen atoms, and 0 to 4 sulfur atoms wherein the carbon atoms may optionally be substituted with: R, =O, =S, OH, —$OR_{10}$, —$O_2CR_{10}$, —SH, —$SR_{10}$, —$SOCR_{10}$, —$NH_2$, —$NR_{10}H$, —$N(R_{10})_2$, —NHCOR$_{10}$, —NR$_{10}$COR$_{10}$, —I, Br, —Cl, —F, —CN, —$CO_2H$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, or —$SO_2R_{10}$;

$R_1$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —$OR_{10}$, —$O_2CR_{10}$, —SH, —$SR_{10}$, —$SOCR_{10}$, —$NH_2$, —$NR_{10}H$, —$N(R_{10})_2$, —NHCOR$_{10}$, —NR$_{10}$COR$_{10}$, —I, Br, —Cl, —F, —CN, —$CO_2H$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, or —$SO_2R_{10}$;

$R_2$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —$OR_{10}$, —$O_2CR_{10}$, —SH, —$SR_{10}$, —$SOCR_{10}$, —$NH_2$, —$NR_{10}H$, —$N(R_{10})_2$, —NHCOR$_{10}$, —NR$_{10}$COR$_{10}$, —I, Br, —Cl, —F, —CN, —$CO_2H$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, or —$SO_2R_{10}$;

$R_1$ and $R_2$ together may optionally form a ring of 3 to 7 carbon atoms wherein carbon atoms may optionally be replaced with 0 to 2 nitrogen atoms, 0 to 2 oxygen atoms and 0 to 2 sulfur atoms;

$R_3$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —$OR_{10}$, —$O_2CR_{10}$, —SH, —$SOCR_{10}$, —$NH_2$, —$NR_{10}H$, —$N(R_{10})_2$, —NHCOR$_{10}$, —NR$_{10}$COR$_{10}$, —I, Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, or —$SO_2R_{10}$;

$R_4$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —OR$_{10}$, —O$_2$CR$_{10}$, —SH, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_3$ and R$_4$ together may optionally form a ring of 3 to 7 carbon atoms wherein carbon atoms may optionally be replaced with 0 to 2 nitrogen atoms, 0 to 2 oxygen atoms and 0 to 2 sulfur atoms;

R$_5$ is selected from the group consisting of H, OH, NHR, SH, aryl, heteroaryl, an alkyl moiety of 1 to 10 carbon atoms, alkenyl moiety of 2 to 10 carbon atoms and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —OR$_{10}$, —O$_2$CR$_{10}$, —SH, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_5$ and A may optionally form a ring of 5 to 7 carbon atoms wherein carbon atoms may optionally be replaced with 0 to 2 nitrogen atoms, 0 to 2 oxygen atoms, and 0 to 2 sulfur atoms;

R$_6$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_7$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_8$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_9$ is selected from the group

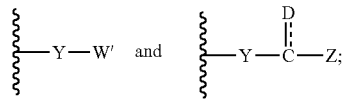

W' is selected from the group consisting of SO$_2$R$_{16}$, SO$_3$R$_{14}$, SO$_2$NR$_{14}$R$_{15}$, P(O)(OR$_{14}$)(OR$_{15}$), CN, OH, tetrazole, a moiety

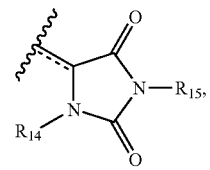

and SO$_2$NRR where the R groups may form a 4 to 8 membered ring wherein carbon atoms may optionally be replaced with 0 to 2 nitrogen atoms, 0 to 2 oxygen atoms and 0 to 2 sulfur atoms;

R$_{14}$ and R$_{15}$ are independently selected from the group H and alkyl of 1 to 6 carbon atoms;

R$_{16}$ is alkyl of 1 to 6 carbon atoms;

D is O or OH;

Z and Y may optionally form a ring of 5 to 7 carbon atoms wherein carbon atoms may optionally be replaced with 0 to 2 nitrogen atoms, 0 to 2 oxygen atoms, and 0 to 2 sulfur atoms;

Y is an alkyl moiety of 1 to 10 carbon atoms optionally substituted with R, ArylR-, or X, or an alkenyl moiety of 2 to 10 carbon atoms optionally substituted with R, ArylR-, or X;

Z is defined as a moiety selected from the group consisting of: H, alkyl of 1 to 6 carbon atoms, —NRN(R)$_2$, R, aryl, heteroaryl, aralkyl, —OR, —SH, —SR, —NH$_2$, —NHR, —NROR, —N(R)$_2$, NH—NH$_2$, NRR where the R groups may form a 4 to 8 membered ring wherein carbon atoms may optionally be replaced with 0 to 2 nitrogen atoms, 0 to 2 oxygen atoms, and 0 to 2 sulfur atoms, —NHCH(R$_{11}$)COOH; and —NRCH(R$_{11}$)COOH, wherein R$_{11}$ is a moiety having the formula: R, or —(CH$_2$)$_n$NR$_{12}$R$_{13}$, wherein n=1-4 and R$_{12}$ and R$_{13}$ are independently selected from the group consisting of: H; R; and —C(NH)(NH$_2$); or Z is selected from moieties of the formula

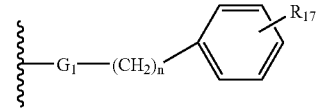

and

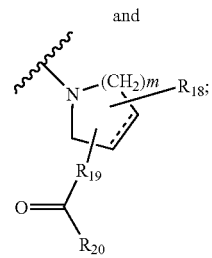

the dotted line is an optional bond;

G$_1$ is selected from O, N and S;

m is an integer of 1 to 3;

u is an integer of 0-5;

$R_{17}$ is phenyl, or O—$(CH_2)_n$phenyl;

$R_{18}$ is H or OH;

$R_{19}$ is selected from a bond, an alkyl moiety of 1 to 10 carbon atoms optionally substituted with an alkyl moiety of 1 to 10 carbon atoms, and alkoxy of 1 to 10 carbon atoms;

$R_{20}$ is selected from $OR_{14}$, NH—$R_{21}$, a moiety of the formula

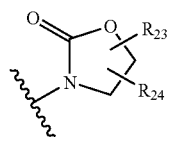

and a moiety of the formula

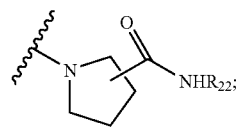

$R_{21}$ is an alkyl moiety of 1 to 10 carbon atoms optionally substituted with aryl and heteroaryl;

$R_{22}$ is an alkyl moiety of 1 to 10 carbon atoms optionally substituted with aryl;

X is defined as a moiety selected from the group consisting of: —OH, —OR, =O, =S, —$O_2$CR, —SH, —SR, —SOCR, —$NH_2$, —NHR, —N(R)$_2$, —NHCOR, —NRCOR, —I, —Br, —Cl, —F, —CN, —$CO_2$H, —$CO_2$R, —CHO, —COR, —$CONH_2$, —CONHR, —CON(R)$_2$, —COSH, —COSR, —$NO_2$, —$SO_3$H, —SOR, and —$SO_2$R;

Aryl is defined as an aromatic hydrocarbon moiety having 6, 10 or 14 carbon atoms, optionally substituted with R or Z;

Heteroaryl means a 5- or 6-membered heterocyclic ring, which may be fused to another 5- or 6-membered heterocyclic ring, especially heteroaromatic rings which contain 1 to 3 heteroatoms independently selected from O, N and S optionally substituted with R or X or fused to a cyclic hydrocarbon moiety of 3 to 10 carbon atoms;

provided when A is $NR_1R_2$, B' is O, D is OH and $R_1$, $R_2$, $R_3$, $R_4$, $R_5$, $R_6$, $R_7$ and $R_8$ are independently selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, 0 to 4 nitrogen atoms, 0 to 4 oxygen atoms, and 0 to 4 sulfur atoms, and the carbon atoms may optionally be substituted with: =O, =S, OH, —$OR_{10}$, —$O_2CR_{10}$, —SH, —$SR_{10}$, —$SOCR_{10}$, —$NH_2$, —$NR_{10}$H, —$N(R_{10})_2$, —$NHCOR_{10}$, —$NR_{10}COR_{10}$, —I, Br, —Cl, —F, —CN, —$CO_2$H, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3$H, —$SOR_{10}$, or —$SO_2R_{10}$;

then Z is not a moiety selected from the group consisting of: —OH, —OR; —SH; —SR; —$NH_2$; —NHR; —N(R)$_2$; —NHCH($R_{11}$)COOH; and —NRCH($R_{11}$)COOH, wherein $R_{11}$ is a moiety having the formula: R, or —$(CH_2)_n NR_{12}R_{13}$, wherein n=1-4 and $R_{12}$ and $R_{13}$ are independently selected from the group consisting of: H; R; and —C(NH)(NH$_2$);

or pharmaceutically acceptable salts thereof.

Accordingly, an object of this invention is to provide compounds which overcome the above described limitations in cancer treatment by providing a method for treating tumors that are resistant to currently marketed antimitotic agents. In particular, the method is useful in tumor cells that overexpress MDR-1, MXR, or MRP.

Further, an additional object of this invention provides a method for treating or inhibiting multiple drug resistant tumors in a mammal in need thereof. In particular, this application demonstrates that compounds of the invention are effective in tumor cells that express multiple drug resistance and that have inherent or acquired resistance in drug resistant tumors.

The present invention also provides a pharmaceutical composition which comprises a compound of this invention in combination or association with one or more pharmaceutically acceptable carriers. In particular, the present invention provides a pharmaceutical composition which comprises an effective amount of a compound of this invention and and one or more pharmaceutically acceptable carriers.

Definitions:

The term alkyl means a saturated linear, or branched, hydrocarbon moiety of 1 to 10 carbon atoms. In some embodiments of the invention the moiety may optionally be 1 to 18 carbon atoms or 1 to 6 carbon atoms. Examples include methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylphenyl, 2,2-dimethylbutyl, n-heptyl, 2-methylhexyl, and the like unless otherwise specified. The carbon atoms may optionally be replaced with 0 to 4 nitrogen atoms, 0 to 4 oxygen atoms, and 0 to 4 sulfur atoms, and the carbon atoms are optionally substituted with: =O, =S, OH, —$OR_{10}$, —$O_2CR_{10}$, —SH, —$SR_{10}$, —$SOCR_{10}$, —$NH_2$, —$NR_{10}$H, —$N(R_{10})_2$, —$NHCOR_{10}$, —$NR_{10}COR_{10}$, —I, Br, —Cl, —F, —CN, —$CO_2$H, —CHO, —$COR_{10}$, —$CONH_2$, —$CONHR_{10}$, —$CON(R_{10})_2$, —COSH, —$COSR_{10}$, —$NO_2$, —$SO_3$H, —$SOR_{10}$, —$SO_2R_{10}$, wherein $R_{10}$ is a an alkyl moiety of 1 to 10 carbon atoms, alkenyl moiety of 2 to 10 carbon atoms, aryl and a cyclic hydrocarbon moiety of 3 to 10 carbon atoms, aryl-R— and heteroaryl-R.

The term alkenyl means an unsaturated linear, or branched, hydrocarbon moiety means a moiety of 2 to 10 carbon atoms containing at least one carbon-carbon double bond, each double bond being independently cis, trans or a nongeometric isomer wherein carbon atoms may optionally be replaced with 0 to 4 nitrogen atoms, 0 to 4 oxygen atoms, and 0 to 4 sulfur atoms, and the carbon atoms are optionally substituted with: =O, =S, OH, —$OR_{10}$, —$O_2CR_{10}$, —SH, —$SR_{10}$, —$SOCR_{10}$, —$NH_2$, —$NR_{10}$H, —$N(R_{10})_2$, —$NHCOR_{10}$, —$NR_{10}COR_{10}$, —I, Br, —Cl, —F, —CN, —$CO_2$H, —CHO, —$COR_{10}$, —$CONH_2$, —$CONHR_{10}$, —$CON(R_{10})_2$, —COSH, —$COSR_{10}$, —$NO_2$, —$SO_3$H, —$SOR_{10}$, —$SO_2R_{10}$, wherein $R_{10}$ is an alkyl moiety of 1 to 10 carbon atoms, alkenyl moiety of 2 to 10 carbon atoms, aryl and a cyclic hydrocarbon moiety of 3 to 10 carbon atoms, aryl-R— and heteroaryl-R.

The term cyclic hydrocarbon moiety means a saturated or unsaturated cyclic hydrocarbon moiety of 3 to 10 carbon atoms, a monocyclic cycloalkyl or cycloalkenyl ring of 3 to 10 carbon atoms wherein carbon atoms may optionally be replaced with 0 to 4 nitrogen atoms, 0 to 4 oxygen atoms, and 0 to 4 sulfur atoms, and the carbon atoms are optionally substituted with: =O, =S, OH, —$OR_{10}$, —$O_2CR_{10}$, —SH, —$SR_{10}$, —$SOCR_{10}$, —$NH_2$, —$NR_{10}$H, —$N(R_{10})_2$, —$NHCOR_{10}$, —$NR_{10}COR_{10}$, —I, Br, —Cl, —F, —CN, —$CO_2$H, —CHO, —$COR_{10}$, —$CONH_2$, —$CONHR_{10}$, —$CON(R_{10})_2$, —COSH, —COSR$_{10}$, —NO$_2$, —SO$_3$H, —SOR$_{10}$, —SO$_2$R$_{10}$, wherein R$_{10}$ is an alkyl moiety of 1 to 10 carbon atoms, alkenyl moiety of 2 to 10 carbon atoms, aryl and a cyclic hydrocarbon moiety of 3 to 10 carbon atoms, aryl-R— and heteroaryl-R. In some embodiments of the invention the cyclic hydrocarbon may optionally be a 5 to 14-membered monocyclic, bicyclic or tricyclic saturated or unsaturated hydrocarbon ring moiety wherein carbon atoms may optionally be replaced with 0 to 4 nitrogen atoms, 0 to 4 oxygen atoms, and 0 to 4 sulfur atoms wherein the carbon atoms may optionally be substituted with: R, =O, =S, OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F, —CN, —CO$_2$H, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

Aryl is defined as an aromatic hydrocarbon moiety having 6, 10 or 14 carbon atoms, preferably 6 to 10 carbon atoms optionally substituted with R or X. In particular an aromatic moiety is selected from the group consisting of: phenyl, naphthyl, anthracyl, and phenanthryl optionally substituted with R or X;

The term heteroaryl means a 5- or 6-membered heterocyclic ring, which may be fused to another 5- or 6-membered heterocyclic ring, especially heteroaromatic rings which contain 1 to 3 heteroatoms selected from O, N and S optionally substituted with R or X or fused to a cyclic hydrocarbon moiety of 3 to 10 carbon atoms. Exemplary heteroaromatic rings include but are not limited to thienyl, furyl, indolyl, pyrrolyl, thiophenyl, benzofuryl, benzothiophenyl, quinolyl, isoquinolyl, imidazolyl, thiazolyl, oxazolyl, and pyridyl.

The term alkoxy means an alkyl-O— group in which the alkyl group is as hereinbefore defined. Exemplary alkoxy groups include but are not limited to methoxy, ethoxy, n-propoxy, 1-propoxy, n-butoxy and t-butoxy.

Aralkyl as used herein means an aryl-alkyl group in which the aryl and alkyl group are previously defined. Exemplary non-limiting examples of aralkyl groups include benzyl and phenethyl.

The term phenyl as used herein refers to a 6-membered carbon aromatic ring.

Preferably the recitation of a compound of Formula (I) herein covers all possible salts of the compound, and denotes all possible isomers possible within the structural formula given for such compound, including geometrical and optical isomers. Unless otherwise stated, materials described herein comprising a compound for which isomers exist, are to be regarded as covering individual isomers, and, mixtures of isomers including racemic mixtures.

Embodiments of this invention include the following:

in a compound of Formula (I), the following substituents alone, or in combination, are preferred:

(a) R$_1$ is H, methyl, ethyl, propyl, or n-butyl and R$_2$ is methyl, ethyl, propyl, or n-butyl; or, where R$_1$ and R$_2$ taken together with the nitrogen atom to which they are attached form a 3 to 8 membered ring; more preferably R$_1$ is H and R$_2$ is CH$_3$;

(b) preferably no more than one of R$_3$ and R$_4$ is H; more preferably, R$_3$ and R$_4$ are independently: methyl, ethyl, n-propyl or n-butyl, or, where R$_3$ and R$_4$ are joined together to form a β-cyclopropyl, β-cyclobutyl, β-cyclopentyl or β-cyclohexyl ring; most preferably R$_3$ and R$_4$ are each methyl;

(c) R$_5$: is cyclohexyl; Aryl in the definition of R$_5$ is preferably phenyl, or naphthyl; heteroaryl in the definition of R$_5$ is preferably thienyl, or indolyl; preferably R$_5$ is phenyl, or indolyl; most preferably R$_5$ is phenyl;

(d) preferably E is phenyl, adamantly, or 1,2,3,4-tetrahydro-1-naphthalenyl;

(e) R$_6$ and R$_8$ are independently: H or methyl, more preferably R$_6$ is H and R$_8$ is methyl;

(f) R$_7$ is a three to six carbon, branched alkyl moiety; more preferably R$_7$ is —C(CH$_3$)$_3$;

(g) in R$_9$, Z is a moiety

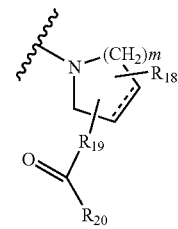

where m is 1 or 2; R$_{19}$ is a bond or a saturated alkyl chain of 3 or 4 carbon atoms optionally substituted with alkoxy of 1 to 3 carbon atoms; R$_{20}$ is a moiety

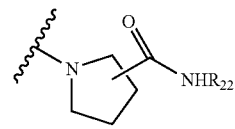

where R$_{22}$ is alkyl of 1 to 3 carbon atoms substituted with aryl and thiazole.

(h) R$_{19}$ is an alkyl moiety of 1 to 6 carbon atoms optionally substituted with a alkyl moiety of 1 to 6 carbon atoms, and alkoxy of 1 to 6 carbon atoms straight or branched chain alkyl;

(i) in R$_9$ where Z is preferably, morpholino, piperazinyl, imidazole, phenyl, N-methyl-piperazinyl, N-benzyl-piperazinyl or pyrrolidin-1-yl carboxylic acid or alkyl ester;

(j) R$_9$ is preferably —C(R$_{15}$)—C=C(R$_{16}$)C(O)-Z wherein R$_{15}$ is methyl, ethyl, n-propyl, isopropyl, tert-butyl, iso-butyl, or sec-butyl and R$_{16}$. is H, methyl, ethyl, propyl, iso-propyl, n-butyl, iso-butyl or sec-butyl;

(k) R$_9$ is preferably

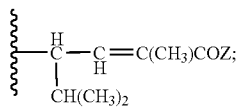

R$_9$ is more preferably;

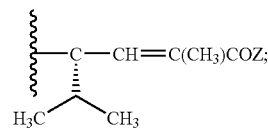

$R_9$ is most preferably;

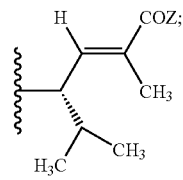

Additionally preferred compounds of the invention are those of Formula (I) wherein:
A is $NR_1R_2$;
$R_1$ is methyl;
$R_2$ is H;
$R_3$ and $R_4$ are methyl;
$R_5$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, said carbon atoms being optionally substituted with: =O, =S, OH, $-OR_{10}$, $-O_2CR_{10}$, $-SH$, $-SOCR_{10}$, $-NH_2$, $-NR_{10}H$, $-N(R_{10})_2$, $-NHCOR_{10}$, $-NR_{10}COR_{10}$, $-I$, Br, $-Cl$, $-F$, $-CN$, $-CO_2H$, $-CO_2R_{10}$, $-CHO$, $-COR_{10}$, $-CONH_2$, $-CONHR_{10}$, $-CON(R_{10})_2$, $-COSH$, $-COSR_{10}$, $-NO_2$, $-SO_3H$, $-SOR_{10}$, or $-SO_2R_{10}$, wherein $R_{10}$ is an alkyl moiety of 1 to 10 carbon atoms, alkenyl moiety of 2 to 10 carbon atoms, aryl and a cyclic hydrocarbon moiety of 3 to 10 carbon atoms, aryl-R— and heteroaryl-R;
$R_7$ is preferably t-butyl;
$R_9$ is preferably $-C(R_{15})-C=C(R_{16})C(O)$-Z wherein $R_{15}$ is methyl, ethyl, n-propyl, isopropyl, tert-butyl, iso-butyl, or sec-butyl and $R_{16}$ is H, methyl, ethyl, propyl, iso-propyl, n-butyl, iso-butyl or sec-butyl;
$R_9$ is:

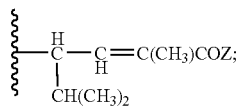

$R_9$ is more preferably

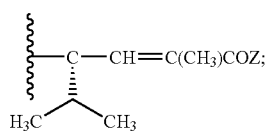

$R_9$ is most preferably

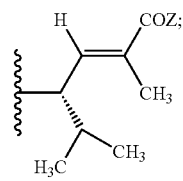

The most preferred absolute configurations of compounds of Formula (I) wherein the absolute configurations of moieties a, b and c of Formula (I)

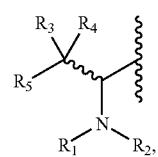

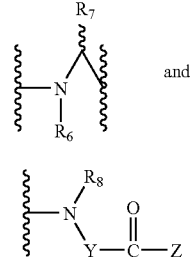

are selected from:

| a | b | c |
|---|---|---|
| S | S | S |
| R | S | S and |
| S | S | R. |

Additionally preferred compounds of the invention are those of Formula (I) and pharmaceutically acceptable salts thereof wherein:
W' is selected from the group consisting of tetrazole, $SO_3C_2H_5$, $SO_3H$, $P(O)(OCH_3)_2$; $P(O)(OH)(OCH_3)$, $P(O)(OH)_2$, $P(O)(OC_2H_5)_2$,

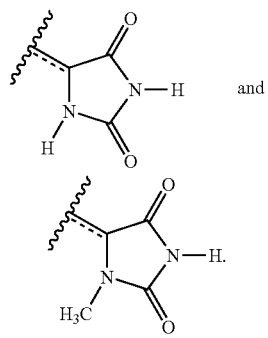

Specifically preferred compounds of the invention including pharmaceutically acceptable salts thereof include:
N,β,β,3-tetramethyl-L-phenylalanyl-$N^1$—[(1S,2E)-1-isopropyl-3-methyl-4-morpholin-4 -yl-4-oxobut-2-enyl]-$N^1$,3-dimethyl-L-valinamide,
N,β,β,3,4-Pentamethyl-L-phenylalanyl-$N^1$—[(1S,2E)-1-isopropyl-3-methyl-4-morpholin- 4-yl-4-oxobut-2-enyl]-$N^1$,3-dimethyl-L-valinamide,
N,β,β,3,5-Pentamethyl-L-phenylalanyl-$N^1$—[(1S,2E)-1-isopropyl-3-methyl-4-morpholin-4-yl-4-oxobut-2-enyl]-N',3-dimethyl-L-valinamide,
N,β,β,3,4-Pentamethyl-D-phenylalanyl-$N^1$—[(1S,2E)-1-isopropyl-3-methyl-4-morpholin- 4-yl-4-oxobut-2-enyl]-$N^1$,3-dimethyl-L-valinamide, N,β,β,3,5-Pentamethyl-D-phenylalanyl-N¹—[(1S,2E)-1-isopropyl-3-methyl-4-morpholin-4-yl-4-oxobut-2-enyl]-N¹,3-dimethyl-L-valinamide, N, β,β,3-Tetramethyl-L-phenylalanyl-N¹—[(1S,2E)-1-isopropyl-3-methyl-4-(4-methylpiperazin-1-yl)-4-oxobut-2-enyl]-N¹,3-dimethyl-L-valinamide, trifluoroacetic acid salt, N, β,β,3,4-Pentamethyl-L-phenylalanyl-N¹—[(1S,2E)-1-isopropyl-3-methyl-4-(4-methylpiperazin-1-yl)-4-oxobut-2-enyl]-N¹,3-dimethyl-L-valinamide, N, β,β,3,5-Pentamethyl-L-phenylalanyl-N¹—[(1S,2E)-1-isopropyl-3-methyl-4-(4-methylpiperazin-1-yl)-4-oxobut-2-enyl]-N¹,3-dimethyl-L-valinamide, 1-{(2E,4S)-2,5-Dimethyl-4-[methyl(N, β,β,3-tetramethyl-L-phenylalanyl-3-methyl-L-valyl hex-2-enoyl}-D-prolyl-N-benzyl-D-prolinamide trifluoroacetic acid salt, 1-{(2E,4S)-2,5-Dimethyl-4-[methyl(N, β,β,3,4-pentamethyl-L-phenylalanyl-3-methyl-L -valyl)amino]hex-2-enoyl}-L-prolyl-N-benzyl-L-prolinamide, 1-{(2E,4S)-2,5-Dimethyl-4-[methyl(N, β,β,3,5-pentamethyl-L-phenylalanyl-3-methyl-L- valyl)amino]hex-2-enoyl}-L-prolyl-N-benzyl-L-prolinamide, N, β,β,3,4-Pentamethyl-L-phenylalanyl-N¹—[(1S,2E)-4-(4-benzylpiperazin-1-yl)-1-isopropyl-3-methyl-4-oxobut-2-enyl]-N¹,3-dimethyl-L-valinamide, N, β,β,3,4-Pentamethyl-D-phenylalanyl-N¹—[(1S,2E)-4-(4-benzylpiperazin-1-yl)-1-isopropyl-3-methyl-4-oxobut-2-enyl]-N¹,3-dimethyl-L-valinamide, N, β,β,3,5-Pentamethyl-L-phenylalanyl-N¹—[(1S,2E)-4-(4-benzylpiperazin-1-yl)-1 -isopropyl-3-methyl-4-oxobut-2-enyl]-N¹,3-dimethyl-L-valinamide, N, β,β,β-Tetramethyl-L-phenylalanyl-N¹—[(1S,2E)-4-(4-benzylpiperazin-1-yl)-1-isopropyl-3-methyl-4-oxobut-2-enyl]-N¹,3-dimethyl-L-valinamide, 3-Chloro-N, β,β-trimethyl-L-phenylalanyl-N¹-[(1S,2E)-4-(4-benzylpiperazin-1-yl)-1-isopropyl-3-methyl-4-oxobut-2-enyl]-N¹,3-dimethyl-L-valinamide, N, β,β,3,4-Pentamethyl-L-phenylalanyl-N¹-{(1S,2E)-4-[(2S)-2-(methoxycarbonyl)pyrrolidin-1-yl]-1-isopropyl-3-methyl-4-oxobut-2-enyl]-N¹,3-dimethyl-L-valinamide, N, β,β,3,4-Pentamethyl-L-phenylalanyl-N¹-{(1S,2E)-4-[(2S)-2-carboxypyrrolidin-1-yl]- -1-isopropyl-3-methyl-4-oxobut-2-enyl}-N¹,3-dimethyl-L-valinamide, N, β,β,3,5-Pentamethyl-L-phenylalanyl-N¹-{(1S,2E)-4-[(2S)-2-(methoxycarbonyl)pyrrolidin-1-yl]-1-isopropyl-3-methyl-4-oxobut-2-enyl}-N¹,3-dimethyl-L-valinamide, N, β,β,3,5-Pentamethyl-L-phenylalanyl-N¹-{(1S,2E)-4-[(2S)-2-carboxypyrrolidin-1-yl]-1-isopropyl-3-methyl-4-oxobut-2-enyl}-N¹,3-dimethyl-L-valinamide, N, β,β,3-Tetramethyl-L-phenylalanyl-N¹-{(1S,2E)-4-[(2S)-2-(methoxycarbonyl)pyrrolidin-1-yl]-1-isopropyl-3-methyl-4-oxobut-2-enyl}-N¹,3-dimethyl-L-valinamide, N, β,β,3-Tetramethyl-L-phenylalanyl-N¹-{(1S,2E)-4-[(2S)-2-carboxypyrrolidin-1-yl]-1-isopropyl-3-methyl-4-oxobut-2-enyl}-N¹,3-dimethyl-L-valinamide, 3-Chloro-N, β,β-trimethyl-L-phenylalanyl-N¹-{(1S,2E)-4-[(2S)-2-(methoxycarbonyl)pyrrolidin-1-yl]-1-isopropyl-3-methyl-4-oxobut-2-enyl}-N¹,3-dimethyl-L-valinamide, 3-Chloro-N, β,β-trimethyl-L-phenylalanyl-N¹-{(1S,2E)-4-[(2S)-2-carboxypyrrolidin-1 -yl]-1-isopropyl-3-methyl-4-oxobut-2-enyl}-N¹,3-dimethyl-L-valinamide, (E,4S)-4-[((2S)-3,3-dimethyl-2-{[(2S)-3-methyl-2-(methylamino)-3-phenylbutanoyl]amino}butanoyl)(methyl)amino]-N-hydroxy-2,5-dimethyl-2-hexenamide, N, β,β-trimethyl-L-phenylalanyl-N¹-[(1S,2E)-1-isopropyl-3-methyl-4-(4-methyl-1-piperazinyl)-4-oxo-2-butenyl]-N¹,3-dimethyl-L-valinamide, (2S)-N-[(1S,2E)-1-isopropyl-3-methyl-4-(4-morpholinyl)-4-oxo-2-butenyl]-N,3,3-trimethyl-2-{[(2S)-3-methyl-2-(methylamino)-3-phenylbutanoyl]amino}butanamide, 1-{(2E,4S)-2,5-dimethyl-4-[methyl(N-methyl-3-phenyl-L-valyl-3-methyl-L-valyl)amino]hex-2-enoyl}-D-prolyl-N-benzyl-D-prolinamide, N, β,β-trimethyl-L-phenylalanyl-N¹-{(1S,2E)-1-isopropyl-4-[(2S)-2-((1R,2R    )-1-methoxy-2-methyl-3-oxo-3-{[(1S)-2-phenyl-1-(1,3-thiazolyl-2-yl)ethyl]amino}propyl)pyrrolidin-1-yl]-3-methyl-4-oxobut-2-dimethyl-L-valinamide, N, β,β-trimethyl-L-phenylalanyl-N¹-((1S,2E)-4-{(2S)-2-[(1R,2R)-1,3-dimethoxy-2-methyl-3-oxopropyl]pyrrolidin-1-yl}-1-isopropyl-3-methyl-4-oxobut-2-enyl)-N¹,3-dimethyl-L-valinamide, N-methyl-3-phenyl-L-valyl-N¹-[(1S,2E)-1-isopropyl-4-((2S)-2-{(1R,2R)-1-methoxy-2-methyl-3-oxo-[(2-phenethyl)amino]propyl}pyrrolidin-1-yl)-3-methyl-4-oxobut-2-enyl]-N¹,3-dimethyl-L-valinamide, N, β,β-trimethyl-L-phenylalanyl-N¹-[(1S,2E)-1-isopropyl-4-((2S)-2-{(1R,2R)-1-methoxy-2-methyl-3-[(4R,5S)-4-methyl-2-oxo-5-phenyl-1,3-oxazolidin-3-yl]-3-oxopropyl}pyrrolidin-1-yl)-3-methyl-4-oxovalinamide, Methyl N, β,β-trimethyl-L-phenylalanyl-3-methyl-L-valyl-N-methyl-L-valyl-L-prolinate, N, β,β-trimethyl-L-phenylalanyl-3-methyl-L-valyl-N-methyl-L-valyl-L-prolyl-N-benzyl-L-prolinamide, N, β,β-trimethyl-L-phenylalanyl-N¹-{(1S,2E)-4-[(2S)-2-(methoxycarbonyl)pyrrolidin-1-yl]-1-isopropyl-3-methyl-4-oxobut-2-enyl}-N¹,3-dimethyl-L-valinamide, N, β,β-trimethyl-L-phenylalanyl-N¹-{(1S,2E)-4-[(2S)-2-carboxypyrrolidin-1-yl]-1 -isopropyl-3-methyl-4-oxobut-2-enyl}-N¹,3-dimethyl-L-valinamide, N, β,β-trimethyl-L-phenylalanyl-N¹-{(1S,2E)-4-[(2S)-2-(2-phenethoxycarbonyl)pyrrolidin-1-yl]-1-isopropyl-3-methyl-4-oxobut-2-enyl}-N¹,3-dimethyl-L-valinamide, N, β,β-trimethyl-L-phenylalanyl-N¹-((1S,2E)-4-{4-[3-(dimethylamino)propyl]piperazin-1-yl}-1-isopropyl-3-methyl-4-oxobut-2-enyl)-N¹,3-dimethyl-L-valinamide, N, β,β-trimethyl-L-phenylalanyl-N¹—[(1S,2E)-4-(4-benzylpiperazin-1-yl)-1-isopropyl -methyl-4-oxobut-2-enyl]-N¹,3-dimethyl-L-valinamide, N, β,β-trimethyl-L-phenylalanyl-N¹-{(1S,2E)-4-[(2S,4R)-2-(methoxycarbonyl)-4-hydroxypyrrolidin-1-yl]-1-isopropyl-3-methyl-4-oxobut-2-enyl}-N¹,3-dimethyl-L-valinamide, N, β,β-trimethyl-L-phenylalanyl-N¹-{(1S,2E)-4-[(2R)-2-(methoxycarbonyl)pyrrolidin-1-yl]-1-isopropyl-3-methyl-4-oxobut-2-enyl}-N¹,3-dimethyl-L-valinamide, N, β,β-trimethyl-L-phenylalanyl-N¹-{(1S,2E)-4-[(2S,4R)-2-carboxy-4-hydroxypyrrolidin-1-yl]-1-isopropyl-3-methyl-4-oxobut-2-enyl}-N¹,3-dimethyl-L-valinamide, N, β,β-trimethyl-L-phenylalanyl-N¹-{(1S,2E)-4-[(2R)-2-carboxypyrrolidin-1-yl]-1 -isopropyl-3-methyl-4-oxobut-2-enyl}-N¹,3-dimethyl-L-valinamide, 3-cyclohexyl-N-methyl-L-valyl-N¹-{(1S,2E)-1-isopropyl-4-[(2S)-2-((1R,2R)-1-methoxy-    2-methyl-3-oxo-3-{[(1S)-2-phenyl-1-(1,3-thiazol-2-yl)ethyl]amino}propyl)pyrrolidin-1-yl]-3-methyl-4-oxobut-2-enyl}-N¹,3-dimethyl-L-valinamide, 3-cyclohexyl-N-methyl-L-valyl-N¹-{(1S,2E)-4-[(2S)-2-(methoxycarbonyl)pyrrolidin-1-yl]-1-isopropyl-3-methyl-4-oxobut-2-enyl}-N¹,3-dimethyl-L-valinamide, 3-cyclohexyl-N-methyl-L-valyl-N¹-{(1S,2E)-4-[(2S)-2-carboxypyrrolidin-1-yl]-1-isopropyl-3-methyl-4-oxobut-2-enyl}-N¹,3-dimethyl-L-valinamide, N,β,β-trimethyl-L-phenylalanyl-N¹-{(1S,2E)-4-[(2S)-2-carboxy-2,5-dihydro-1H-pyr 1-yl]-1-isopropyl-3-methyl-4-oxobut-2-enyl}-N¹,3-dimethyl-L-valinamide, N, β,β-trimethyl-L-phenylalanyl-N¹-{(1S,2E)-1-isopropyl-4-[(2S)-2-(methoxycarbonyl)piperidin-1-yl]-3-methyl-4-oxobut-2-enyl}-N¹,3-dimethyl-L-valinamide, N, β,β-trimethyl-L-phenylalanyl-N¹-{(1S,2E)-4-[(2S)-2-carboxypiperidin-1-yl]-1-isopropyl-3-methyl-4-oxobut-2-enyl}-N¹,3-dimethyl-L-valinamide, 3-cyclohexyl-N-methyl-L-valyl-N¹-[(1S,2E)-1-isopropyl-4-((2S)-2-{(1R,2 2-methyl-3-[(4R,5S)-4-methyl-2-oxo-5-phenyl-1,3-oxazolidin-3-yl]-3-oxopropyl}pyrrolidin-1-yl)-3-methyl-4-oxobut-2-enyl]-N¹,3-dimethyl-L-valinamide, N,β,β-trimethyl-L-phenylalanyl-N¹-{(1S,2E)-1-isopropyl-4-[methoxy(methyl)amino]-3-methyl-4-oxobut-2-enyl}-N¹,3-dimethyl-L-valinamide, N,β,β-trimethyl-L-phenylalanyl-N¹-{(1S,2E)-4-[(1,1'-biphenyl-4-ylmethyl)amino]-1-isopropyl-3-methyl-4-oxobut-2-enyl}-N¹,3-dimethyl-L-valinamide, N,β,β-trimethyl-L-phenylalanyl-N¹-((1R,2E)-4-{[4-(benzyloxy)benzyl]oxy}-1-isopropyl-3-methyl-4-oxobut-2-enyl)-N¹,3-dimethyl-L-valinamide, (2E,4S)-4-[{N-[(2S)-2-(1-adamantyl)-2-(methylamino)ethanoyl]-3-methyl-L-valyl}(methyl)amino]-2,5-dimethyl-2-hexenoic acid, (2E,4S)-4-[{N-[(2R)-2-(1-adamantyl)-2-(methylamino)ethanoyl]-3-methyl-L-valyl}(methyl)amino]-2,5-dimethyl-2-hexenoic acid, (2E,4S)-2,5-dimethyl-4-(methyl{3-methyl-N-[(2S)-2-(methylamino)-2-phenylethanoyl]-L- valyl}amino)-2-hexenoic acid, (2E,4S)-2,5-dimethyl-4-(methyl{3-methyl-N-[(2,2,4-trimethylthiomorpholin-3-yl)carbonyl]-L-valyl}amino)hex-2-enoic acid, (2E,4S)-2,5-dimethyl-4-(methyl{3-methyl-N-[(2S)-2-(methylamino)-2-(1-methyl-1,2,3,4-tetrahydro-1-naphthalenyl)ethanoyl]-L-valyl}amino)-2-hexenoic acid, (2E,4S)-2,5-dimethyl-4-(methyl{3-methyl-N-[(2R)-2-(methylamino)-2-(1-methyl-1,2,3,4-tetrahydro-1-naphthalenyl)ethanoyl]-L-valyl}amino)-2-hexenoic, 3-hydroxy-N-methyl-L-valyl-N¹-[(1 S,2E)-4-ethoxy-1-isopropyl-3-methyl-4-oxo-2-butenyl]-N¹,3-dimethyl-L-valinamide, 3-hydroxy-N,N-dimethyl-L-valyl-N¹-[(1 S,2E)-4-ethoxy-1-isopropyl-3-methyl-4-oxo-2-butenyl]-N¹,3-dimethyl-L-valinamide, 1-methyl-L-prolyl-N¹-[(1 S,2E)-3-carboxy-1-isopropylbut-2-enyl]-N¹,3-dimethyl-L-va N, β,β-trimethyl-L-phenylalanyl-N¹-[(1S,2E)-3-(ethoxysulfonyl)-1-isopropylprop-2-enyl]-N¹,3-dimethyl-L-valinamide, N, β,β-trimethyl-L-phenylalanyl-N¹-[(1S,2E)-1-isopropyl-3-sulfoprop-2-enyl]-N¹,3-dimethyl-L-valinamide, N, β,β-trimethyl-L-phenylalanyl-N¹-[(1S,2E)-3-(ethoxysulfonyl)-1-isopropylbut-2-enyl]N¹,3-dimethyl-L-valinamide, N, β,β-trimethyl-L-phenylalanyl-N¹-[(1S,2E)-1-isopropyl-3-sulfobut-2-enyl]N¹,3-dimethyl-L-valinamide, N, β,β-trimethyl-L-phenylalanyl-N¹-[(1S,2Z)-1-isopropyl-3-sulfobut-2-enyl]-N¹,3-dimethyl-L-valinamide, N, β,β-trimethyl-L-phenylalanyl-N¹-[(1S,2E)-3-(dimethoxyphosphoryl)-1-isopropylprop-2-enyl]-N¹,3-dimethyl-L-valinamide, N, β,β-trimethyl-L-phenylalanyl-N¹-{(1S,2E)-3-[hydroxy(methoxy)phosphoryl]-1-isopropylprop-2-enyl}-N¹,3-dimethyl-L-valinamide, N, β,β-trimethyl-L-phenylalanyl-N¹-[(1S,2E)-1-isopropyl-3-phosphonoprop-2-enyl]-N¹,3-dimethyl-L-valinamide, N, β,β-trimethyl-L-phenylalanyl-N¹-[(1S,2E)-3-(diethoxyphosphoryl)-1-isopropyl-but-2-enyl]-N¹,3-dimethyl-L-valinamide, N, β,β-trimethyl-L-phenylalanyl-N¹-[(1S,2E)-1-isopropyl-3-phosphonobut-2-enyl]-N¹,3-dimethyl-L-valinamide, N, β,β-trimethyl-L-phenylalanyl-N¹-[(1S,2E)-1-isopropyl-3-methyl-4-oxo-4-(1,3-thiazol-2-yl)but-2-enyl]-N¹,3-dimethyl-L-valinamide, N, β,β-trimethyl-L-phenylalanyl-N¹-[(1S,2E)-4-hydroxy-1-isopropyl-3-methyl-4-phenylbut-2-enyl}-N-1,3-dimethyl-L-valinamide, N, β,β-trimethyl-L-phenylalanyl-N¹-[(1S,2E,4R)-4-hydroxy-1-isopropyl-3-methyl-4-phenylbut-2-enyl}-N-1,3-dimethyl-L-valinamide, N, β,β-trimethyl-L-phenylalanyl-N¹[(1S,2E,4S)-4-hydroxy-1-isopropyl-3-methyl-4-phenylbut-2-enyl}-N-1,3-dimethyl-L-valinamide, N, β,β-trimethyl-L-phenylalanyl-N¹[(1S,2E)-4-hydroxy-1-isopropyl-3-methyl-4-(1,3-thiazol-2-yl)but-2-enyl]-N-1-,3-dimethyl-L-valinamide, N, β,β-trimethyl-L-phenylalanyl-N¹-[(1S,2E)-4-hydroxy-1-isopropyl-3-methylpent-2-enyl]-N-1,3-dimethyl-L-valinamide, 6-{[3,3-Dimethyl-2-(3-methyl-2-methylamino-3-phenyl-butyrylamino)-butyryl]-methyl-amino}-2,4,7-trimethyl-octa-2,4-dienoic acid, N, β,β-trimethyl-L-phenylalanyl-N¹-[(1S,2E)-1-isopropyl-3-methyl-4-oxo-4-phenylbut-2-enyl]-N-1,3-dimethyl-L-valinamide, (2S)-N-[(1S,2E)-4-hydroxy-1-isopropyl-3-methyl-2-butenyl]-N,3,3-trimethyl-2-{[(S)-3-methyl-2-(methylamino)-3-phenylbutanoyl]amino}butanamide, N, β,β-trimethyl-L-phenylalanyl-N¹-[(1S,2E)-1-isopropyl-3-methyl-4-oxo-2-butenyl]-N¹,3-dimethyl-L-valinamide, 4-(dimethylsulfonio)-N, β,β-trimethyl-L-phenylalanyl-N¹-[(1S,2E)-1-isopropyl-3-methyl-4-oxo-2-butenyl]-N¹,3-dimethyl-L-valinamide trifluoroacetic acid, N, β,β-trimethyl-L-phenylalanyl-N¹-[(1S,2E)-1-isopropyl-3-methyl-4-oxo-2-pentenyl]-N¹,3-dimethyl-L-valinamide, N, β,β-trimethyl-L-phenylalanyl-N¹-{(1S)-1-[(Z)-(2,5-dioxo-4-imidazolidinylidene)methyl]-2-methylpropyl}-N¹,3-dimethyl-L-valinamide, (2S)-N-[(1S,2E)-1-isopropyl-3-(1H-tetraazol-5-yl)-2-propenyl]-N,3,3-trimethyl-2-{[(2S)- 3-methyl-2-(methylamino)-3-phenylbutanoyl]amino}butanamide, (2E,4S)-2,5-dimethyl-4-(methyl{3-methyl-N-[(2S)-3-methyl-2-(methylamino)-3-phenylbutyl]-L-valyl}amino)-2-hexenoic acid, (2S)-N-[(1S,2E)-4-(1H-imidazol-2-yl)-1-isopropyl-3-methyl-4-oxobut-2-enyl]- N,3,3-trimethyl-2-{[(2S)-3-methyl-2-(methylamino)-3-phenylbutanoyl]amino}butanamide, N, β,β-trimethyl-L-phenylalanyl-N¹,3-dimethyl-N¹-{(1S)-2-methyl-1-[(Z)-(3-methyl-2,5-dioxoimidazolidin-4-ylidene)methyl]propyl}-L-valinamide, N-{1-[(5-Hydroxy-1-isopropyl-3-methyl-4-oxo-pent-2-enyl)-methyl-carbamoyl]-2,2-dimethyl-propyl}-3-methyl-2-methylamino-3-phenyl-butyramide, Ethyl (E,4S)-4-[((2S)-2-{[(2S)-2,3-dimethyl-3-phenylbutanoyl]amino}-3,3-dimethylbutanoyl)(methyl)amino]-2,5-dimethyl-2-hexenoate, (E,4S)-4-[((2S)-2-{[(2S)-2,3-dimethyl-3-phenylbutanoyl]amino}-3,3-dimethylbutanoyl)(methyl)amino]-2,5-dimethyl-2-hexenoic acid, Ethyl (E,4S)-4-[((2S)-2-{[(2S)-2-azido-3-methyl-3-phenylbutanoyl]amino}-3,3-dimethylbutanoyl)(methyl)amino]-2,5-dimethyl-2-hexenoate, Ethyl (E,4S)-4-[((2S)-2-{[(2R)-2-azido-3-methyl-3-phenylbutanoyl]amino}-3,3-dimethylbutanoyl)(methyl)amino]-2,5-dimethyl-2-hexenoate, Ethyl (E,4S)-4-[((2S)-2-{[(2S)-2-azido-3-methyl-3-phenylbutanoyl]amino}-3,3-dimethylbutanoyl)(methyl)amino]-2,5-dimethyl-2-hexenoate, Ethyl (E,4S)-4-[((2S)-2-{[(2R)-2-azido-3-methyl-3-phenylbutanoyl]amino}-3,3-dimethylbutanoyl)(methyl)amino]-2,5-dimethyl-2-hexenoate, Ethyl (E,4S)-4-[((2S)-3,3-dimethyl-2-{[3-methyl-2-(benzyl)-3-phenylbutanoyl]amino}butanoyl)(methyl)amino]-2,5-dimethyl-2-hexenoate, (E,4S)-4-[((2S)-3,3-dimethyl-2-{[3-methyl-2-benzyl-3-phenylbutanoyl]amino}butanoyl)(methyl)amino]-2,5-dimethyl-2-hexenoic acid, Ethyl (E,4S)-4-[((2S)-3,3-dimethyl-2-{[3-methyl-2-allyl-3-phenylbutanoyl]amino}butanoyl)(methyl)amino]-2,5-dimethyl-2-hexenoate, (E,4S)-4-[((2S)-3,3-dimethyl-2-{[3-methyl-2-allyl-3-phenylbutanoyl]amino}butanoyl)(methyl)amino]-2,5-dimethyl-2-hexenoic acid, Ethyl (E,4S)-4-[((2S)-3,3-dimethyl-2-{[3-methyl-2-ethyl-3-phenylbutanoyl]amino}butanoyl)(methyl)amino]-2,5-dimethyl-2-hexenoate, (E,4S)-4-[((2S)-3,3-dimethyl-2-{[3-methyl-2-ethyl-3-phenylbutanoyl]amino}butanoyl)(methyl)amino]-2,5-dimethyl-2-hexenoic acid, Ethyl (E,4S)-4-[((2S)-3,3-dimethyl-2-{[3-methyl-2-methylsulfanyl-3-phenylbutanoyl]amino}butanoyl)(methyl)amino]-2,5-dimethyl-2-hexenoate, (E,4S)-4-[((2S)-3,3-dimethyl-2-{[3-methyl-2-methylsulfanyl-3-phenylbutanoyl]amino}butanoyl)(methyl)amino]-2,5-dimethyl-2-hexenoic acid, (E,4S)-4-[((2S)-3,3-dimethyl-2-{[3-methyl-2-methylsulfonyl-3-phenylbutanoyl]amino}butanoyl)(methyl)amino]-2,5-dimethyl-2-hexenoic acid, Ethyl (E,4S)-4-[{(2S)-2-[(2-methoxy-3-methyl-3-phenylbutanoyl)amino]-3,3-dimethylbutanoyl}(methyl)amino]-2,5-dimethyl-2-hexenoate, (E,4S)-4-[{N-[(2S)-2-methoxy-3-methyl-3-phenylbutanoyl]-3-methyl-L-valyl}(methyl)amino]-2,5-dimethyl-2-hexenoic acid, (E,4S)-4-[{N-[(2R)-2-methoxy-3-methyl-3-phenylbutanoyl]-3-methyl-L-valyl}(methyl)amino]-2,5-dimethyl-2-hexenoic acid, (E,4S)-4-[{N-[(2S)-2-hydroxy-3-methyl-3-phenylbutanoyl]-3-methyl-L-valyl}(methyl)amino]-2,5-dimethyl-2-hexenoic acid, (E,4S)-4-[{N-[(2R)-2-hydroxy-3-methyl-3-phenylbutanoyl]-3-methyl-L-valyl}(methyl)amino]-2,5-dimethyl-2-hexenoic acid and (2S)-N-[(1S,2E)-4-hydrazino-1-isopropyl-3-methyl-4-oxo-2-butenyl]-N,3,3-trimethyl-2-{[(2S)-3-methyl-2-(methylamino)-3-phenylbutanoyl]amino}butanamide.

DETAILED DESCRIPTION OF THE INVENTION

Compounds of this invention may be prepared as outlined in the following schemes.

As described in Scheme 1, 2-oxopropanoic acid 1 is reacted with methyl iodide in a solvent mixture of aqueous sodium hydroxide-tetrahydrofuran (THF) to afford pyruvic acid 2 which is further converted to acid 3 by sequential treatment with trimethylsilyldiazomethane (TMSCHN$_2$), sodium borohydride(NaBH$_4$) and lithium hydroxide.

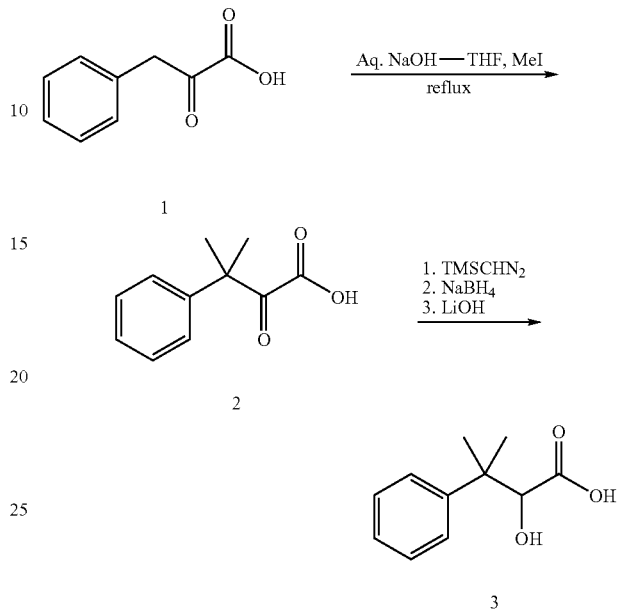

As further described in Scheme 2, ester 4 is reacted with methyl iodide in the presence of silver oxide in ether to give ether 5 which is then hydrolyzed with lithium hydroxide in a solvent mixture of THF-methyl alcohol-water to give propionic acid 6.

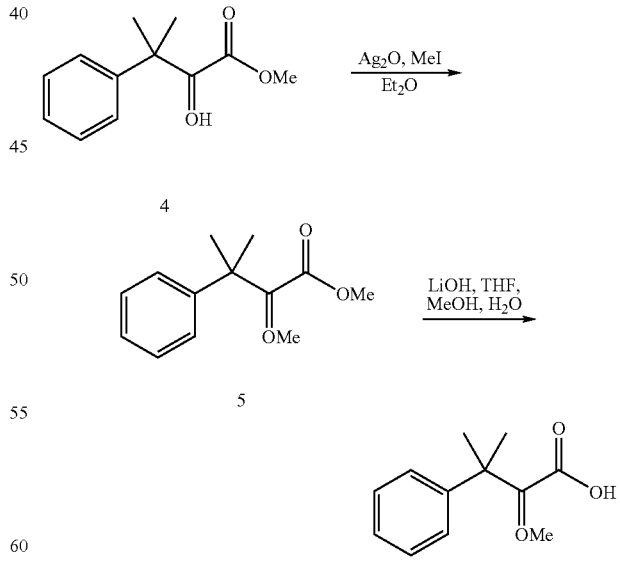

Described in Scheme 3, reaction of propionic acid 7 with 1.1 equivalent of disulfide RSSR in the presence of lithium diisopropylamide (LDA) and 1,3-dimethyl-3,4,5,6-tetrahydro-2(1H)-pyrimidinone (DMPU) affords sulfide 8 which is further oxidized with peroxyacetic acid to give sulfone 9.

Scheme 3

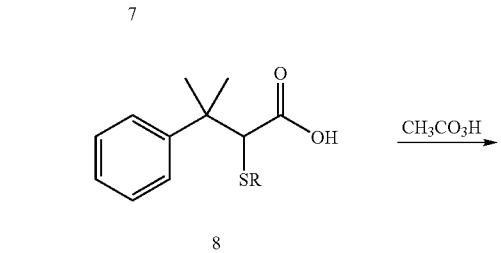

According to Scheme 4, alkylation of amide 10 with R₂X, where non-limiting examples include methyl, benzyl, allyl (CH₂=CH—CH₂—) and azido, in the presence of sodium or potassium 1,1,1,3,3,3-hexamethyldisilazane (Na(K)HMDS) gives alkylated product 11. Reaction of alkylated product 11 with lithium peroxide affords propionic acid 12.

Scheme 4

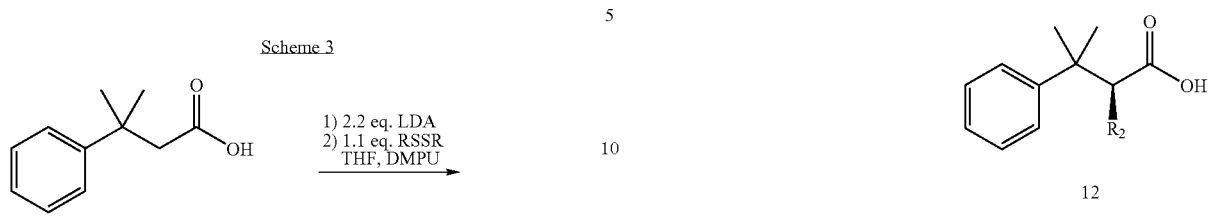

As described in Scheme 5, tetralone 13 is reacted with isonitrile 14 in the presence of potassium tert-butoxide to give ester 15 which is further reacted with hydrochloric acid then alkylated with methyl iodide in the presence of sodium hydroxide and hydrolyzed with sodium hydroxide to give carboxylic acid 16. Carboxylic acid 16 is reacted with methylamine in the presence of borane-pyridine complex to give amine 17.

Scheme 5

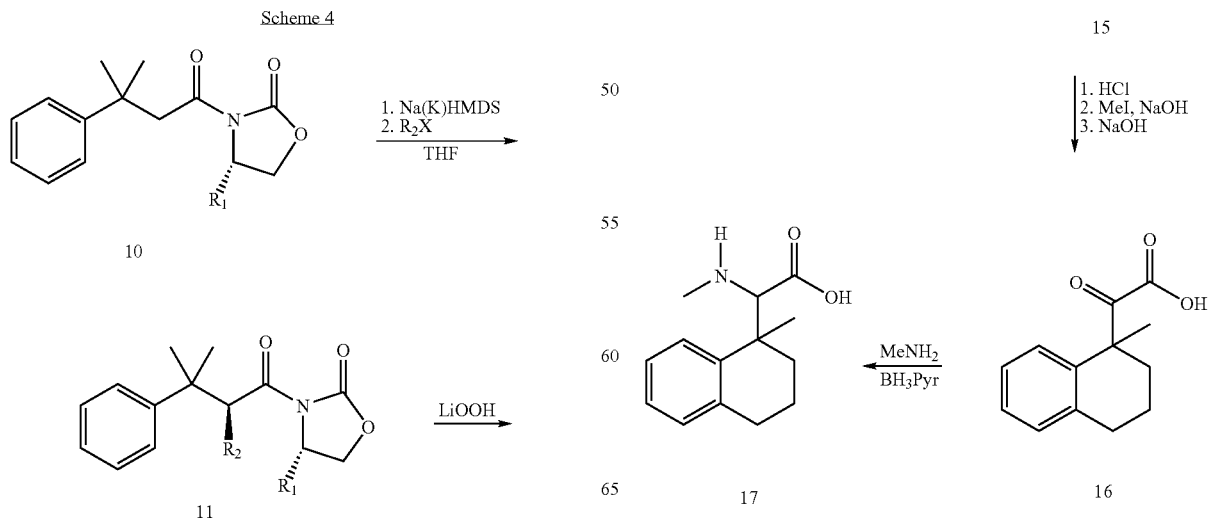

According to Scheme 6, reaction of carboxylic acid 18 with methylamine affords substituted-amino acid 19.

Scheme 6

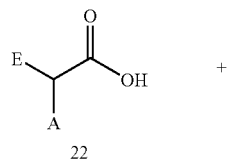

18    19

According to Scheme 7, reaction of carboxylic acid 20 with formic acid and formalin affords substituted amine 21.

Scheme 7

20    21

Described in Scheme 8, reaction of carboxylic acid 22 where E and A are hereinbefore defined with amine 23 in the presence of a coupling agent selected from 1-(3-dimethylaminopropyl)-3-ethylcarbodiimide hydrochloride (EDC) or benzotriazole-1-yl-oxy-tris-pyrrolidinophosphonium hexafluorophosphate (PyBOP) gives carboxylic acid 24.

Scheme 8

22

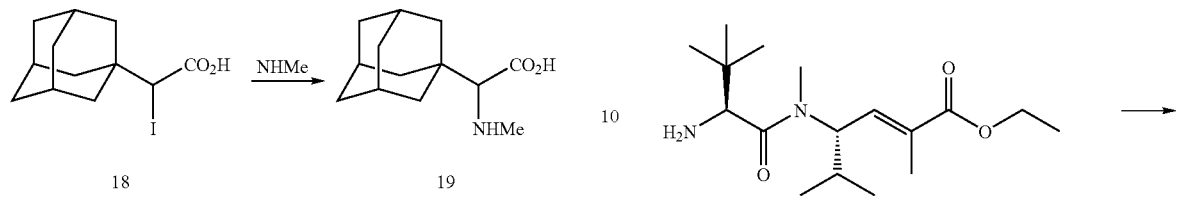

23

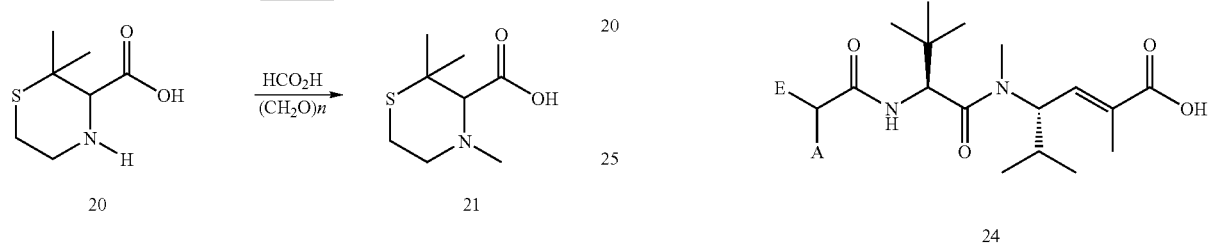

24

As described in Scheme 9, reaction of carboxylic acid 25 with an amine NHRR in the presence of a coupling agent selected from 1-(3-dimethylaminopropyl)-3-ethylcarbodiimide hydrochloride (EDC) or benzotriazole-1-yl-oxy-tris-pyrrolidinophosphonium hexafluorophosphate (PyBOP) affords amide 26. Further, reaction of carboxylic acid 25 with an alcohol ROH in the presence of a coupling agent selected from 1-(3-dimethylaminopropyl)-3-ethylcarbodiimide hydrochloride (EDC) or benzotriazole-1-yl-oxy-tris-pyrrolidinophosphonium hexafluorophosphate (PyBOP) affords ester 27.

Scheme 9

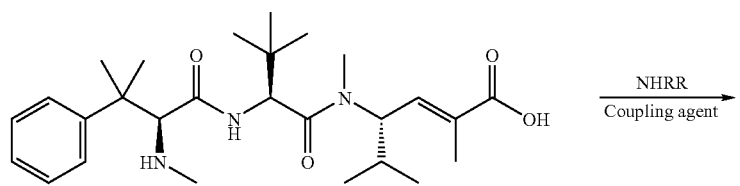

25

-continued

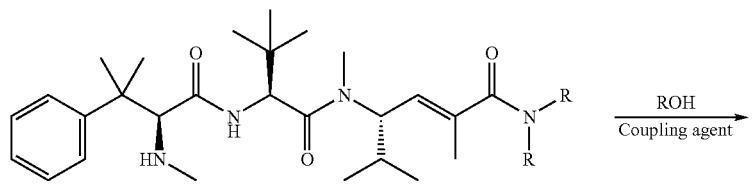

26

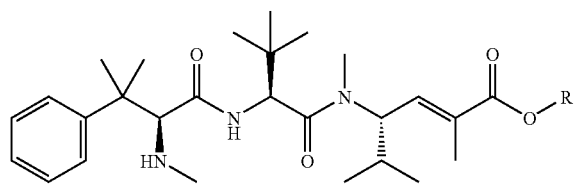

27

Described in Scheme 10, is the reaction of aldehyde 28 with (carboethoxyethylidene)triphenylphosphorane followed by reaction with lithium hydroxide to give carboxylic acid 29.

As described in Scheme 11, reaction of carboxylic 30 with N-methyl-N-methoxyamine in the presence of a coupling agent selected from 1-(3-dimethylaminopropyl)-3-ethylcarbodiimide hydrochloride (EDC) or benzotriazole-1-yl-oxy-tris-pyrrolidinophosphonium hexafluorophosphate (PyBOP) affords amide 31 which is reduced with lithium aluminum hydride (LAH) to give aldehyde 33. Reaction of amide 31 with RM, where M is a metal such as lithium, potassium, sodium or magnesium affords ketone 32. Further reaction of ketone 32 with a hydride reducing agent selected from LAH or sodium borohydride gives alcohol 34 which may also be prepared by reaction of aldehyde 33 with RM. Reaction of acid 35 with 1-(3-dimethylaminopropyl)-3-ethylcarbodiimide hydrochloride (EDC) followed by treatment with sodium borohydride gives alcohol 36 which can be oxidized to aldehyde 33 by treatment with dimethylsulfoxide/oxalyl chloride or manganese dioxide.

Scheme 10

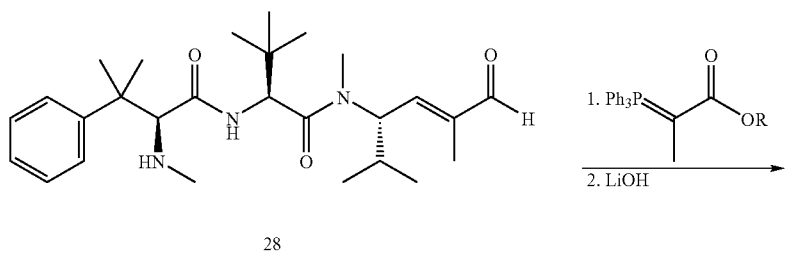

28

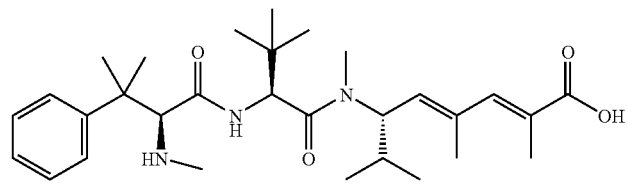

29

Scheme 11

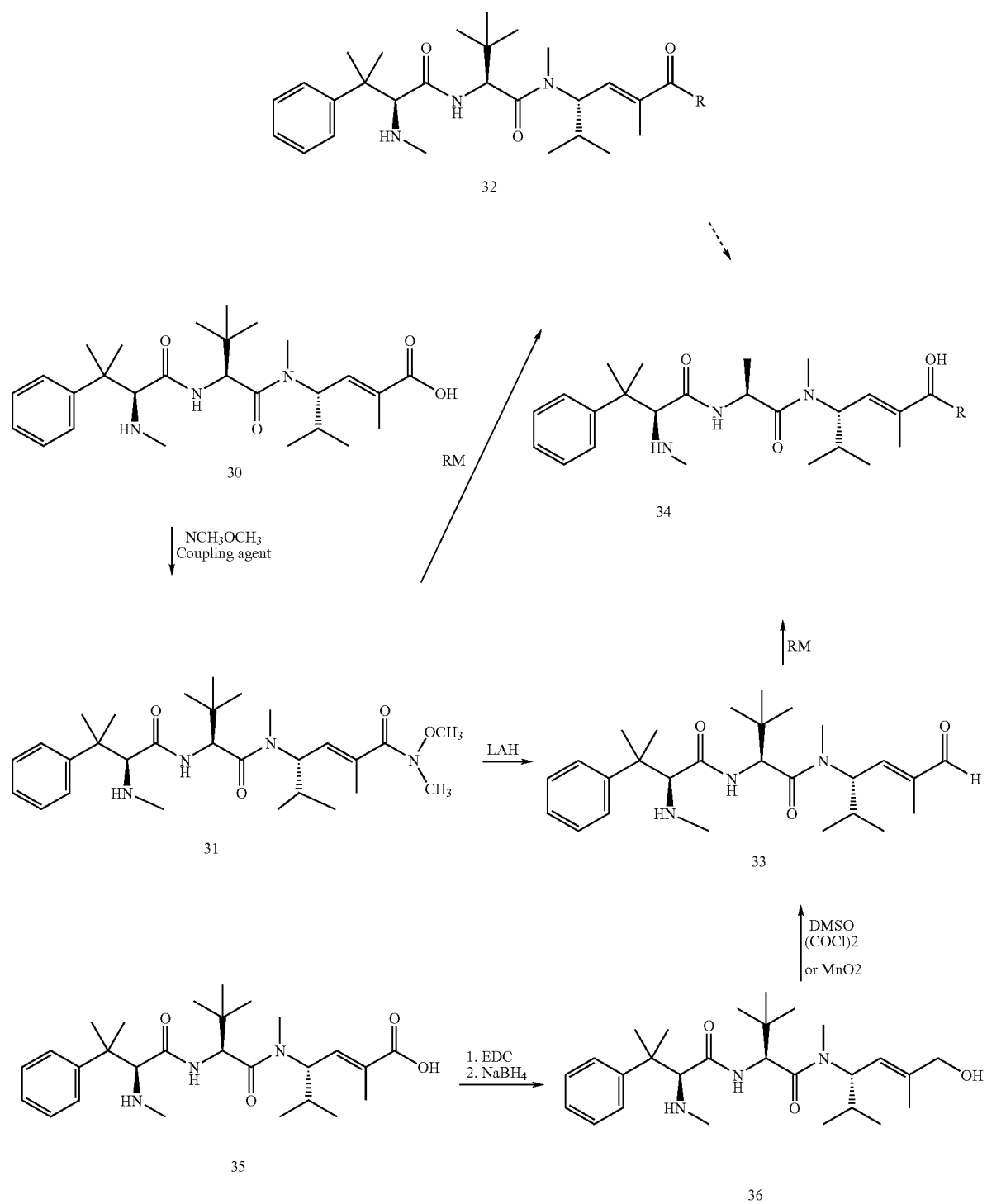

As described in Scheme 12, carboxylic acid is ozonized in methyl alcohol followed by treatment with dimethylsulfide to give in situ aldehyde 37. A 1,1-bisphosphonate ester 38 is treated with n-butyllithium followed by aldehyde 37 to give phosphonate 39 which is further reacted with trimethylsilyl- bromide to give phosphonate 40. A phosphorylmethylene-sulfonate 41 is treated with n-butyl lithium followed by aldehyde 37 to afford sulfonate ester 42 which is reacted with tetrabutylammonium iodide to give sulfonic acid 43. Additionally, treating aldehyde 37 with phosphonate 44 affords hydantoin 45.

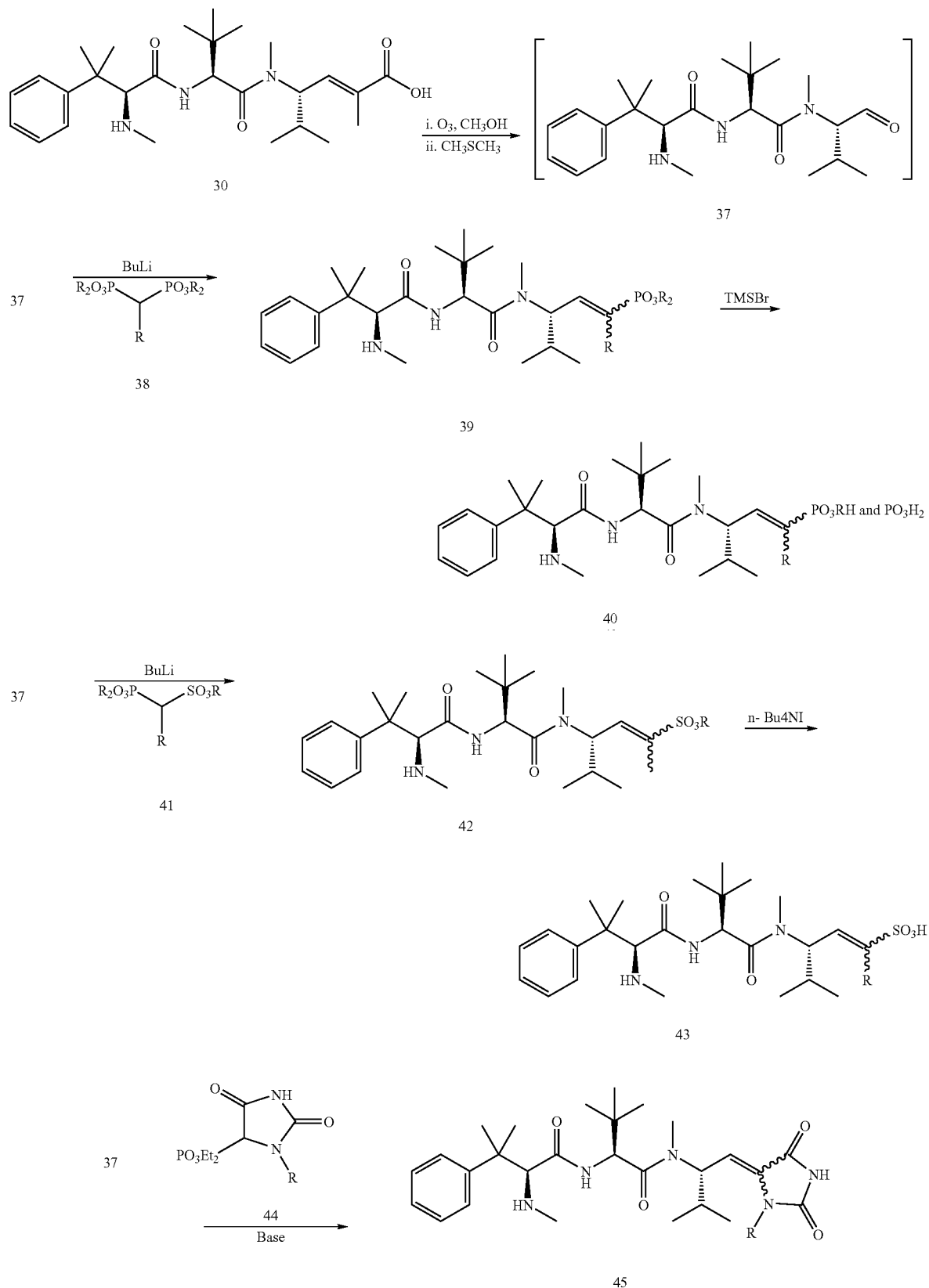

As described in Scheme 13, amide 31 is reacted with 47 (the lithium salt of trimethylsilyl ether 46) (which is prepared by reaction of tributyltin reagent 46 with n-butyl lithium) to give ester 48 which is then treated with trifluoroacetic acid (TFA) to give carboxylic acid 49.

hexafluorophosphate (PyBOP) affords nitrile 55. Treatment of nitrile 55 with trifluoroacetic acid (TFA) gives amine 56. Treatment of amine 56 with carboxylic acid 57 in the presence of O-(7-azabenzotriazol-1-yl)-N,N,N',N'-tetramethylu-

Scheme 13

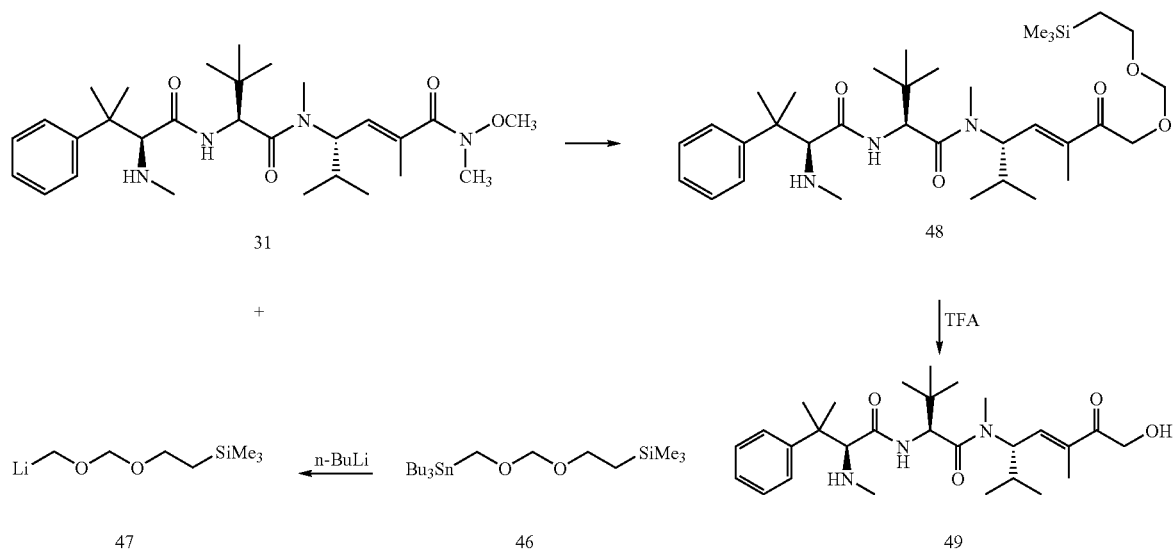

Described in Scheme 14, aldehyde 50 is reacted with (triphenylphosphoranylidene)acetonitrile 51 to give nitrile 52 which is treated with trifluoroacetic acid (TFA) to give amine 53. Reaction of 53 with carboxylic acid 54 in the presence of benzotriazole-1-yl-oxy-tris-pyrrolidinophosphonium ronium hexafluorophosphate (HATU), 1-Hydroxy-7-azabenzotriazole (HOAt) and diisopropylethylamine (DIEA) gives nitrile 58 which is further reacted with trimethylsilylazide and dibutyltin oxide followed by trifluoroacetic acid (TFA) to give tetrazole 59.

Scheme 14

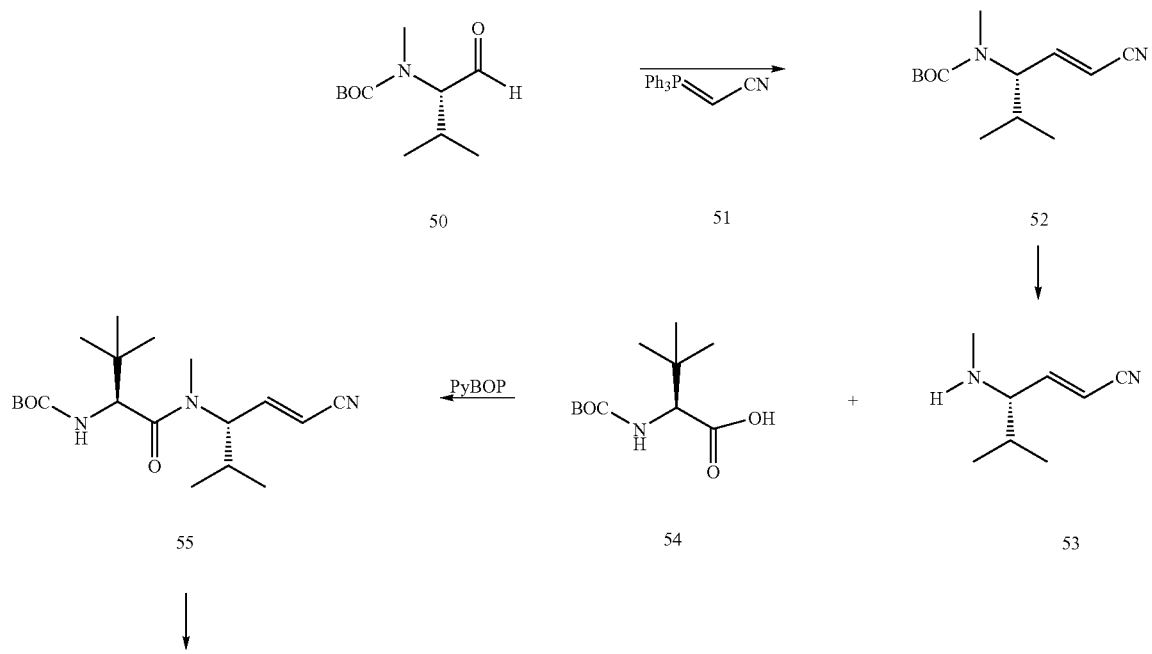

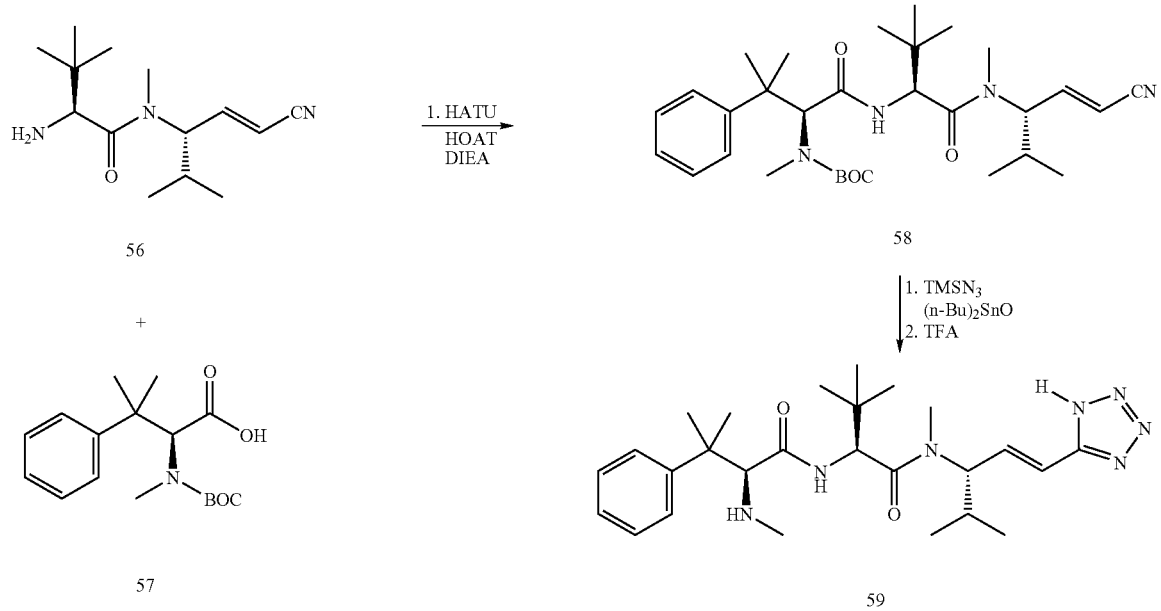

Described in Scheme 15, reaction of carboxylic acid 60 with amine 61 in the presence of 1-(3-dimethylaminopropyl)-3-ethylcarbodiimide hydrochloride (EDC) followed by treatment with trifluoroacetic acid (TFA) affords amine 62 which is reacted with carboxylic acid 63 in the presence of benzotriazole-1-yl-oxy-tris-pyrrolidinophosphonium hexafluorophosphate (PyBOP) followed by treatment with trifluoroacetic acid to give amine 64. Further reaction of amine 64 with carboxylic acid 65 in the presence of 1-(3-dimethylaminopropyl)-3-ethylcarbodiimide hydrochloride (EDC) followed by treatment with trifluoroacetic acid (TFA) affords proline derivative 66.

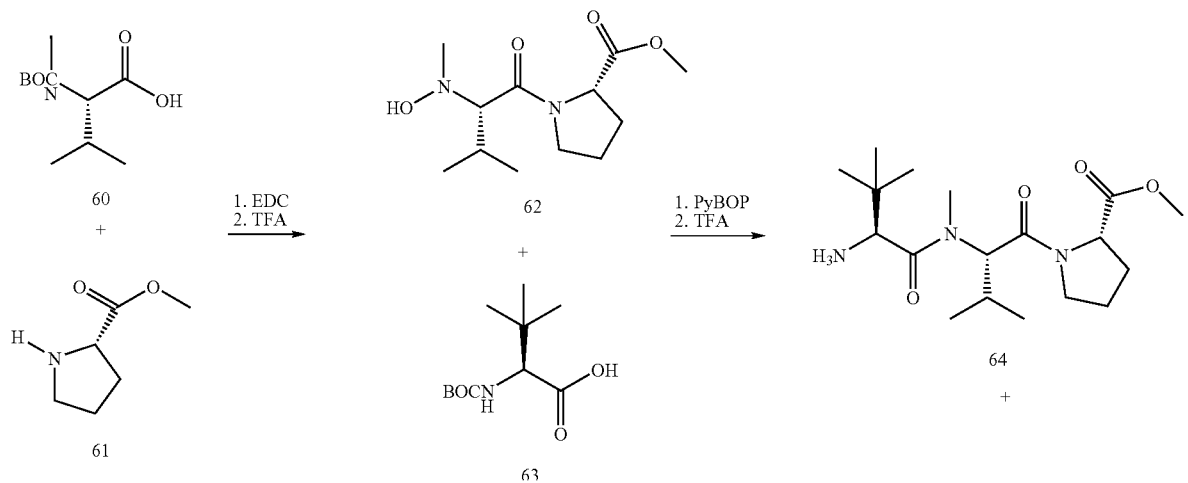

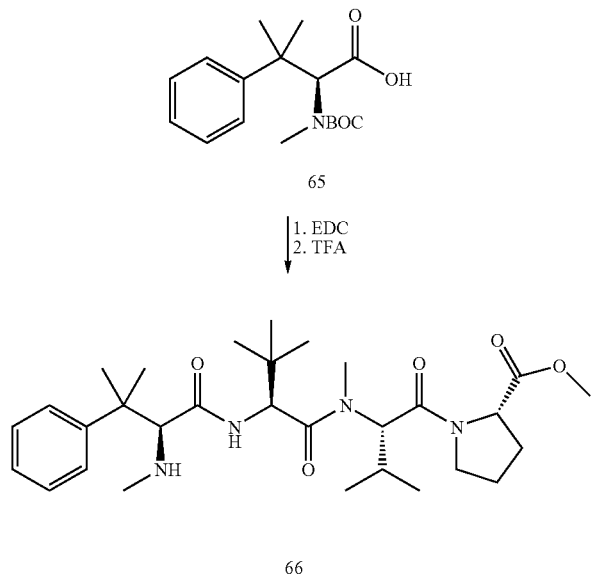

According to Scheme 16, imidazole 67 is reacted with chloromethyl ethyl ether in the presence of sodium hydride to give ether 68 which is reacted with n-butyllithium to afford lithium salt 69. Reaction of ester 70 with lithium hydroxide followed by treatment with N,O-dimethylhydroxylamine in the presence of 1-(3-dimethylaminopropyl)-3-ethylcarbodiimide hydrochloride (EDC) affords amide 71 which is reacted with lithium salt 69 to give imidazole 72. Acid hydrolysis of imidazole 72 with HCl affords amine 73. Further reaction of amine 73 with carboxylic acid 60 in the presence of 3-(diethoxyphosphoryloxy)-1,2,3-benzotriazin-4(3H)-one (DEPBT) gives imidazole 74 which is further reacted with amino acid 75 in the presence of DEPBT followed by treatment with trifluoroacetic acid to give imidazole 76.

Scheme 16

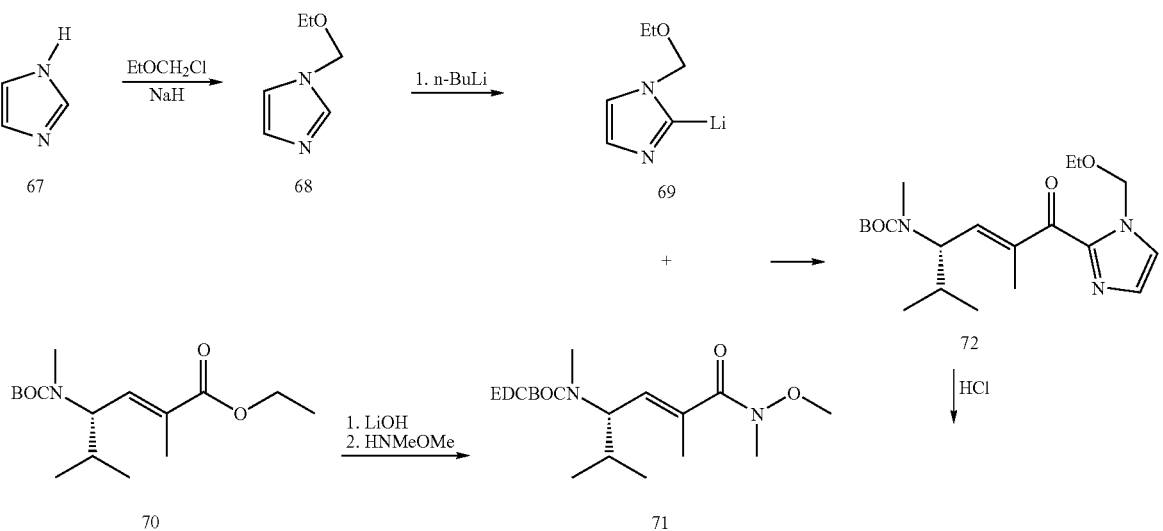

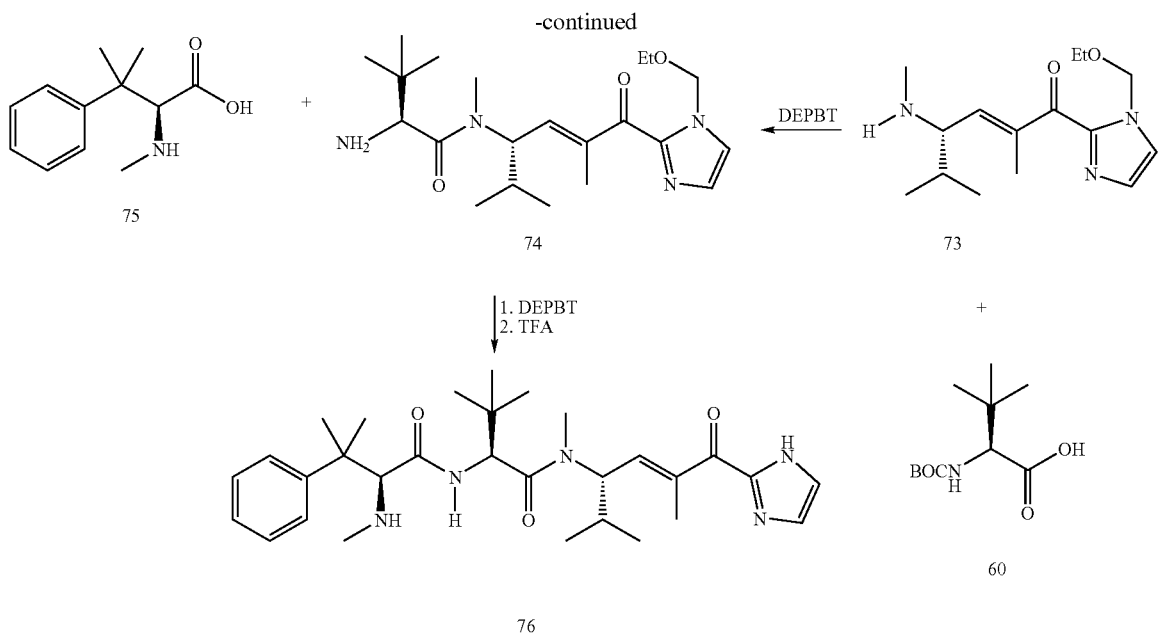

As described in Scheme 17, reaction of carboxylic acid 57 with morpholine in the presence of benzotriazole-1-yl-oxy-tris-pyrrolidinophosphonium hexafluorophosphate (PyBOP) affords amide 77 which is reduced with lithium aluminum hydride to give aldehyde 78 which is coupled with amine 79 by reductive alkylation in the presence of zinc chloride and sodium cyanoborohydride followed by sequential treatment with lithium hydroxide (LiOH) and hydrochloric acid (HCl) acid to give 80.

Scheme 17

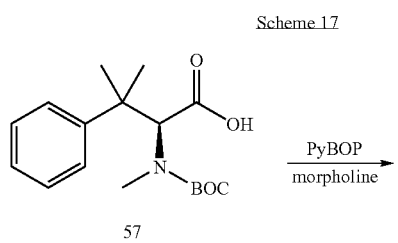

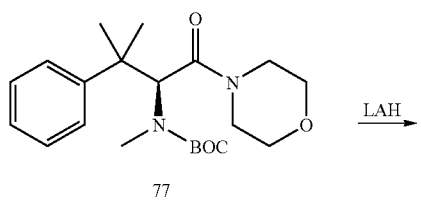

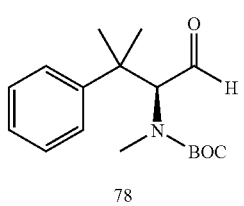

78 +

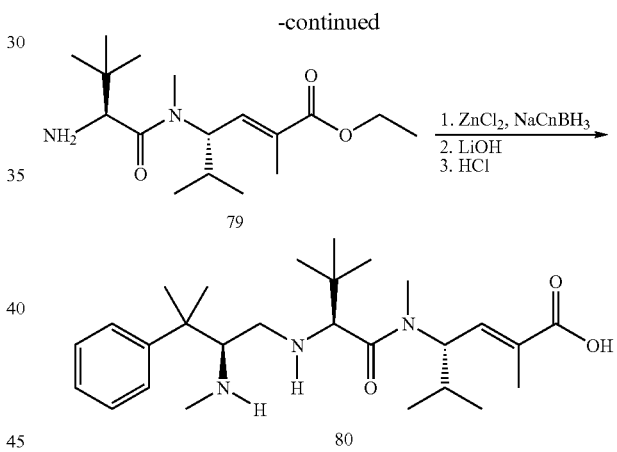

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

According to a further aspect of the present invention there is provided a series of compounds of formula (I) or the pharmaceutically acceptable salts thereof as hereinbefore defined for use in a method of treatment of human or animal disease.

In particular, compounds of the invention are useful for the treatment of cancer and cancerous tumors.

Further, compounds of the present invention inhibit tubulin polymerization and are therefore are useful in the treatment of cancer.

In particular, the present invention relates to a method of treating or inhibiting the growth of cancerous tumors in a mammal with inherent or acquired resistance to chemotherapeutic agents used in chemotherapy treatment and in particular antimitotic agents by administering an effective amount of a compound of formula (I) and pharmaceutically acceptable salts thereof.

Accordingly, it is one of the purposes of this invention to overcome the above described limitations in cancer treatment by providing a method for treating tumors that are resistant to currently marketed antimitotic agents.

Further, compounds of the invention provide a method for the treatment or prevention of cancerous tumors that express multiple drug resistance (MDR) or are resistant because of MDR in a mammal in need thereof.

Additionally, the present invention provides a method of treating, inhibiting the growth of, or eradicating a tumor in a mammal in need thereof wherein said tumor is resistant to at least one chemotherapeutic agent which method comprises providing to said mammal an effective amount of a compound of Formula (I).

Cytotoxicity Standard Pharmacological Test Procedures

Tubulin Polymerization Assays. For in vitro tubulin polymerization assays, bovine microtubule-associated protein (MAP)-rich tubulin, PEM buffer [80 mM Na-PIPES (pH 6.9), 1 mM $MgCl_2$, and 1 mM EGTA], and GTP are purchased from Cytoskeleton (Denver, Colo.). MAP-rich tubulin (final concentration 1.5 mg/ml) is dissolved in cold PEM buffer containing 1 mM GTP (GPEM) and centrifuged at 12,000×g for 10 min at 4° C. The tubulin solution (100 μl/well) is added rapidly to wells of a low-volume, 96-well plate already containing duplicate aliquots (10 μl) of test compounds in GPEM. Final compound concentrations are 0.1 or 1 μM. Control wells contained the same final concentration of DMSO (0.3%). After initiation of the reaction, absorbance at 340 nm is measured every minute for 60 min at 24° C. using a SpectraMax Plus plate reader (Molecular Devices, Sunnyvale, Calif.). The resultant data is displayed in Table 1.

Biological Testing Results

TABLE 1

| Ex. No. | KB* | KB85* | KBV1* | Colo205* | Tubulin Polym.** |
|---|---|---|---|---|---|
| 1 | 19.5 | 56 | 1514 | | 79 |
| 2 | 34 | 62 | 162 | | 37 |
| 3 | 70(2) | 176(2) | 1758(2) | | 51 |
| 4 | 375 | 536 | 42% | | 61 |
| 5 | 207 | 459 | 40% | | 57 |
| 6 | 64(2) | 123(2) | 33%(2) | | 64 |
| 7 | 47 | 68 | 2188 | | 32 |
| 8 | 35 | 56 | 1622 | | 68 |
| 9 | 1.4(3) | 23(3) | 21% | | 56 |
| 10 | 1.5(2) | 19.7(2) | 2138(2) | | 42 |
| 11 | 0.56 | 24 | 8% | | 41 |
| 12 | 48 | 65 | 1334 | | 51 |
| 13 | 172(2) | 352(2) | 1771(2) | | 11 |
| 14 | 45 | 135 | 1647 | | 51(5) |
| 15 | 7.2 | 18 | 354 | | 77 |
| 16 | 39 | 60 | 803 | | 62 |
| 17 | 1.9 | 15 | 363 | | 71 |
| 18 | 74 | 519 | 6% | | 76 |
| 19 | 5.9 | 50 | 1552 | | 66 |
| 20 | 82 | 664 | 3% | | 80 |
| 21 | 1.6 | 6.2 | 275 | | 89 |
| 22 | 70 | 599 | 12% | | 95 |
| 23 | 2.5 | 6.2 | 362 | | 88 |
| 24 | 62 | 180 | 17% | | 94 |
| 25 | 39(2) | 227(2) | 7% | 20 | 75 |
| 26 | 33(2) | 60(2) | 2326(2) | | 71(2) |
| 27 | 43.5(6) | 73.5(6) | 1301(6) | 23 | 69 |
| 28 | 1.07(3) | 21.9(3) | 14%(3) | 0.25 | 56(3) |
| 29 | 0.75(2) | 4.1(2) | 180(2) | | 62 |
| 30 | 3.3(2) | 6(2) | 96(2) | | 45 |
| 31 | 0.9 | 5.1 | 191 | | 69 |
| 32 | 12 | 45 | 636 | | 99(2) |
| 33 | 18 | 53 | 1533 | | 19 |
| 34 | 0.25(2) | 4.2(2) | 5%/1948 | | 64 |
| 35 | 1.5(3) | 7.3(3) | 291(3) | | 82 |
| 36 | 62 | 205 | 0% | | 97 |
| 37 | 6.4 | 21 | 1643 | | 86 |
| 38 | 20 | 529 | 0% | | 75 |
| 39 | 15(2) | 22(2) | 366(2) | | 29 |
| 40 | 3.5 | 116 | 4% | | 93*** |
| 41 | 16 | 51 | 1099 | | 96 |
| 42 | 184 | 1850 | 0% | | 96 |

TABLE 1-continued

| Ex. No. | KB* | KB85* | KBV1* | Colo205* | Tubulin Polym.** |
|---|---|---|---|---|---|
| 43 | 515 | 1577 | 0% | | 91 |
| 44 | 1.5 | 6.2 | 475 | | 83 |
| 45 | 3.7 | 16 | 493 | | 62(2) |
| 46 | 450 | 1719 | 1% | | 99 |
| 47 | 3.5 | 17 | 272 | | 88(2) |
| 48 | 58 | 184 | 15% | | 91(2) |
| 49 | 5.2 | 17 | 150 | | 62(2) |
| 50 | 64 | 270 | 9% | | 84(2) |
| 51 | 22 | 61 | 1772 | | 82 |
| 52 | 11 | 47 | 392 | | 86 |
| 53 | 667 | 1675 | 29% | | 11 |
| 54 | 136 | 846 | 8% | | 55 |
| 55 | 603 | 646 | 13% | | 66 |
| 56 | 468 | 575 | 11% | | |
| 57 | 1756(2) | 2610(2) | 7%(2) | | 75 |
| 58 | 427 | 550 | 15% | | 89(2) |
| 59 | 5.5 | 6.6 | 76 | | 93 |
| 60 | 9.1 | 17 | 427 | | 94 |
| 61 | 151 | 293 | >3000 | | 40*** |
| 62 | 2952(2) | 26%(2) | 10%(2) | | 65(2) |
| 63 | 1% | 0% | 0% | | 42 |
| 64 | 2% | 1% | 0% | | 86 |
| 65 | 11% | 1% | 0% | | 44 |
| 66 | 25% | 0% | 0% | | 91 |
| 67 | 0% | 0% | 0% | | 21 |
| 68 | 1976(2) | 2077(2) | 8%(2) | | 45 |
| 69 | 0% | 0% | 3% | | 59 |
| 70 | 0% | 0% | 3% | | 69 |
| 71 | 1304 | 1751 | 0% | | 64 |
| 72 | 0% | 0% | 4% | | 53 |
| 73 | 582 | 565 | 1787 | | 33 |
| 74 | 19 | 54 | 466 | | 73 |
| 75 | 124 | 186 | 632 | | 83*** |
| 76 | 16 | 22 | 190 | | 63*** |
| 77 | 13 | 19 | 364 | | 97 |
| 78 | 63 | 172 | 1455 | | 75 |
| 79 | 27 | 53 | 1582 | | 90*** |
| 80 | 725 | 1326 | 1805 | | 70 |
| 81 | 454(2) | 447(2) | 1594(2) | | 71 |
| 82 | 713(6) | 1330(6) | 1938 > 3000(6) | 5.1(16) | 51/47 |
| 83 | 124/>3000 | 215/>3000 | 2398 > 3000 | 46 | 0 |
| 84 | 403(2) | 664(2) | 2358(2) | 180 | 69 |
| 85 | 1072 | 1738 | 10% | | 59 |
| 86 | 1148 | 1819 | 5% | 71/71 | 31 |
| 87 | 104(2) | 312(2) | 14%(2) | | 28 |
| 88 | 218 | 1364 | 0% | | 91 |
| 89 | 5.1 | 9.9 | 230 | | 95 |
| 90 | 43 | 68 | 1134 | | 76*** |
| 91 | 21% | >3000 | >3000 | >1000 | 84**** |
| 92 | 861(2) | 990(2) | 30% | 53/210 | 94 |
| 93 | 2511 | 30% | 30% | | — |
| 94 | 1297(2) | 1332(2) | 30%(2) | 460 | 73 |
| 95 | 575 | 756 | 15% | >1000 | — |
| 96 | 846(3) | 1122(3) | 11%(2)/2630 | 340 | 46 |
| 97 | 1910 | 3320 | 17%@6000 | >1000 | — |
| 98 | 1151 | 1205 | 42%@6000 | 270 | 63 |
| 99 | 3476 | 3638 | 16%@6000 | >1000 | — |
| 100 | 957 | 1151 | 5260 | 190 | 54 |
| 101 | 1100 | 1824 | 4580 | >1000 | — |
| 102 | 693 | 1151 | 40%@6000 | 280 | 79 |
| 103 | 1749(2) | 1659(2)/30% | 5% | 760 | 80 |
| 104 | 1731/3000 | 2126/3000 | 2398/3000 | >1000 | 38 |
| 105 | 43%/2691 | 21%(2) | 0%(2) | 1738(2) | 64 |
| 106 | 1416 | 1229 | 22% | 930 | 54 |
| 107 | >3000 | >3000 | >3000 | >1000 | 21 |
| 108 | >3000 | >3000 | >3000 | >1000 | 21 |
| 109 | 65(4) | 227(4) | 2077(3)/23% | | |

TABLE 1-continued

| Ex. No. | KB* | KB85* | KBV1* | Colo205* | Tubulin Polym.** |
|---|---|---|---|---|---|
| 110 | 173/2512/ 2630/7% @3000/5% @3000 | 263/26%/ 22%/10% @3000/0% @3000 | 22%/23% %/24%@ 3000/4% @3000 | >1000 | 19 |

Data is the average of the number of determinations in parenthesis.
*IC50 in nM or % inhibition @ 3000 nM
**% inhibition at 0.3 uM
***% inhibition at 0.5 uM
****% inhibition at 2 uM Cell Survival Assay: Standard Pharmacological Test Procedure. The concentration of candidate inhibitor required to inhibit 50% of cell growth ($IC_{50}$) is done according to previously reported methods. (Discafani, C. M., Carroll, M. L., Floyd Jr., M. B. F., Hollander, I. J., Husain, Z., Johnson, B. D., Kitchen, D., May, M. K., Malo, M. S., Minnick Jr., A. A., Nilakantan, R., Shen, R., Wang Y-F., Wissner, A., Greenberger, L. M. Irreversible inhibition of epidermal growth factor receptor tyrosine kinase with in vivo activity by N-[4-[3-bromophenyl)amino]-6-quinaxolinyl]-2-butynamide (CL-387,785), Biochem. Pharmacol. 57: 917-925,1999) Briefly, cells are plated in 100 μl of media in the morning of day 1 and allowed to adhere to the plates for 2-6 hr. Compounds are serially diluted into media as 2x stocks and 100 μl added to cells in duplicate. Compounds are incubated with cells for 3 days. At the end of the incubation period the sulforhodamine B (SRB) assay, which measures protein content as an assessment of cell survival, is performed as described previously (Skehan P, Storeng R, Scudiero D, Monks A, McMahon J, Vistica D, Warren JT, Bokesch H, Kenney S, Boyd MR. New colorimetric cytotoxicity assay for anticancer-drug screening. J Natl Cancer Inst 1990 Jul. 4;82(13):1107-12) with some modification as follows. For KB cells with 20% FCS, media is gently decanted and replaced with 200 μl of serum-free media mixed with cold 50% TCA for a final concentration of 10% TCA. The plates are incubated for 1 hr at 4° C., followed by washing 5 times in cold distilled water, then air dried overnight. The fixed cells are strained for 10 min with 80 μl of 0.04% SRB solution prepared in 1% glacial acetic acid. Stain is discarded and plates washed 5 times in 1% glacial acetic acid, then air-dried until completely dry. Stained cell product is dissolved in 150 μl of 10 mM Trizma Base and placed on a shaker for 20 minutes until fully dissolved. Absorbance is read on a Victor V multi-label plate reader (Perkin Elmer, Gaithersburg, Md.). The resultant data is displayed in Tables 1 and 2.

Results of Standard Pharmacological Test procedure

TABLE 2

| Ex. No. | HCT-15 | LOX | S1-M1 | S1 | A375 | KM20 | NCl-H1299 |
|---|---|---|---|---|---|---|---|
| 92 | 1380 | 1072 | | | | | 1202 |
| 27 | | 26(2) | 50(4) | 336(2) | 657(2) | | 38 |
| 105 | | 1738 | | | | | |
| 82 | 1499(2) | 630(4) | | | 663(4) | 4.6(4) | 1572(6) |
| 84 | 1259 | 550 | | | | | 832 |
| 87 | 759 | 151 | | | | | 295 |
| 26 | | 46 | | | | | |
| 109 | | | | | 19 | | |
| 35 | | | 11 | 9 | | | |
| 110 | 19% | | | | | | |

Data is the average of the number of determinations in parenthesis.
IC50 in nM or % inhibition @ 3000 nM Growth of Tumors in Nude Mice. Drug efficacy studies in mice are performed similar to previously reported studies. (Discafani, C. M., Carroll, M. L., Floyd Jr., M. B. F., Hollander, I. J., Husain, Z., Johnson, B. D., Kitchen, D., May, M. K., Malo, M. S., Minnick Jr., A. A., Nilakantan, R., Shen, R., Wang Y-F., Wissner, A., Greenberger, L. M. Irreversible inhibition of epidermal growth factor receptor tyrosine kinase with in vivo activity by N-[4-[3-bromophenyl)amino]-6-quinaxolinyl]-2-butynamide (CL-387,785), Biochem. Pharmacol. 57: 917-925, 1999) Briefly, athymic nu/nu female mice (Charles River Laboratories) are implanted SC (subcutaneously) with $1.5 \times 10^6$ LOX melanoma cells. When tumors attain a mass of between 80 and 120 mg (day 0), animals are randomized into treatment groups each containing either 5 or 10 animals, (dependent upon the experiment). In some experiments, tumors are allowed to grow up to 2.5 grams in size before drug treatment is initiated. After staging, animals are treated intravenously (IV) with one or more doses of test compound formulated in saline, or vehicle control. The doses chosen for both paclitaxel and vincristine are between 80 and 90% of the maximum tolerated dose for each drug. Tumor mass ([length×Width$^2$]/2) is determined once a week for up to 35 days. The relative tumor growth (mean tumor mass on day measured divided by the mean tumor mass on day zero) and the percent Tumor/Control (%T/C) are then calculated for each treatment group for the duration of each experiment. The %T/C is defined as the Mean Relative Tumor Growth of the Treated Group divided by the Mean Relative Tumor Growth of Vehicle Control Group multiplied by 100. The data are analyzed via a one-sided Student's t-test. A p-value ≦0.05 indicates a statistically significant reduction in relative tumor growth of treated group compared to that of the vehicle control group. The results are displayed in Table 3.

Effect on the Growth of the Human Melanoma Carcinoma Lox in a Xenograft Model

TABLE 3

| Ex. No. | Dose (mg/kg) | Route | % T/C on day 7 | 9 | 10 | 12 | 13 | 14 |
|---|---|---|---|---|---|---|---|---|
| 27 | 10 | IV | 13 | | | | | 2 |
| 27 | 10 | IV | 11 | | | 2 | | |
| 28 | 10 | IV | 10 | | 4 | | | |
| 109 | 3 | IV | 24 | | | | 8 | |
| 35 | 2 | IV | 5 | | | | | 1 |
| 29 | 10 | IV | 14 | 9 | | | | |
| 26 | 15 | IV | 4 | | | | | |
| 30 | 5 | IV | 11 | | | | | 3 |

Groups of 5 female nu/nu mice are injected with $1.5 \times 10^6$ Lox cells. Animals bearing staged tumors are treated IV or IP with vehicle, Examples, paclitaxel or vincristine at the doses indicated on days 1, 5, 9. Relative tumor growth is determined during the experiment and % T/C calculated. Statistical analyses are Student's t-test of treated time points vs. vehicle (P < 0.01)

The compounds of Formula (I) may be obtained as inorganic or organic salts using methods known to those skilled in the art (Richard C. Larock, Comprehensive Organic Transformations, VCH publishers, 411-415, 1989). It is well known to one skilled in the art that an appropriate salt form is chosen based on physical and chemical stability, flowability, hydroscopicity and solubility.

Pharmaceutically acceptable salts of the compounds of Formula (I) with an acidic moiety may be formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be formed from organic and inorganic acids. For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. An additional acid is trifluoroacetic acid (TFA). The compounds can also be used in the form of esters, carbamates and other conventional prodrug forms, which when providing in such form, convert to the active moiety in vivo.

Providing, means to make available and is intended to include direct administration as well as in vivo (e.g. prodrugs.) of compounds used in the method of treating, inhibiting the growth of, or eradicating a tumor in a mammal in need thereof wherein said tumor is resistant to at least one chemotherapeutic agent which method comprises providing to said mammal an effective amount of a compound of Formula (I).

Based on the results of these standard pharmacological test procedures, the compounds of this invention are useful as agents for treating, inhibiting the growth of or eradicating tumors resistant to chemotherapeutic agents and in particular to antimitotic compounds, including paclitaxel. It is estimated that a 70 kg human will receive an exposure, or AUC, to drug that is nearly equivalent to the efficacious dose in mice upon a preferred effective intravenous dose of about 0.6 to about 1.3 mg. Therefore, a more preferred effective regimen for optimum results would be from about 0.8 to about 200 micrograms (ug)/kg of body weight per cycle and such dosage units are employed that a total of from about 0.05 mg to about 150 mg of the active compound for a subject of about 70 kg of body weight are administered intravenously in a cycle. A cycle may be once every 1, 2 or 3 weeks as typically used for other anti-microtubule drugs in the clinic.

Tumors are selected from the group consisting of breast, colon, lung, prostate, melanoma, epidermal, leukemia, kidney, bladder, mouth, larynx, esophagus, stomach, ovary, pancreas, liver, skin and brain.

The dosage regimen for treating mammals may be adjusted to provide the optimum therapeutic response. For example, several divided doses may be provided per cycle or the dose may be proportionally reduced as indicated by the exigencies of the therapeutic situation. A decidedly practical advantage is that these active compounds may be provided in any convenient manner such as by the oral, intravenous, intramuscular or subcutaneous routes. Preferably compounds of the invention are provided by intravenous routes.

The active compounds may be orally provided, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 0.5 and 1500 mg of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

The active compounds of the invention may also be provided parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures therof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and starage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils. Preferably, compounds of this invention are provided by an IV route.

The compounds of this invention and their preparation are illustrated by the following non-limiting examples.

General Procedure I (Amide Formation)

Method A: To a cooled (0° C., ice-water bath) solution of the carboxylic acid (1 mmol) in anhydrous solvent (acetonitrile or dimethylformamide, 3-5 ml) are added hydroxybenzotriazole (1.1 mmol) and 1-(3-dimethylaminopropyl)-3-ethylcarbodiimide hydrochloride (1.2 mmol) under an inert atmosphere. The cooling bath is removed, and the resulting mixture is stirred at room temperature for 2-15 hours, until a clear solution is obtained. To this mixture is added a solution of an amine in anhydrous solvent (3-5 ml) at 0° C., and the resulting mixture is stirred at room temperature for 2-24 hours until Mass spectra analysis indicated no starting material left in the reaction mixture. The reaction mixture is concentrated in vacuo, and the product is purified by separation using preparative HPLC.

Alternatively, the product is isolated by aqueous work-up procedure: the reaction mixture is diluted with ethyl acetate (100 ml/mmol), and the organic layer is washed with saturated aqueous sodium bicarbonate solution and saturated sodium chloride solution, dried over anhydrous sodium sulfate, and concentrated in vacuo. The product is purified by chromatography (silica gel).

Method B: To N,β,β-trimethyl-L-phenylalanyl-$N^1$-[(1S,2E)-3-carboxy-1-isopropylbut-2-enyl]-$N^1$,3-dimethyl-L-valinamide (0.1 mmol, Andersen, R. WO 99/32509) in acetonitrile (5.0 mL) at 25° C. is added 1-hydroxybenzotriazole hydrate (0.12 mmol) and 1-(3-dimethylaminopropyl)-3-ethylcarbodiimide hydrochloride (1.33 mmol). After 2-18 hours an amine (0.4 mmol) is added. After 1-18 hours the reaction mixture is concentrated in vacuo, dissolved in dimethylformamide, and the product is purified by reverse phase HPLC (0.01% aqueous trifluoroacetic acid/acetonitrile gradient system).

Method C: A mixture of N,β,β-trimethyl-L-phenylalanyl-$N^1$-[(1S,2E)-3-carboxy-1-isopropylbut-2-enyl]-$N^1$,3-dimethyl-L-valinamide (1.0 equivalent, Andersen, R. WO 99/32509), hydroxybenzotriazole hydrate (1.2 equivalents), 1-(3-dimethylaminopropyl)-3-ethylcarbodiimine hydrochloride (1.2 equivalents), an amine (1.2 equivalents) and Hunig's base (2.0 equivalents) in anhydrous dimethylformamide (approx 6 mmol) are stirred under a nitrogen atmosphere overnight. The solvent is removed, the residue is taken up in methanol, and the product is purified by reverse phase HPLC (0.01% trifluoroacetic acid in water/acetonitrile).

General Procedure II (Ester Hydrolysis):

A peptide ester is dissolved in methanol (24 mmol), and cooled to 0° C. (ice-water bath). To this solution is added water (8 mmol) and aqueous lithium hydroxide solution (8 mol equivalents). The cooling bath is removed, and the resulting mixture is stirred at room temperature for 15 hours. Methanol is removed in vacuo, and the residual aqueous mixture is cooled with an ice water bath, and acidified to pH 5.5-6.0 with aqueous 1N citric acid solution. The precipitate is collect by filtration, and the solid is washed with cold water, and dried over high vacuum. Alternatively, the product can be purified by preparative reverse phase HPLC.

EXAMPLE 1

N,β,β,3-Tetramethyl-L-phenylalanyl-$N^1$-[(1S,2E)-1-isopropyl-3-methyl-4-morpholin-4-yl-4-oxobut-2-enyl]-$N^1$,3-dimethyl-L-valinamide By using an analogous procedure to that described in General Procedure I Method A, N,β,β,3-tetramethyl-L-phenylalanyl-$N^1$-[(1S,2E)-3-carboxy-1-isopropyl-2-butenyl]-$N^1$,3-dimethyl-L-valinamide (100 mg, 0.205 mmol) is treated with hydroxybenzotriazole (36 mg, 0.27 mmol) and 1-(3-dimethylaminopropyl)-3-ethylcarbodiimide hydrochloride (59 mg, 0.31 mmol) in anhydrous acetonitrile (3 ml) at room temperature for 15 hours, followed by addition of morpholine (0.036 ml, 0.41 mmol). After stirring at room temperature for 15 hours, the product is purified using the aqueous work-up method, to provide the title compound (89 mg, 78%) as a orange amorphous solid.

MS (ES): m/z 557.4 (M+H). Analytical HPLC: (4.6×150 mm YMC Pro Pack C18 column eluted with 10 to 100% acetonitrile in water containing 0.02% formic acid over 29 minutes): 92.55% (at 17.3 minutes) of N,β,β,3-tetramethyl-L-phenylalanyl-$N^1$-[(1S,2E)-1-isopropyl-3-methyl-4-morpholin-4-yl-4-oxobut-2-enyl]-$N^1$,3-dimethyl-L-valinamide, and 5.99% (at 18.8 minutes) of another diastereomer.

EXAMPLE 2

N,β,β,3,4-Pentamethyl-L-phenylalanyl-$N^1$-[(1S,2E)-1-isopropyl-3-methyl-4-morpholin-4-yl-4-oxobut-2-enyl]-$N^1$,3-dimethyl-L-valinamide By using an analogous procedure described in General Procedure I Method A, N,β,β,3,4-pentamethyl-L-phenylalanyl-$N^1$-[(1S,2E)-3-carboxy-1-isopropyl-2-butenyl]-$N^1$,3-dimethyl-L-valinamide (107.7 mg, 0.215 mmol) is treated with hydroxybenzotriazole (44 mg, 0.323 mmol) and 1-(3-dimethylaminopropyl)-3-ethylcarbodiimide hydrochloride (65 mg, 0.344 mmol) in anhydrous dimethylformamide (3 ml) at room temperature for 2 hours, followed by addition of morpholine (0.038 ml, 0.43 mmol). After stirring at room temperature for 36 hours, the product is purified by preparative HPLC, to provide the trifluoroacetic acid salt of the title compound (82 mg, 66.8%) as a white amorphous solid MS (ES): m/z 571.4 (M+H). IR $cm^{-1}$:2966,1669,1634. Analytical HPLC: (4.6×150 mm Prodigy ODS(3) 320486 column eluted with 10 to 100% acetonitrile in water containing 0.02% formic acid over 30 minutes):96.015% (at 16.506 minutes) of N,β,β,3,4-pentamethyl-L-phenylalanyl-$N^1$-[(1S,2E)-1-isopropyl-3-methyl-4-morpholin-4-yl-4-oxobut-2-enyl]-$N^1$,3-dimethyl-L-valinamide, and 0.78% (at 16.923 minutes), 0.747% (at 17.441 minutes), and 0.29% (at 17.71 minutes) of three other diastereomers.

EXAMPLE 3

N,β,β,3,5-Pentamethyl-L-phenylalanyl-N$^1$-[(1S,2E)-1-isopropyl-3-methyl-4-morpholin-4-yl-4-oxobut-2-enyl]-N$^1$,3-dimethyl-L-valinamide By using an analogous procedure described in General Procedure I Method A, N,β,β,3,5-pentamethyl-L-phenylalanyl-N$^1$-[(1S,2E)-3-carboxy-1-isopropyl-2-butenyl]-N$^1$,3-dimethyl-L-valinamide (104 mg, 0.2073 mmol) is treated with hydroxybenzotriazole (45 mg, 0.333 mmol) and 1-(3-dimethylaminopropyl)-3-ethylcarbodiimide hydrochloride (65 mg, 0.344 mmol) in anhydrous dimethylformamide (3 ml) at room temperature for 2 hours, followed by addition of morpholine (0.04 ml, 0.458 mmol). After stirring at room temperature for 36 hours, the product is purified by preparative HPLC to provide the trifluoroacetic acid salt of the title compound (90.0 mg, 87.1%) as a white amorphous solid. MS (ES): m/z 571.4 (M+H). Analytical HPLC: (4.6×150 mm YMC Pack Pro C18 column eluted with 10 to 100% acetonitrile in water containing 0.02% formic acid over 35 minutes): 97.39% (at 18.878 minutes) of N,β,β,3,5-pentamethyl-L-phenylalanyl-N$^1$-[(1S,2E)-1-isopropyl-3-methyl-4-morpholin-4-yl-4-oxobut-2-enyl]-N$^1$,3-dimethyl-L-valinamide, and 0.66% (at 20.395 minutes) of the other diastereomer.

EXAMPLE 4

N,β,β,3,4-Pentamethyl-D-phenylalanyl-N$^1$[(1S,2E)-1-isopropyl-3-methyl-4-morpholin-4-yl-4-oxobut-2-enyl]-N$^1$,3-dimethyl-L-valinamide By using an analogous procedure described in General Procedure I Method A, N,β,β,3,4-pentamethyl-D-phenylalanyl-N$^1$-[(1S,2E)-3-carboxy-1-isopropyl-2-butenyl]-N$^1$,3-dimethyl-L-valinamide (150 mg, 0.299 mmol) is treated with hydroxybenzotriazole (60 mg, 0.444 mmol) and 1-(3-dimethylaminopropyl)-3ethylcarbodiimide hydrochloride (86 mg, 0.449 mmol) in anhydrous acetonitrile (3 ml) at room temperature for 2 hours, followed by addition of morpholine (0.052 ml, 0.596 mmol). After stirring at room temperature for 36 hours, the product is purified by preparative HPLC, to provide the trifluoroacetic acid salt of the title compound (60 mg, 35.2%) as a white amorphous solid. MS (ES): m/z 571.4 (M+H). IR cm$^{-1}$:2964, 1669, 1636. Analytical HPLC: (4.6×150 mm YMC Pack Pro C18 column eluted with 10 to 100% acetonitrile in water containing 0.02% formic acid over 35 minutes):98.34% (at 13.604 minutes) of N,β,β,3,4-pentamethyl-D-phenylalanyl-N$^1$-[(1S,2E)-1-isopropyl-3-methyl-4-morpholin-4-yl-4-oxobut-2-enyl]-N$^1$,3-dimethyl-L-valinamide, and 0.28% (at 13.3 minutes) and 0.26% (at 14.4 minutes) of two other diastereomers.

EXAMPLE 5

N,β,β,3,5-Pentamethyl-D-phenylalanyl-N$^1$-[(1S,2E)-1-isopropyl-3-methyl-4-morpholin-4-yl-4-oxobut-2-enyl]-N$^1$,3-dimethyl-L-valinamide By using an analogous procedure described in General Procedure I Method A, N,β,β,3,5-pentamethyl-D-phenylalanyl-N$^1$-[(1S,2E)-3-carboxy-1-isopropyl-2-butenyl]-N$^1$,3-dimethyl-L-valinamide (150 mg, 0.299 mmol) is treated with hydroxybenzotriazole (60 mg, 0.444 mmol) and 1-(3-dimethylaminopropyl)-3-ethylcarbodiimide hydrochloride (86 mg, 0.449 mmol) in anhydrous acetonitrile (3 ml) at room temperature for 2 hours, followed by addition of morpholine (0.052 ml, 0.596 mmol). After stirring at room temperature for 36 hours, the product is purified by preparative HPLC, to provide the trifluoroacetic acid salt of the title compound (100 mg, 58.6%) as a white amorphous solid. MS (ES): m/z 571.4 (M+H). IR cm$^{-1}$: 2965, 1669, 1636. Analytical HPLC: (4.6×150 mm YMC Pack Pro C18 column eluted with 10 to 100% acetonitrile in water containing 0.02% formic acid over 35 minutes): 86.47% (at 13.847 minutes) of N,β,β,3,5-pentamethyl-D-phenylalanyl-N$^1$-[(1S,2E)-1-isopropyl-3-methyl-4-morpholin-4-yl-4-oxobut-2-enyl]-N$^1$,3-dimethyl-L-valinamide, and 10.04% (at 13.448 minutes) of the other diastereomer.

EXAMPLE 6

N,β,β,3-Tetramethyl-L-phenylalanyl-N$^1$-[(1S,2E)-1-isopropyl-3-methyl-4-(4-methylpiperazin-1-yl)-4-oxobut-2-enyl]-N$^1$,3-dimethyl-L-valinamide trifluoroacetic acid salt By using an analogous procedure described in General Procedure I Method A, N,β,β,3-tetramethyl-L-phenylalanyl-N$^1$-[(1S,2E)-3-carboxy-1-isopropyl-2-butenyl]-N$^1$,3-dimethyl-L-valinamide (100 mg, 0.205 mmol) is treated with hydroxybenzotriazole (36 mg, 0.27 mmol) and 1-(3-dimethylaminopropyl)-3-ethylcarbodiimide hydrochloride (59 mg, 0.31 mmol) in anhydrous acetonitrile (10 ml) at room temperature for 15 hours, followed by addition of N,N-diiospropylethylamine (0.143 ml, 0.82 mmol) and 1-methylpiperazine (0.045 ml, 0.41 mmol). After stirring at room temperature for 4 hours, the product is purified by preparative HPLC, to provide the trifluoroacetic acid salt of the title compound (132 mg, 94%) as a white amorphous solid. MS (ES): m/z 570.4 (M+H). IR cm$^{-1}$: 2969.14, 1675.70, 1629.86, 1203.89, 1134.29. Analytical HPLC: (4.6×150 mm YMC Pack Pro C18 column eluted with 10 to 100% acetonitrile in water containing 0.02% formic acid over 35 minutes): 92.03% (at 7.5 minutes) of N,β,β,3-tetramethyl-L-phenylalanyl-N$^1$-[(1S,2E)-1-isopropyl-3-methyl-4-(4-methylpiperazin-1-yl)-4-oxobut-2-enyl]-N$^1$,3-dimethyl-L-valinamide, and 4.87% (at 9.2 minutes) of the other diastereomer.

EXAMPLE 7

N,β,β,3,4-Pentamethyl-L-phenylalanyl-N$^1$-[(1S,2E)-1-isopropyl-3-methyl-4-(4-methylpiperazin-1-yl)-4-oxobut-2-enyl]-N$^1$,3-dimethyl-L-valinamide By using an analogous procedure described in General Procedure I Method A, N,β,β,3,4-pentamethyl-L-phenylalanyl-N$^1$-[(1S,2E)-3-carboxy-1-isopropyl-2-butenyl]-N$^1$,3-dimethyl-L-valinamide (105 mg, 0.2093 mmol) is treated with hydroxybenzotriazole (44 mg, 0.326 mmol) and 1-(3-dimethylaminopropyl)-3-ethylcarbodiimide hydrochloride (65 mg, 0.339 mmol) in anhydrous dimethylformamide (3 ml) at room temperature for 3 hours, followed by addition of 1-methylpiperazine (0.032 ml, 0.32 mmol). After stirring at room temperature for 15 hours, the product (108 mg, 87.7%) is purified by preparative HPLC, to provide the trifluoroacetic acid salt of the title compound (66.1 mg, 53.7%) as a white solid. MS (ES): m/z 584.4 (M+H). IR cm$^{-1}$: 2966, 1670,1634. Analytical HPLC: (4.6×150 mm Prodigy ODS (3) column eluted with 10 to 100% acetonitrile in water containing 0.02% formic acid over 30 minutes): 98.325% (at 8.182 minutes).

EXAMPLE 8

N,β,β,3,5-Pentamethyl-L-phenylalanyl-N$^1$-[(1S,2E)-1-isopropyl-3-methyl-4-(4-methylpiperazin-1-yl)-4-oxobut-2-enyl]-N$^1$,3-dimethyl-L-valinamide By using an analogous procedure described in General Procedure Method A, N,β,β,3,5-pentamethyl-L-phenylalanyl-N$^1$-[(1S,2E)-3-carboxy-1-isopropyl-2-butenyl]-N$^1$,3-dimethyl-L-valinamide (90 mg, 0.179 mmol) is treated with hydroxybenzotriazole (50 mg, 0.370 mmol) and 1-(3-dimethylaminopropyl)-3-ethylcarbodiimide hydrochloride (70 mg, 0.365 mmol) in anhydrous acetonitrile (8 ml) at room temperature for 3 hours, followed by addition of 1-methylpiperazine (0.035 ml, 0.32 mmol). After stirring at room temperature for 15 hours, the product is purified by preparative HPLC, to provide the trifluoroacetic acid salt of the title compound as a white solid. MS (ES): m/z 584.4 (M+H). IR cm$^{-1}$: 2966,1671,1634 Analytical HPLC: (4.6×150 mm YMC Pack Pro C18 column eluted with 10 to 100% acetonitrile in water containing 0.02% formic acid over 30 minutes): 96.63% (at 8.049 minutes) of N,β,β,3-tetramethyl-L-phenylalanyl-N$^1$-[(1S,2E)-1-isopropyl-3-methyl-4-(4-methylpiperazin-1-yl)-4-oxobut-2-enyl]-N$^1$,3-dimethyl-L-valinamide, and 1.39% (at 9.352 minutes) of the other diastereomer.

EXAMPLE 9

1-{(2E,4S)-2,5-Dimethyl-4-[methyl(N,β,β,3-tetramethyl-L-phenylalanyl-3-methyl-L-valyl)amino]hex-2-enoyl}-D-prolyl-N-benzyl-D-prolinamide trifluoroacetic acid salt By using an analogous procedure described in General Procedure I Method A, N,β,β,3-tetramethyl-L-phenylalanyl-N$^1$-[(1S,2E)-3-carboxy-1-isopropyl-2-butenyl]-N$^1$,3-dimethyl-L-valinamide (100 mg, 0.205 mmol) is treated with hydroxybenzotriazole (36 mg, 0.27 mmol) and 1-(3-dimethylaminopropyl)-3-ethylcarbodiimide hydrochloride (59 mg, 0.31 mmol) in anhydrous acetonitrile (10 ml) at room temperature for 40 hours, followed by addition of diisopropylethylamine (0.143 ml, 0.82 mmol) and a solution of L-prolyl-N-benzyl-L-prolinamide trifluoroacetic acid salt (255 mg, 0.615 mmol) in anhydrous acetonitrile (3 ml). After stirring at room temperature for 4 hours, the product is purified by preparative HPLC, to provide the trifluoroacetic acid salt of the title compound (126.6 mg, 69%) as a white amorphous solid. MS (ES): m/z 771.5 (M+H). IR cm$^{-1}$: 3306.94, 2969.17, 1673.9, 1642.27, 1203.38. Analytical HPLC: (4.6×150 mm YMC Pack Pro C18 column eluted with 10 to 100% acetonitrile in water containing 0.02% formic acid over 35 minutes): 92.56% (at 17.7 minutes) of 1-{(2E,4S)-2,5-dimethyl-4-[methyl(N,β,β,3-tetramethyl-L-phenylalanyl-3-methyl-L-valyl)amino]hex-2-enoyl}-D-prolyl-N-benzyl-D-prolinamide, and 6.92% (at 18.5 minutes) of the other diastereomer.

EXAMPLE 10

1-{(2E,4S)-2,5-Dimethyl-4-[methyl(N,β,β,3,4-pentamethyl-L-phenylalanyl-3-methyl-L-valyl)amino]hex-2-enoyl}-L-prolyl-N-benzyl-L-prolinamide By using an analogous procedure described in General Procedure I Method A, N,β,β,3,4-pentamethyl-L-phenylalanyl-N$^1$[(1S,2E)-3-carboxy-1-isopropyl-2-butenyl]-N$^1$,3-dimethyl-L-valinamide (128 mg, 0.26 mmol) is treated with hydroxybenzotriazole (42 mg, 0.32 mmol) and 1-(3-dimethylaminopropyl)-3-ethylcarbodiimide hydrochloride (70 mg, 0.36 mmol) in anhydrous acetonitrile (5 ml) at room temperature for 15 hours, followed by addition of diisopropylethylamine (0.068 ml, 0.39 mmol) and a solution of L-prolyl-N-benzyl-L-prolinamide trifluoroacetic acid salt (108 mg, 0.26 mmol) in anhydrous acetonitrile (5 ml). After stirring at room temperature for 24 hours, the product is purified by preparative HPLC, to provide the trifluoroacetic acid salt of the title compound 126.6 mg, 62.0%) as a white amorphous solid. MS (ES): m/z 785.5 (M+H). IR cm$^{-1}$: 2967, 1634. Analytical HPLC: (4.6×150 mm YMC Pack Pro C18 column eluted with 10 to 100% acetonitrile in water containing 0.02% formic acid over 30 minutes): 96.35% (at 18.713 minutes) of 1-{(2E, 4S)-2,5-dimethyl-4-[methyl(N,β,β,3,4-pentamethyl-L-phenylalanyl-3-methyl-L-valyl)amino]hex-2-enoyl}-L-prolyl-N-benzyl-L-prolinamide, and 0.73% (at 19.277 minutes) of the other diastereomer.

EXAMPLE 11

1-{(2E,4S)-2,5-Dimethyl-4-[methyl(N,β,β,3,5-pentamethyl-L-phenylalanyl-3-methyl-L-valyl)amino]hex-2-enoyl}-L-prolyl-N-benzyl-L-prolinamide By using an analogous procedure described in General Procedure Method A, N,β,β,3,5-pentamethyl-L-phenylalanyl-N$^1$[(1S,2E)-3-carboxy-1-isopropyl-2-butenyl]-N$^1$,3-dimethyl-L-valinamide (83 mg, 0.166 mmol) is treated with hydroxybenzotriazole (27 mg, 0.20 mmol) and 1-(3-dimethylaminopropyl)-3-ethylcarbodiimide hydrochloride (45 mg, 0.23 mmol) in anhydrous acetonitrile (5 ml) at room temperature for 15 hours, followed by addition of diisopropylethylamine (0.045 ml, 0.25 mmol) and a solution of L-prolyl-N-benzyl-L-prolinamide trifluoroacetic acid salt (69 mg, 0.166 mmol) in anhydrous acetonitrile (5 ml). After stirring at room temperature for 24 hours, the product is purified by preparative HPLC, to provide the trifluoroacetic acid salt of the title compound as a white amorphous solid. MS (ES): m/z 785.2 (M+H). IR cm$^{-1}$: 2968,1635. Analytical HPLC: (4.6×150 mm YMC Pack Pro C18 column eluted with 10 to 100% acetonitrile in water containing 0.02% formic acid over 30 minutes): 83.99% (at 13.513 minutes) of 1-{(2E,4S)-2,5-dimethyl-4-[methyl(N,β,β,3,5-pentamethyl-L-phenylalanyl-3-methyl-L-valyl)amino]hex-2-enoyl}-L-prolyl-N-benzyl-L-prolinamide, and 3.02% (at 13.795 minutes) of the other diastereomer.

EXAMPLE 12

N,β,β,3,4-Pentamethyl-L-phenylalanyl-N$^1$-[(1S,2E)-4-(4-benzylpiperazin-1-yl)-1-isopropyl-3-methyl-4-oxobut-2-enyl]-N$^1$,3-dimethyl-L-valinamide By using an analogous procedure described in General Procedure I Method A, N,β,β,3,4-pentamethyl-L-phenylalanyl-N$^1$-[(1S,2E)-3-carboxy-1-isopropyl-2-butenyl]-N$^1$,3-dimethyl-L-valinamide (100 mg, 0.199 mmol) is treated with hydroxybenzotriazole (35 mg, 0.259 mmol) and 1-(3-dimethylaminopropyl)-3-ethylcarbodiimide hydrochloride (57 mg, 0.299 mmol) in acetonitrile (10 ml) at room temperature for 15 hours, followed by addition of diisopropylethylamine (0.139 ml, 0.797 mmol) and 1-benzylpiperazine (0.069 ml, 0.399 mmol). After stirring at room temperature for 6.5 hours, the product is purified by preparative HPLC, to provide the trifluoroacetic acid salt of the title compound (136 mg, 88%) as a white solid. MS (ES): m/z 660.5 (M+H), 330.9 (2M+H).

IR cm$^{-1}$: 3426.46, 2969.86, 1673.74, 1634.74, 1202.94. Analytical HPLC: (4.6×150 mm YMC Pack Pro C18 column eluted with 10 to 95% acetonitrile in water containing 0.02% formic acid over 25 minutes): 93.90% (at 8.3 minutes).

EXAMPLE 13

N,β,β,3,4-Pentamethyl-D-phenylalanyl-N$^1$-[(1S,2E)-4-(4-benzylpiperazin-1-yl)-1-isopropyl-3-methyl-4-oxobut-2-enyl]-N$^1$,3-dimethyl-L-valinamide By using an analogous procedure described in General Procedure I Method A, N,β,β,3,4-pentamethyl-D-phenylalanyl-N$^1$-[(1S,2E)-3-carboxy-1-isopropyl-2-butenyl]-N$^1$,3-dimethyl-L-valinamide (100 mg, 0.199 mmol) is treated with hydroxybenzotriazole (35 mg, 0.259 mmol) and 1-(3-dimethylaminopropyl)-3-ethylcarbodiimide hydrochloride (57 mg, 0.299 mmol) in acetonitrile (10 ml) at room temperature for 15 hours, followed by addition of diisopropylethylamine (0.139 ml, 0.797 mmol) and 1-benzylpiperazine (0.069 ml, 0.399 mmol). After stirring at room temperature for 6.5 hours, the product is purified by preparative HPLC, to provide the trifluoroacetic acid salt of the title compound (113 mg, 86%) as a white solid. MS (ES): m/z 660.5 (M+H), 330.7 (M+2H). IR cm$^{-1}$: 3328.24, 2969.50, 1674.73, 1633.08, 1202.46, 1134.70. Analytical HPLC: (4.6×150 mm Prodigy ODS (3) column eluted with 10 to 100% acetonitrile in water containing 0.02% formic acid over 25 minutes): 5.04% (at 8.2 minutes), 79.40% (at 8.7 minutes).

EXAMPLE 14

N,β,β,3,5-Pentamethyl-L-phenylalanyl-N$^1$-[(1S,2E)-4-(4-benzylpiperazin-1-yl)-1-isopropyl-3-methyl-4-oxobut-2-enyl]-N$^1$,3-dimethyl-L-valinamide By using an analogous procedure described in General Procedure I Method A, N,β,β,3,5-pentamethyl-L-phenylalanyl-N$^1$-[(1S,2E)-3-carboxy-1-isopropyl-2-butenyl]-N$^1$,3-dimethyl-L-valinamide (100 mg, 0.199 mmol) is treated with hydroxybenzotriazole (35 mg, 0.259 mmol) and 1-(3-dimethylaminopropyl)-3-ethylcarbodiimide hydrochloride (57 mg, 0.299 mmol) in acetonitrile (10 ml) at room temperature for 15 hours, followed by addition of diisopropylethylamine (0.139 ml, 0.799 mmol) and 1-benzylpiperazine (0.069 ml, 0.399 mmol). After stirring at room temperature for 15 hours, the product is purified by preparative HPLC, to provide the trifluoroacetic acid salt of the title compound (125 mg, 81%) as a white solid. MS (ES): m/z 660.6 (M+H), 331.0 (2M+H). IR cm$^{-1}$: 3434.21, 2968.89, 1674.58, 1632.61, 1203.08. Analytical HPLC: (4.6×150 mm YMC Pack Pro C18 column eluted with 10 to 95% acetonitrile in water containing 0.02% formic acid over 25 minutes): 93.38% at 8.6 minutes

EXAMPLE 15

N,β,β,β-Tetramethyl-L-phenylalanyl-N$^1$[(1S,2E)-4-(4-benzylpiperazin-1-yl)-1-isopropyl-3-methyl-4-oxobut-2-enyl]-N$^1$,3-dimethyl-L-valinamide By using an analogous procedure described in General Procedure I Method A, N,β,β,3-tetramethyl-L-phenylalanyl-N$^1$[(1S,2E)-3-carboxy-1-isopropyl-2-butenyl]-N$^1$,3-dimethyl-L-valinamide (150 mg, 0.31 mmol) is treated with hydroxybenzotriazole (54 mg, 0.4 mmol) and 1-(3-dimethylaminopropyl)-3-ethylcarbodiimide hydrochloride (59 mg, 0.46 mmol) in acetonitrile (10 ml) at room temperature for 15 hours, followed by addition of diisopropylethylamine (0.143 ml, 0.82 mmol) and 1-benzylpiperazine (0.043 ml, 0.25 mmol). After stirring at room temperature for 3 days, the product is purified by preparative HPLC, to provide the trifluoroacetic acid salt of the title compound (81 mg, 34%) as a yellow solid. MS (ES): m/z 646.4 (M+H), 323.8 (M+2H). IR cm$^{-1}$: 3428.51, 2969.56, 1674.67, 1202.94. Analytical HPLC: (4.6×150 mm YMC Pack Pro C18 column eluted with 10 to 95% acetonitrile in water containing 0.02% formic acid over 25 minutes): 90.90% at 6.5 minutes.

EXAMPLE 16

3-Chloro-N,β,β-trimethyl-L-phenylalanyl-N$^1$-[(1S,2E)-4-(4-benzylpiperazin-1-yl)-1-isopropyl-3-methyl-4-oxobut-2-enyl]-N$^1$,3-dimethyl-L-valinamide By using an analogous procedure described in General Procedure I Method A, 3-chloro-N,β,β-trimethyl-L-phenylalanyl-N$^1$-[(1S,2E)-3-carboxy-1-isopropyl-2-butenyl]-N$^1$,3-dimethyl-L-valinamide (121 mg, 0.238 mmol) is treated with hydroxybenzotriazole (42 mg, 0.31 mmol) and 1-(3-dimethylaminopropyl)-3-ethylcarbodiimide hydrochloride (68 mg, 0.36 mmol) in acetonitrile (10 ml) at room temperature for 15 hours, followed by addition of diisopropylethylamine (0.166 ml, 0.95 mmol) and 1-benzylpiperazine (0.05 ml, 0.29 mmol). After stirring at room temperature for 24 hours, the product is purified by preparative HPLC, to provide the trifluoroacetic acid salt of the title compound (157 mg, 85%) as a tan solid. MS (ES): m/z 666.5 (M+H), 333.8 (M+2H). IR cm$^{-1}$: 2970.22, 1674.58, 1637.35, 1420.27, 1203.00. Analytical HPLC: (4.6×150 mm YMC Pack Pro C18 column eluted with 10 to 95% acetonitrile in water containing 0.02% formic acid over 25 minutes): 86.28% at 7.9 minutes, 10.39% at 8.1 minutes, 1.01% at 8.4 minutes.

EXAMPLE 17

N,β,β,3,4-Pentamethyl-L-phenylalanyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide By using an analogous procedure described in General Procedure I Method A, N,β,β,3,4-pentamethyl-L-phenylalanyl-N$^1$-[(1S,2E)-3-carboxy-1-isopropyl-2-butenyl]-N$^1$,3-dimethyl-L-valinamide (150 mg, 0.299 mmol) is treated with hydroxybenzotriazole (53 mg, 0.384 mmol) and 1-(3-dimethylaminopropyl)-3-ethylcarbodiimide hydrochloride (86 mg, 0.448 mmol) in acetonitrile (10 ml) at room temperature for 15 hours, followed by addition of diisopropylethylamine (0.208 ml, 1.2 mmol) and L-proline methyl ester hydrochloride (59 mg, 0.36 mmol). After stirring at room temperature for 4 hours, the product is purified by preparative HPLC, to provide the trifluoroacetic acid salt of the title compound (208 mg, 96%) as a white solid. MS (ES): m/z 613.4 (M+H). IR cm$^{-1}$: 3395.09, 2968.00, 1747.41, 1674.85, 1630.23, 1202.70. Analytical HPLC: (4.6×150 mm YMC Pack Pro C18 column eluted with 10 to 95% acetonitrile in water containing 0.02% formic acid over 25 minutes): 87.55% at 11.2 minutes.

EXAMPLE 18

N,β,β,3,4-Pentamethyl-L-phenylalanyl-N$^1$-{(1S,2E)-4-[(2S)-2-carboxypyrrolidin-1-yl]-1-isopropyl-3-methyl-4-oxobut-2-enyl}-N$^1$,3-dimethyl-L-valinamide By using an analogous procedure described in General Procedure II, methyl (2S)-1-{(2E,4S)-4-[((2S)-2-{[(2S)-3-(3,4-dimethylphenyl)-3-methyl-2-(methylamino)butanoyl]amino}-3,3-dimethylbutanoyl)(methyl)amino]-2,5-dimethylhex-2-enoyl}pyrrolidine-2-carboxylate trifluoroaceti acid salt (140 mg, 0.19 mmol, obtained from Example 17) in methanol (1.5 ml) and water (0.5 ml) is treated with lithium hydroxide (1 mmol, aqueous solution). After stirring at room temperature for 3 hours, the product is purified by preparative HPLC, to provide the trifluoroacetic acid salt of the title compound (147 mg, 100%) as a white solid. MS (ES): m/z 599.5 (M+H). IR cm$^{-1}$: 3431.56, 2968.23, 1729.35, 1201.76. Analytical HPLC: (4.6×150 mm YMC Pack Pro C18 column eluted with 10 to 95% acetonitrile in water containing 0.02% formic acid over 25 minutes): 94.83% at 10.2 minutes.

EXAMPLE 19

N,β,β,3,5-Pentamethyl-L-phenylalanyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide By using an analogous procedure described in General Procedure I Method A, N,β,β,3,5-pentamethyl-L-phenylalanyl-N$^1$-[(1S,2E)-3-carboxy-1-isopropyl-2-butenyl]-N$^1$,3-dimethyl-L-valinamide (150 mg, 0.299 mmol) is treated with hydroxybenzotriazole (53 mg, 0.389 mmol) and 1-(3-dimethylaminopropyl)-3-ethylcarbodiimide hydrochloride (86 mg, 0.448 mmol) in acetonitrile (10 ml) at room temperature for 15 hours, followed by addition of diisopropylethylamine (0.208 ml, 1.2 mmol) and L-proline methyl ester hydrochloride (59 mg, 0.36 mmol). After stirring at room temperature for 15 hours, the product is purified by preparative HPLC, to provide the trifluoroacetic acid salt of the title compound (106 mg, 49%) as a white solid. MS (ES): m/z 613.4 (M+H). IR cm$^{-1}$: 3388.60, 2967.14, 1747.20, 1676.16, 1631.95, 1202.88. Analytical HPLC: (4.6×150 mm YMC Pack Pro C18 column eluted with 10 to 95% acetonitrile in water containing 0.02% formic acid over 25 minutes): 81.54% at 11.4 minutes.

EXAMPLE 20

N,β,β,3,5-Pentamethyl-L-phenylalanyl-N$^1$-{(1S,2E)-4-[(2S)-2-carboxypyrrolidin-1-yl]-1-isopropyl-3-methyl-4-oxobut-2-enyl}-N$^1$,3-dimethyl-L-valinamide By using an analogous procedure described in General Procedure II, methyl (2S)-1-{(2E,4S)-4-[((2S)-2-{[(2S)-3-(3,5-dimethylphenyl)-3-methyl-2-(methylamino)butanoyl]amino}-3,3-dimethylbutanoyl)(methyl)amino]-2,5-dimethylhex-2-enoyl}pyrrolidine-2-carboxylate trifluoroacetic acid salt (58 mg, 0.095 mmol obtained from Example 19) in methanol (1.5 ml) and water (0.5 ml) is treated with lithium hydroxide (1 mmol, aqueous solution). After stirring at room temperature for 3 hours, the product is purified by preparative HPLC, to provide the trifluoroacetic acid salt of the title compound (35 mg, 52%) as a white solid. MS (ES): m/z 599.4 (M+H). Analytical HPLC: (4.6×150 mm YMC Pack Pro C18 column eluted with 10 to 95% acetonitrile in water containing 0.02% formic acid over 25 minutes): 94.37% at 10.3 minutes.

EXAMPLE 21

N,β,β,3-Tetramethyl-L-phenylalanyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide By using an analogous procedure described in General Procedure I Method A, N,β,β,3-tetramethyl-L-phenylalanyl-N$^1$— [(1S,2E)-3-carboxy-1-isopropyl-2-butenyl]-N$^1$,3-dimethyl-L-valinamide (100 mg, 0.205 mmol) is treated with hydroxybenzotriazole (36 mg, 0.27 mmol) and 1-(3-dimethylaminopropyl)-3-ethylcarbodiimide hydrochloride (59 mg, 0.31 mmol) in acetonitrile (10 ml) at room temperature for 15 hours, followed by addition of diisopropylethylamine (0.215 ml, 1.23 mmol) and L-proline methyl ester hydrochloride (61 mg, 0.37 mmol). After stirring at room temperature for 2 days, the product is purified by preparative HPLC, to provide the trifluoroacetic acid salt of the title compound (75 mg, 51%) as a yellow solid. MS (ES): m/z 599.4 (M+H). IR cm$^{-1}$: 2969.22, 1748.56, 1676.30, 1628.91, 1204.24. Analytical HPLC: (4.6×150 mm YMC Pack Pro C18 column eluted with 10 to 95% acetonitrile in water containing 0.02% formic acid over 25 minutes): 85.72% at 9.8 minutes, 1.23% at 10.8 minutes.

EXAMPLE 22

N,β,β,3-Tetramethyl-L-phenylalanyl-N$^1$-{(1S,2E)-4-[(2S)-2-carboxypyrrolidin-1-yl]-1-isopropyl-3-methyl-4-oxobut-2-enyl}-N$^1$,3-dimethyl-L-valinamide By using an analogous procedure described in General Procedure II, methyl (2S)-1-{(2E,4S)-4-[((2S)-3,3-dimethyl-2-{[(2S)-3-methyl-2-(methylamino)-3-(3-methylphenyl)butanoyl]amino}butanoyl)(methyl)amino]-2,5-dimethylhex-2-enoyl}pyrrolidine-2-carboxylate trifluoroacetic acid salt (141 mg, 0.198 mmol, obtained from Example 21) in methanol (1.5 ml) and water (0.5 ml) is treated with lithium hydroxide (1 mmol, aqueous solution). After stirring at room temperature for 15 hours, the product is purified by preparative HPLC, to provide the trifluoroacetic acid salt of the title compound (106 mg, 77%) as a white solid. MS (ES): m/z 585.3 (M+H). IR cm$^{-1}$: 2969, 1677, 1629, 1451, 1415, 1203. Analytical HPLC: (4.6×150 mm YMC Pack Pro C18 column eluted with 10 to 100% acetonitrile in water containing 20 mM ammonium acetate over 27 minutes): 99.50% at 14.3 minutes.

EXAMPLE 23

3-Chloro-N,β,β-trimethyl-L-phenylalanyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide By using an analogous procedure described in General Procedure I Method A, 3-chloro-N,β,β-trimethyl-L-phenylalanyl-N$^1$-[(1S,2E)-3-carboxy-1-isopropyl-2-butenyl]-N$^1$,3-dimethyl-L-valinamide (119 mg, 0.234 mmol) is treated with hydroxybenzotriazole (41 mg, 0.305 mmol) and 1-(3-dimethylaminopropyl)-3-ethylcarbodiimide hydrochloride (67 mg, 0.35 mmol) in acetonitrile (10 ml) at room temperature for 15 hours, followed by addition of diisopropylethylamine (0.163 ml, 0.94 mmol) and L-proline methyl ester hydrochloride (47 mg, 0.28 mmol). After stirring at room temperature for 15 hours, the product is purified by preparative HPLC, to provide the trifluoroacetic acid salt of the title compound (134 mg, 78%) as a white solid. MS (ES): m/z 619.4 (M+H). IR cm$^{-1}$: 2968.43, 1677.81, 1634.03, 1416.23, 1203.94, 1175.63. Analytical HPLC: (4.6×150 mm Capcell C18 column eluted with 10 to 95% acetonitrile in water containing 0.02% formic acid over 25 minutes): 77.08% at 9.8 minutes, 8.11% at 10.5 minutes.

EXAMPLE 24

3-Chloro-N,β,β-trimethyl-L-phenylalanyl-N$^1$-{(1S, 2E)-4-[(2S)-2-carboxypyrrolidin-1yl]-1-isopropyl-3-methyl-4-oxobut-2-enyl}-N$^1$,3-dimethyl-L-valinamide By using an analogous procedure described in General Procedure II, methyl (2S)-1-{(2E,4S)-4-[((2S)-2-{[(2S)-3-(3-chlorophenyl)-3-methyl-2-(methylamino)butanoyl]amino}-3,3-dimethylbutanoyl)(methyl)amino]-2,5-dimethylhex-2-enoyl}pyrrolidine-2-carboxylate trifluoroacetic acid salt (84 mg, 0.135 mmol, obtained from Example 23) in methanol (1 ml) and water (0.5 ml) is treated with lithium hydroxide (0.5 mmol). After stirring at room temperature for 6.5 hours, the product is purified by preparative HPLC, to provide the trifluoroacetic acid salt of the title compound (45 mg, 46%) as a white solid. MS (ES): m/z 605.5 (M+H). Analytical HPLC: (4.6×150 mm YMC Pack Pro C18 column eluted with 10 to 95% acetonitrile in water containing 0.02% formic acid over 25 minutes): 95.87% at 9.9 minutes, 3.70% at 10.4 minutes.

EXAMPLE 25

(E,4S)-4-[((2S)-3,3-dimethyl-2-{[(2S)-3-methyl-2-(methylamino)-3-phenylbutanoyl]amino}butanoyl)(methyl)amino]-N-hydroxy-2,5-dimethyl-2-hexenamide As described in General Procedure I Method B, to N,β,β-trimethyl-L-phenylalanyl-N$^1$[(1S,2E)-3-carboxy-1-isopropylbut-2-enyl]-N$^1$,3-dimethyl-L-valinamide (75 mg) in acetonitrile (5.0 mL) at 25° C. is added 1-hydroxybenzotriazole hydrate (26 mg) and 1-(3-dimethylaminopropyl)-3-ethylcarbodiimide hydrochloride (41 mg). After 2 hours 50% aqueous hydroxylamine (0.38 mL) is added. After 18 hours the reaction mixture is concentrated in vacuo, dissolved in acetonitrile/water, and purified by reverse phase HPLC (0.01% aqueous trifluoroacetic acid/acetonitrile gradient system) to give the trifluoroacetic acid salt of the title compound as a white powder (30 mg). MS (ES): m/z 489.0 (M+H).

EXAMPLE 26

N,β,β-trimethyl-L-phenylalanyl-N$^1$-[(1S,2E)-1-isopropyl-3-methyl-4-(4-methyl-1-piperazinyl)-4-oxo-2-butenyl]-N$^1$,3-dimethyl-L-valinamide As described in General Procedure I Method B to N,β,β-trimethyl-L-phenylalanyl-N$^1$-[(1S,2E)-3-carboxy-1-isopropylbut-2-enyl]-N$^1$,3-dimethyl-L-valinamide (50 mg) in acetonitrile (5.0 mL) at 25° C. is added 1-hydroxybenzotriazole hydrate (17 mg) and 1-(3-dimethylaminopropyl)-3-ethylcarbodiimide hydrochloride (27 mg). After 2 hours N-methylpiperazine (0.047 mL, 0.42 mmol) is added. After 18 hours the reaction mixture is concentrated in vacuo, dissolved in acetonitrile/water, and purified by reverse phase HPLC (0.01% aqueous trifluoroacetic acid/acetonitrile gradient system) to give the trifluoracetic acid salt of the title compound as a white powder (58 mg). MS (ES): m/z 556.42137 (M+H). (calc'd exact mass=555.41507)

EXAMPLE 27

(2S)-N-[(1S,2E)-1-isopropyl-3-methyl-4-(4-morpholinyl)-4-oxo-2-butenyl]-N,3,3-trimethyl-2-{[(2S)-3-methyl-2-(methylamino)-3-phenylbutanoyl]amino}butanamide As described in General Procedure I Method B, to N,β,β-trimethyl-L-phenylalanyl-N$^1$-[(1S,2E)-3-carboxy-1-isopropylbut-2-enyl]-N$^1$,3-dimethyl-L-valinamide (30 mg) in acetonitrile (5.0 mL) at 25° C. is added 1-hydroxybenzotriazole hydrate (10 mg) and 1-(3-dimethylaminopropyl)-3-ethylcarbodiimide hydrochloride (16 mg). After 2 hours morpholine (0.022 mL, 0.25 mmol) is added. After 18 hours the reaction mixture is concentrated in vacuo, dissolved in acetonitrile/water, and purified by reverse phase HPLC (0.01% aqueous trifluoroacetic acid/acetonitrile gradient system) to give the trifluoracetic acid salt of the title compound as a white powder (37 mg). MS (ES): m/z 543.6 (M+H).

EXAMPLE 28

1-{(2E,4S)-2,5-dimethyl-4-[methyl(N-methyl-3-phenyl-L-valyl-3-methyl-L-valyl)amino]hex-2-enoyl}-D-prolyl-N-benzyl-D-prolinamide As described in General Procedure I Method B, to N,β,β-trimethyl-L-phenylalanyl-N$^1$-[(1S,2E)-3-carboxy-1-isopropylbut-2-enyl]-N$^1$,3-dimethyl-L-valinamide (250 mg) in acetonitrile (25 mL) at 25° C. is added 1-hydroxybenzotriazole hydrate (85 mg) and 1-(3-dimethylaminopropyl)-3-ethylcarbodiimide hydrochloride (135 mg). After 21 hours a solution of D-prolyl-N-benzyl-D-prolinamide trifluoroacetic acid (660 mg, 1.59 mmol) and diisopropylethylamine (0.37 mL) in acetonitrile (3 mL) is added. After 18 hours the reaction mixture is concentrated in vacuo, dissolved in acetonitrile/water, and purified by reverse phase HPLC (water/acetonitrile gradient system) to give the title compound as a white powder. MS (ES): m/z 757.50073 (M+H). (calc'd exact mass=756.49409)

REFERENCE EXAMPLE 1

N-methoxy-N-methyl-2-phenylacetamide

Based on a procedure found in the literature (Guanti, G.; Banfi, L.; Riva, R. *Tetrahedron* 50(41), 1994, 11945-11966), a solution of phenylacetic acid (10 g, 73 mmol) in tetrahydrofuran (150 mL) is combined with a solution of N,O-dimethylhydroxylamine hydrochloride (13 g, 130 mmol) in water (150 mL). The pH is adjusted to 4.5 by the addition of 1 N aqueous sodium hydroxide solution. To the mixture is added 1-(3-dimethylaminopropyl)-3-ethylcarbodiimine hydrochloride (36 g, 190 mmol) as a solution in water (510 mL) dropwise over 30 minutes. Over the course of the addition, pH is maintained at 4.5 by the addition of 1 N aqueous sodium hydroxide solution. The reaction mixture is allowed to stir for 3 hours at room temperature and is then saturated with sodium chloride and extracted thrice with ethyl acetate. The combined extracts are washed with saturated aqueous sodium hydrogen carbonate (×2), water, and saturated aqueous sodium chloride solution, dried over anhydrous sodium sulfate, and concentrated under reduced pressure to yield a golden liquid (13 g, 100%). MS (ES$^+$): (M+H)=180.1

REFERENCE EXAMPLE 2

2-phenyl-1-(1,3-thiazol-2-yl)ethanone

Following the method of Itako et al. (Irako, N.; Hamada, Y.; Shioiri, T. *Tetrahedron* 48(35), 1992, 7251-7264), a solution of N,N,N',N'-tetramethylenediamine (9.2 mL, 61 mmol) in tetrahydrofuran (120 mL) is cooled to −78° C. (dry ice/acetone bath) while stirring under a nitrogen atmosphere. n-butyllithium (1.6 M in hexanes, 38 mL, 61 mmol) is added via syringe, followed by 2-bromothiazole (5.5 mL, 61 mmol), which is also added via syringe. The reaction mixture is stirred for 2 hours at −78° C., then N-methoxy-N-methyl-2-phenylacetamide (9.1 g, 51 mmol, from Reference Example 1) is added as a solution in tetrahydrofuran (120 mL). The resulting reaction mixture is stirred for 30 minutes at −78° C., then at −10° C. (NaCl/ice bath) for 2 hours before being quenched by the addition of 1 M potassium bisulfate solution (300 mL). The mixture is extracted thrice with diethyl ether. The combined extracts are washed with water and saturated aqueous sodium chloride solution, dried over anhydrous magnesium sulfate and concentrated under reduced pressure to a brown tar. The crude material is purified by flash chromatography (silica gel, hexanes/ethyl acetate) to give an orange-rust colored liquid (3.5 g, 35%). MS (ES$^+$): (M+H)=204.0

REFERENCE EXAMPLE 3

(1R)-2-phenyl-1-(1,3-thiazol-2-yl)ethanol

Following the method of Itako et al. (Irako, N.; Hamada, Y.; Shioiri, T. *Tetrahedron* 48(35), 1992, 7251-7264), to a 0° C. (ice-water bath) solution of (+)-B-chlorodiisopinocamphenylborane (+-DIP-Chloride, 3.9 g, 12 mmol) in diethyl ether (3 mL) is added dropwise a solution of 2-phenyl-1-(1,3-thiazol-2-yl)ethanone (0.83 g, 4.1 mmol, from Reference Example 2) in diethyl ether (17 mL). The mixture is stirred for 6 hours at 0° C. and then is allowed to sit in a −5° C. freezer overnight. The next day, 10% aqueous sodium hydroxide solution (10 mL) is added at 0° C. with stirring. Aqueous hydrogen peroxide solution (30%, 1.5 mL) is then added and the mixture is allowed to stir at room temperature for 2 hours. The biphasic mixture is diluted with water (50 mL). The two layers are partitioned and the aqueous phase is saturated with potassium carbonate and then extracted thrice with diethyl ether. The combined extracts are washed with saturated aqueous sodium chloride solution, dried over anhydrous sodium sulfate, and concentrated under reduced pressure to give a bright golden oil, which is purified by flash chromatography (silica gel, hexanes/ethyl acetate). A light yellow solid (0.60 g, 72%) is provided. MS (ES$^+$): (M+H)=206.0

REFERENCE EXAMPLE 4

(1S)-2-phenyl-1-(1,3-thiazol-2-yl)ethylamine

Following the method of Itako et al. (Irako, N.; Hamada, Y.; Shioiri, T. *Tetrahedron* 48(35), 1992, 7251-7264), a solution of (1R)-2-phenyl-1-(1,3-thiazol-2-yl)ethanol (1.3 g, 6.3 mmol, from Reference Example 3) in tetrahydrofuran (60 mL) is cooled to 0° C. (ice-water bath). To the solution is added successively triphenylphosphine (1.8 g, 6.9 mmol), diethylazodicarboxylate (1.1 mL, 6.9 mmol), and diphenylphosphoryl azide (DPPA, 1.6 mL, 6.9 mmol). Following the addition of reagents, the reaction mixture is allowed to warm to room temperature and stir for 47 hours. Following this period, the mixture is concentrated under reduced pressure and purified by flash chromatography (silica gel, hexanes/toluene/diethyl ether) to give 1.2 g of (1S)-2-phenyl-1-(1,3-thiazol-2-yl)ethylazide as a pale blond oil contaminated with DPPA (detected by $^1$H NMR).

To a 55° C. (oil bath) solution of triphenylphosphine (1.6 g, 6.3 mmol) in tetrahydrofuran (10 mL) is added (1S)-2-phenyl-1-(1,3-thiazol-2-yl)ethylazide (contaminated with DPPA, 1.2 g, 5.2 mmol) as a solution in tetrahydrofuran (10 mL). The reaction mixture is allowed to stir for 2 hours at this temperature when aqueous ammonium hydroxide (14 mL) is added. Stirring at 55° C. is continued for 3 hours before the reaction mixture is stored in a −5° C. freezer overnight. The next morning, the reaction mixture is diluted with water (80 mL) and extracted twice with diethyl ether. The combined extracts are washed with 10% aqueous hydrochloric acid (70 mL). The acidic aqueous phase is cooled in an ice-water bath and then basified with 10% aqueous sodium hydroxide to pH 12. The basic phase is then extracted thrice with dichloromethane. The combined extracts are dried over anhydrous magnesium sulfate, filtered, and concentrated under reduced pressure to provide a 0.67 g (52% over 2 steps) of a slightly blond oil. MS (ES$^+$): (M+H)=205.0

REFERENCE EXAMPLE 5

Tert-butyl (2S)-2-{(1R,2R)-1-hydroxy-2-methyl-3-[(4R,5S)-4-methyl-2-oxo-5phenyl-1,3-oxazolidin-3-yl]-3-oxopropyl}pyrrolidine-1-carboxylate In following the procedure of Shioiri et al. (Shioiri, T.; Hayashi, K.; Hamada, Y. *Tetrahedron*. 49(9), 1993, 1913-1924), to a 0° C. (ice-water bath) solution of (4R,5S)-4-methyl-5-phenyl-3-propionyl-2-oxazolidinone (6.4 g, 27 mmol, Fluka) in dichloromethane (110 mL) is added triethylamine (4.3 mL, 31 mmol). Di-n-butylboron triflate (1.0 M solution in dichloromethane, 29 mL, Aldrich) is added dropwise and the resulting mixture is allowed to stir for 45 minutes at 0° C., then cooled to −78° C. (dry ice/acetone bath). N-(tert-butoxycarbonyl)-L-prolinal (3.1 g, 16 mmol, Omega) is added dropwise as a solution in dichloromethane (16 mL) and the reaction mixture is allowed to stir for 2 hours at −78° C. The reaction vessel is then stored in a 0° C. freezer overnight. The next morning, the reaction mixture is warmed to room temperature over 15 minutes and then quenched by the addition of pH 7 phosphate buffer (55 mL) followed by methanol (80 mL). The mixture is then cooled to 0° C. (ice-water bath) and 30% hydrogen peroxide-methanol (1:2, 96 mL) is added dropwise to keep the internal temperature less than 10° C. After stirring for 1 hour in an ice-water bath, to the reaction mixture is added water (55 mL). Volatiles are removed under reduced pressure and the aqueous residue is extracted thrice with diethyl ether. The combined extracts are washed with 1 M potassium bisulfate solution, water, saturated aqueous sodium bicarbonate solution, and saturated aqueous sodium chloride solution, dried over anhydrous sodium sulfate, and concentrated under reduced pressure. The crude viscous pale yellow oil (9.5 g) is purified by flash chromatography (hexanes/ethyl acetate) to give 4.6 g (67%) of a white foam. MS (ES$^+$): (M+H)=433.3

EXAMPLE 29

N,β,β-trimethyl-L-phenylalanyl-N$^1$-{(1S,2E)-1-isopropyl-4-[(2S)-2-((1R,2R)-1-methoxy-2-methyl-3-oxo-3-{[(1S)-2-phenyl-1-(1,3-thiazolyl-2-yl)ethyl]amino}propyl)pyrrolidin-1-yl]-3-methyl-4-oxobut-2-dimethyl-L-valinamide In following the procedure of Shioiri et al. (Shioiri, T.; Hayashi, K.; Hamada, Y. *Tetrahedron* 49(9), 1993,1913-1924), to a 0° C. (ice-water bath) solution of tert-butyl (2S)-2-{(1R,2R)-1-hydroxy-2-methyl-3-[(4R,5S)-4-methyl-2-oxo-5-phenyl-1,3-oxazolidin-3-yl]-3-oxopropyl}pyrrolidine-1-carboxylate (0.89 g, 2.1 mmol, from Reference Example 5) is added dropwise aqueous hydrogen peroxide solution (30%, 1.1 mL, 11 mmol), followed by 0.4 M aqueous lithium hydroxide solution (11 mL, 4.2 mmol). After 2½ hours of stirring at 0° C., 1 M aqueous sodium sulfite solution (12 mL) is added dropwise, and the quenched reaction mixture is stirred over the weekend at room temperature. The mixture is poured into ice-cold saturated aqueous sodium bicarbonate solution (80 mL) and extracted thrice with dichloromethane to remove the chiral auxiliary. The basic aqueous phase is cooled to 0° C., acidified to pH 2 with 1 M aqueous potassium bisulfate solution, saturated with sodium chloride, and extracted thrice with diethyl ether. The combined extracts are washed with water and saturated aqueous sodium chloride solution, dried over anhydrous sodium sulfite, and concentrated under reduced pressure to give (2R,3R,2'S)-3-(N-tert-butoxycarbonyl-2'-pyrrolidinyl)-3-hydroxy-2-methylpropanoic acid as a flocculent white solid (0.56 g, 98%).

In following the procedure of Shioiri et al. (Shioiri, T.; Hayashi, K.; Hamada, Y. *Tetrahedron*. 49(9), 1993, 1913-1924), to a solution of (2R,3R,2'S)-3-(N-tert-butoxycarbonyl-2'-pyrrolidinyl)-3-hydroxy-2-methylpropanoic acid (0.56 g, 2.0 mmol) in tetrahydrofuran (10 mL) is added iodomethane (1.9 mL, 30 mmol). The mixture is cooled to 0° C. (ice-water bath) while stirring under a nitrogen atmosphere. Sodium hydride (60% dispersion in mineral oil, 0.32 g, 8.0 mmol) is added in portions to keep the reaction mixture from frothing excessively. Stirring is continued for 2 hours at 0° C. and then the reaction vessel is stored for 3 days in a –5° C. freezer. The mixture is quenched by the addition of saturated aqueous sodium bicarbonate solution (20 mL) and then extracted with ether to remove impurities and mineral oil. The basic aqueous phase is acidified to pH 2 with 1 M potassium bisulfate solution and then extracted twice with ethyl acetate. The combined extracts are washed with 5% aqueous sodium thiosulfite solution and saturated aqueous sodium chloride solution, dried over anhydrous sodium sulfite, and concentrated under reduced pressure to give (2R,3R,2'S)-3-(N-tert-butoxycarbonyl-2'-pyrrolidinyl)-3-methoxy-2-methylpropanoic acid (Boc-(2R,3R,4S)-dolaproine) as a clear, colorless semisolid (0.41 g, 72%).

In following the procedure of Shioiri et al. (Shioiri, T.; Hayashi, K.; Hamada, Y. *Tetrahedron*. 49(9), 1993, 1913-1924), a solution of (1S)-2-phenyl-1-(1,3-thiazol-2-yl)ethylamine (0.20 g, 1.0 mmol, from Reference Example 4) and (2R,3R,2'S)-3-(N-tert-butoxycarbonyl-2'-pyrrolidinyl)-3-methoxy-2-methylpropanoic acid (0.28 g, 1.0 mmol) in anhydrous dimethylformamide (3 mL) is cooled to 0° C. (ice-water bath) while stirring under a nitrogen atmosphere. Diethyl cyanophosphonate (0.16 mL, 1.05 mmol) is added dropwise via syringe, followed by triethylamine (0.14 mL, 1.0 mmol). Stirring is continued for two hours at room temperature and then at room temperature for three days. The reaction mixture is diluted with 30 mL of ethyl acetate/toluene (2:1) and washed with 1 M aqueous potassium bisulfate solution, water, saturated aqueous sodium bicarbonate solution, and saturated aqueous sodium chloride solution. The organic phase is dried over anhydrous sodium sulfate, decanted, and concentrated under reduced pressure to give 0.47 g (100%) of Boc-(2R,3R,4S)-dolaproine-(S)-dolaphenine as a light yellow foam.

To a solution of crude Boc-(2R,3R,4S)-dolaproine-(S)-dolaphenine (0.23 g, 0.49 mmol) in dichloromethane (1.5 mL) is added trifluoroacetic acid (0.45 mL). The reaction mixture is allowed to stir at room temperature over the weekend. The solvent and excess trifluoroacetic acid are removed under reduced pressure. The crude product is combined with that from an identical run and purified by reverse-phase HPLC (Prodigy ODS3 column, acetonitrile/water) to give 0.18 g (50% for 2 runs) of (2R,3R,4S)-dolaproine-(S)-dolaphenine as a white solid.

A mixture of N,β,β-trimethyl-L-phenylalanyl-N$^1$-[(1S,2E)-3-carboxy-1-isopropylbut-2-enyl]-N$^1$,3-dimethyl-L-valinamide (94 mg, 0.20 mmol, WO 99/32509) and (2R,3R,4S)-dolaproine-(S)-dolaphenine (66 mg, 0.18 mmol) in anhydrous dimethylformamide (1 mL) are reacted with diethyl cyanophosphonate (33 μL, 0.22 mmol) in the presence of triethylamine (31 μL, 0.22 mmol). After stirring for 2 days, the reaction mixture is quenched with a few drops of water and immediately purified by reverse-phase HPLC (Prodigy ODS3 column, acetonitrile/water/trifluoroacetic acid) to give the title compound as a TFA salt (84 mg). MS (ES$^+$): (M+H) 829.6

EXAMPLE 30

N,β,β-trimethyl-L-phenylalanyl-N$^1$-((1S,2E)-4-{(2S)-2-[(1R,2R)-1,3-dimethoxy-2-methyl-3-oxopropyl]pyrrolidin-1-yl}-1-isopropyl-3-methyl-4-oxobut-2-enyl)-N$^1$,3-dimethyl-L-valinamide To a 0° C. (ice-water bath) solution of (2R,3R,2'S)-3-(N-tert-butoxycarbonyl-2'-pyrrolidinyl)-3-methoxy-2-methylpropanoic acid (0.20 g, 0.70 mmol, from Example 29) in methanol (2 mL) and diethyl ether (1 mL) is added trimethylsilyl diazomethane (2.0 M in hexanes, approx. 0.5-0.6 mL, Aldrich) until the yellow color of the reagent persisted. Then the reaction mixture is allowed to stir at room temperature for 10 minutes, after which the volatiles are removed under reduced pressure to a give 0.21 g (>100%) of crude methyl (2R,3R,2'S)-3-(N-tert-butoxycarbonyl-2'-pyrrolidinyl)-3-methoxy-2-methylpropanoate.

Without further purification, crude methyl (2R,3R,2'S)-3-(N-tert-butoxycarbonyl-2'-pyrrolidinyl)-3-methoxy-2-methylpropanoate (0.21 g, 0.70 mmol max.) is taken up in dioxane (1 mL). To the solution, hydrochloric acid (4N in dioxanes, 2 mL, Aldrich) is added, and the resulting mixture is allowed to stir overnight under a nitrogen atmosphere. The next morning, the dioxane solvent is evaporated under reduced pressure to leave methyl (2R,3R,2'S)-3-(2'-pyrrolidinyl)-3-methoxy-2-methylpropanoate hydrochloride as a straw-colored oil (0.21 g,>100%), which is used in the next step without further purification.

Using General Procedure Method A, to a solution of N,β,β-trimethyl-L-phenylalanyl-N$^1$-[(1S,2E)-3-carboxy-1-isopropylbut-2-enyl]-N$^1$,3-dimethyl-L-valinamide (0.40 g, 0.84 mmol, WO 99/32509) and methyl (2R,3R,2'S)-3-(2'-pyrrolidinyl)-3-methoxy-2-methylpropanoate hydrochloride (0.70 mmol max) in anhydrous dimethylformamide (7 mL), is added hydroxybenzotriazole (0.19 g, 1.4 mmol), 1-(3-dimethylaminopropyl)-3-ethylcarbodiimide hydrochloride (0.27 g, 1.4 mmol), and N-methylmorpholine (0.15 mL, 1.4 mmol) under an inert atmosphere. The resulting mixture is stirred overnight at room temperature under an inert atmosphere. The mixture is diluted with water, and the aqueous layer is extracted with diethyl ether (3 times). The combined extracts are washed with saturated aqueous sodium bicarbonate solution and saturated aqueous sodium chloride. The extracts are dried over anhydrous sodium sulfate, filtered and concentrated in vacuo to give 0.57 g (>100%) of crude product, of which 0.24 g is purified on reverse-phase HPLC (Prodigy ODS3, acetonitrile/water/trifluoroacetic acid) to give 100 mg of the title compound as a TFA salt. TOF MS (ES$^+$): (M+H)=657.2

EXAMPLE 31

N-methyl-3-phenyl-L-valyl-N$^1$— [(1S,2E)-1-isopropyl-4-((2S)-2-{(1R,2R)-1-methoxy-2-methyl-3-oxo-[(2-phenethyl)amino]propyl}pyrrolidin-1-yl)-3-methyl-4-oxobut-2-enyl]-N$^1$,3-dimethyl-L-valinamide (2R,3R,2'S)-3-(N-tert-butoxycarbonyl-2'-pyrrolidinyl)-3-methoxy-2-methylpropanoic acid (0.20 g, 0.70 mmol, from Example 29) is coupled to phenethylamine (0.18 mL, 1.4 mmol) using General Procedure I Method A to give 2-(1-methoxy-2-phenethyloxycarbonyl-propyl)-pyrrolidine-1-carboxylic acid tert-butyl ester (0.29 g,>100%) as viscous light brown oil.

Without further purification, 2-(1-Methoxy-2-phenethyloxycarbonyl-propyl)-pyrrolidine-1-carboxylic acid tert-butyl ester (0.29 g, 0.70 mmol maximum) is taken up in dioxane (2 mL). To the solution is added hydrochloric acid (4N in dioxanes, 3 mL, 12 mmol). The reaction mixture is stirred for two days at room temperature and then concentrated under reduced pressure to give the deprotected product (0.31 g, 0.70 mmol maximum) as a yellow semi-solid.

Without further purification, the crude material from the previous reaction (0.70 mmol maximum) is coupled to N,β,β-trimethyl-L-phenylalanyl-N$^1$[(1S,2E)-3-carboxy-1-isopropylbut-2-enyl]-N$^1$,3-dimethyl-L-valinamide (0.36 g, 0.77 mmol) using General Procedure I Method A. A portion of the crude product is purified by reverse-phase HPLC (Prodigy ODS3 column, acetonitrile/water/formic acid) to give the title compound (160 mg) as a formic acid salt. MS (ES$^+$): (M+H)=746.4

EXAMPLE 32

N,β,β-trimethyl-L-phenylalanyl-N$^1$-[(1S,2E)-1-isopropyl-4-((2S)-2-{(1R,2R)-1-methoxy-2-methyl-3-[(4R,5S)-4-methyl-2-oxo-5-phenyl-1,3-oxazolidin-3-yl]-3-oxopropyl}pyrrolidin-1-yl)-3-methyl-4-oxovalinamide Following a literature method (Diem, M. J.; Burow, D. F.; Fry, J. L. *Journal of Organic Chemistry* 42(10), 1977, 1801-1802), to a solution of tert-butyl (2S)-2-{(1R,2R)-1-hydroxy-2-methyl-3-[(4R,5S)-4-methyl-2-oxo-5-phenyl-1,3-oxazolidin-3-yl]-3-oxopropyl}pyrrolidine-1-carboxylate (0.70 g, 1.6 mmol, from Reference Example 5) in anhydrous dichloromethane (5 mL) is added N,N,N',N'-tetramethyl-1,8-naphthalenediamine (0.62 g, 2.9 mmol), followed by trimethyloxonium tetrafluoroborate (0.35 g, 2.4 mmol). The resulting reaction mixture is stirred for 24 hours at room temperature, quenched by the addition of ice water (25 mL), and then filtered through a diatomaceous earth pad. The filtrate is evaporated under reduced pressure and then partitioned between diethyl ether and water. The aqueous phase is extracted thrice with diethyl ether. The combined organic extracts are washed with 1 M aqueous potassium bisulfate solution, water, saturated aqueous sodium bicarbonate solution, and saturated aqueous sodium chloride solution, dried over anhydrous sodium sulfate, and concentrated under reduced pressure to give 0.69 g (97%) of tert-butyl (2S)-2-{(1R,2R)-1-methoxy-2-methyl-3-[(4R,5S)-4-methyl-2-oxo-5-phenyl-1,3-oxazolidin-3-yl]-3-oxopropyl}pyrrolidine-1-carboxylate as a foam.

Without further purification, crude tert-butyl (2S)-2-{(1R,2R)-1-methoxy-2-methyl-3-[(4R,5S)-4-methyl-2-oxo-5-phenyl-1,3-oxazolidin-3-yl]-3-oxopropyl}pyrrolidine-1-carboxylate is dissolved in anhydrous dichloromethane (5 mL). Trifluoroacetic acid (TFA, 1 mL) is added and the resulting reaction mixture is stirred for 4 hours at room temperature. Excess TFA and solvent are evaporated under reduced pressure, and the crude product is purified by reverse-phase HPLC (Prodigy ODS3 column, acetonitrile/water) to give 0.41 g (76%) of (2S)-2-{(1R,2R)-1-methoxy-2-methyl-3-[(4R,5S)-4-methyl-2-oxo-5-phenyl-1,3-oxazolidin-3-yl]-3-oxopropyl}pyrrolidine as a hard white foam.

Using General Procedure I Method A, N,β,β-trimethyl-L-phenylalanyl-N$^1$-[(1S,2E)-3-carboxy-1-isopropylbut-2-enyl]-N$^1$,3-dimethyl-L-valinamide (0.23 g, 0.49 mmol) is coupled to (2S)-2-{(1R,2R)-1-methoxy-2-methyl-3-[(4R,5S)-4-methyl-2-oxo-5-phenyl-1,3-oxazolidin-3-yl]-3-oxopropyl}pyrrolidine (0.17 g, 0.49 mmol). A portion of the crude material is purified by reverse-phase HPLC (Prodigy ODS3 column, acetonitrile/water/trifluoroacetic acid) to give 93 mg of the TFA salt of the title compound as a white powder. MS (ES$^+$): (M+H)=802.4

EXAMPLE 33

Methyl N,β,β-trimethyl-L-phenylalanyl-3-methyl-L-valyl-N-methyl-L-valyl-L-prolinate Using General Procedure I Method A, (2S)-(tert-Butoxycarbonyl-methyl-amino)-3-methyl-butyric acid (0.37 g, 1.6 mmol) is coupled to L-proline methyl ester hydrochloride (0.26 g, 1.6 mmol) to give 1-[2-(tert-butoxycarbonyl-methyl-amino)-3-methyl-butyryl]-pyrrolidine-2-carboxylic acid methyl ester (0.51 g, 93%) as a white solid.

Without further purification, this material is taken up in anhydrous dichloromethane (5 mL). Trifluoroacetic acid (1.4 mL) is added to the solution, which is then allowed to stir for 2 days at room temperature. Volatiles are evaporated under reduced pressure to give 1-(3-methyl-2-methylamino-butyryl)-pyrrolidine-2-carboxylic acid methyl ester.

To a solution of (2S)-(tert-butoxycarbonyl-methyl-amino)-tert-leucine (0.69 g, 3.0 mmol) and the crude material from the previous step (0.54 g, 1.5 mmol maximum) in anhydrous dichloromethane (7 mL) is added benzotriazole-1-yloxy-tris-pyrrolidinophosphonium hexafluorophosphate (PyBOP, 1.2 g, 2.4 mmol) and diisopropylethylamine (0.86 mL, 5.1 mmol) under an inert atmosphere. The resulting reaction mixture is stirred at room temperature for 3 days. The mixture is diluted ethyl acetate/toluene (2:1) and washed with 1M potassium bisulfate solution, water, saturated aqueous sodium bicarbonate solution, and saturated aqueous sodium chloride, dried over anhydrous sodium sulfate, filtered and concentrated in vacuo. The residue, 1-{2-[(2-tert-butoxycarbonylamino-3,3-dimethyl-butyryl)-methyl-amino]-3-methyl-butyryl}-pyrrolidine-2-carboxylic acid methyl ester, a dark straw colored oil, is submitted to the next step without further purification.

The crude material (1.5 mmol maximum) from the previous step is taken up in anhydrous dichloromethane (10 mL). Trifluoroacetic acid (2 mL) is added to the solution, which is then allowed to stir for 2.5 hours at room temperature. Excess trifluoroacetic acid and dichloromethane are evaporated under reduced pressure and the residue is purified by reverse-phase HPLC (Prodigy ODS3 column, acetonitrile/water) to give 1-{2-[(2-amino-3,3-dimethyl-butyryl)-methyl-amino]-3-methyl-butyryl}-pyrrolidine-2-carboxylic acid methyl ester (0.50 g, 94% over three steps) as a hard white foam.

Using General Procedure I Method A, the product from the previous reaction (0.50 g, 1.4 mmol) is coupled to (2S)-2-[(tert-butoxycarbonyl)(methyl)amino]-3-methyl-3-phenylbutanoic acid (0.43 g, 1.4 mmol) to give 1-[2-({2-[2-(tert-butoxycarbonyl-methyl-amino)-3-methyl-3-phenyl-butyrylamino]-3,3-dimethyl-butyryl}-methyl-amino)-3-methyl-butyryl]-pyrrolidine-2-carboxylic acid methyl ester. The crude coupling product is submitted to the following step without further purification. The material (0.7 mmol maximum) from the previous step is taken up in anhydrous dichloromethane (5 mL). Trifluoroacetic acid (1.5 mL) is added to the solution, which is then allowed to stir for 4 hours at room temperature. Excess trifluoroacetic acid and dichloromethane are evaporated under reduced pressure and the residue is purified by reverse-phase HPLC (Prodigy ODS3 column, acetonitrile/water/trifluoroacetic acid) to give 0.24 g of the TFA salt of the title compound as a hard white foam. MS (ES$^+$): (M+H)=545.4

EXAMPLE 34

N,β,β-trimethyl-L-phenylalanyl-3-methyl-L-valyl-N-methyl-L-valyl-L-prolyl-N-benzyl-L-prolinamide To a solution of methyl N,β,β-trimethyl-L-phenylalanyl-3-methyl-L-valyl-N-methyl-L-valyl-L-prolinate (0.7 mmol maximum, from Example 33) in tetrahydrofuran (2 mL), methanol (2 mL), and water (1 mL) is added lithium hydroxide monohydrate (50 mg). The reaction mixture is stirred in a 45° C. oil bath overnight. On the following day, the reaction mixture is allowed to cool to room temperature. Following concentration under reduced pressure, the crude product is purified by reverse-phase HPLC (Prodigy ODS3 column, acetonitrile/water/trifluoroacetic acid) to give 0.22 mg of the trifluoroacetic acid salt of N,β,β-trimethyl-L-phenylalanyl-3-methyl-L-valyl-N-methyl-L-valyl-L-proline as a white powder.

Using General Procedure I Method A, N-(tert-butoxycarbonyl)-L-proline (1.0 g, 4.6 mmol) is coupled to benzylamine (0.55 g, 5.1 mmol) to give 1.2 g (86%) of 2-benzylcarbamoyl-pyrrolidine-1-carboxylic acid tert-butyl ester, which is submitted to the following step without further purification.

A sample of the material from the previous step (0.43 g, 1.4 mmol) is dissolved in dioxane (2 mL), and to the solution is added hydrochloric acid (4N in dioxanes, 3 mL, 12 mmol). The reaction mixture is allowed to stir for 2 hours at room temperature and then concentrated under reduced pressure to provide a viscous blond oil. Ether is added and evaporated sequentially three times to give N-benzyl-L-prolinamide hydrochloride as a pale yellow paste.

Using General Procedure I Method A, N-benzyl-L-prolinamide hydrochloride (0.18 g, 0.76 mmol) is coupled to the trifluoroacetic acid salt of N,β,β-trimethyl-L-phenylalanyl-3-methyl-L-valyl-N-methyl-L-valyl-L-proline (0.11 g, 0.15 mmol, WO 99/32509). After stirring overnight at room temperature, the reaction mixture is purified without an aqueous workup by reverse-phase HPLC (acetonitrile/water/trifluoroacetic acid) to give 0.12 g (92%) of the trifluoroacetic acid salt of the title compound as a pale yellow foam. MS (ES$^+$): (M+H)=717.5

EXAMPLE 35

N,β,β-trimethyl-L-phenylalanyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide Following General Procedure I Method C, N,β,β-trimethyl-L-phenylalanyl-N$^1$-[(1S,2E)-3-carboxy-1-isopropyl-but-2-enyl]-N$^1$,3-dimethyl-L-valinamide (0.267 g, 0.565 mmol) and L-proline methylester hydrochloride salt (0.112 g, 0.678 mmol, Fluka) are coupled to give the trifluoroacetic acid salt of the title compound as a yellow oil, 0.17 g (51% yield), MS m/z 585.3 (M+H).

EXAMPLE 36

N,β,β-trimethyl-L-phenylalanyl-N$^1$-{(1S,2E)-4-[(2S)-2-carboxypyrrolidin-1-yl]-1-isopropyl-3-methyl-4-oxobut-2-enyl}-N$^1$,3-dimethyl-L-valinamide Following General Procedure II N,β,β-trimethyl-L-phenylalanyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide (0.146 g, 0.25 mmol) from Example 35 is hydrolyzed and the product isolated by HPLC (0.01% trifluoroacetic acid in water/acetonitrile) to give the trifluoroacetic acid salt of the title compound as white crystals, 0.014 g. MS: m/z 571.4 (M+H)

EXAMPLE 37

N,β,β-trimethyl-L-phenylalanyl-N$^1$-{(1S,2E)-4-[(2S)-2-(2-phenethoxycarbonyl)pyrrolidin-1-yl]-1-isopropyl-3-methyl-4-oxobut-2-enyl}-N$^1$,3-dimethyl-L-valinamid To a solution of N,β,β-trimethyl-L-phenylalanyl-N$^1$-{(1S, 2E)-4-[(2S)-2-carboxypyrrolidin-1-yl]-1-isopropyl-3-methyl-4-oxobut-2-enyl}-N$^1$,3-dimethyl-L-valinamide (0.089 g, 0.156 mmol, from Example 36) hydroxybenzotriazole (0.025 g, 0.187 mmol) and 1-(3-dimethylaminopropyl)-3-ethylcarbodiimine hydrochloride (0.042 mg, 0.22 mmol) in anhydrous dimethylformamide (0.5 ml) is added diisopropylethylamine (0.054 ml, 0.312 mmol) under an inert atmosphere. To this solution is added a solution of phenethylamine (0.023 g, 0.187 mmol) in anhydrous dimethylformamide (0.5 ml). The resulting reaction mixture is stirred at room temperature overnight. The solvent is removed in vacuo. The residue is chromatographed by HPLC (0.01% trifluoroacetic acid in water/acetonitrile) to give the trifluoroacetic acid salt of the title compound as white crystals, 0.052 g (50% yield). MS: m/z 674.6 (M+H)

EXAMPLE 38

N,β,β-trimethyl-L-phenylalanyl-N$^1$-((1S,2E)-4-{4-[3-(dimethylamino)propyl]piperazin-1-yl}-1-isopropyl-3-methyl-4-oxobut-2-enyl)-N$^1$,3-dimethyl-L-valinamide Following General Procedure I Method C, N,β,β-trimethyl-L-phenylalanyl-N$^1$-[(1S,2E)-3-carboxy-1-isopropyl-but-2-enyl]-N$^1$,3-dimethyl-L-valinamide (0.190 g, 0.402 mmol) and 1-(3-dimethylaminopropyl)-piperazine (0.0825 g, 0.482 mmol) are coupled to give the trifluoroacetic acid salt of the title compound as a white solid, 0.091 g (36% yield), MS m/z 627.6 (M+H)

EXAMPLE 39

N,β,β-trimethyl-L-phenylalanyl-N$^1$-[(1S,2E)-4-(4-benzylpiperazin-1-yl)-1-isopropyl-3-methyl-4-oxobut-2-enyl]-N$^1$,3-dimethyl-L-valinamide Following General Procedure I Method C, N,β,β-trimethyl-L-phenylalanyl-N$^1$-[(1S,2E)-3-carboxy-1-isopropyl-but-2-enyl]-N$^1$,3-dimethyl-L-valinamide (0.239 g, 0.505 mmol) and 1-benzylpiperazine (0.107 g, 0.606 mmol, Aldrich) are coupled to give the trifluoroacetic acid salt of the title compound as a white crystals, 0.378 g, MS m/z 632.5 (M+H)

EXAMPLE 40

N,β,β-trimethyl-L-phenylalanyl-N$^1$-{(1S,2E)-4-[(2S,4R)-2-(methoxycarbonyl)-4-hydroxypyrrolidin-1-yl]-1-isopropyl-3-methyl-4-oxobut-2-enyl}-N$^1$,3-dimethyl-L-valinamide Following General Procedure I Method C, N,β,β-trimethyl-L-phenylalanyl-N$^1$-[(1S,2E)-3-carboxy-1-isopropyl-but-2-enyl]-N$^1$,3-dimethyl-L-valinamide (0.270 g, 0.571 mmol) and L-trans-4-hydroxyproline methyl ester hydrochloride salt (0.099 g, 0.685 mmol, Advance ChemTech) are coupled to give the trifluoroacetic acid salt of the title compound as a white solid 0.2162 g (62% yield), MS m/z 601.4 (M+H)

EXAMPLE 41

N,β,β-trimethyl-L-phenylalanyl-N$^1$-{(1S,2E)-4-[(2R)-2-(methoxycarbonyl)pyrrolidin-1-yl]-1-isopropyl-3-methyl-4-oxobut-2-enyl}-N$^1$,3-dimethyl-L-valinamide Following General Procedure I Method C, N,β,β-trimethyl-L-phenylalanyl-N$^1$-[(1S,2E)-3-carboxy-1-isopropyl-but-2-enyl]-N$^1$,3-dimethyl-L-valinamide (0.224 g, 0.47 mmol) and D-proline methyl ester hydrochloride salt (0.094 g, 0.57 mmol) are coupled to give the trifluoroacetic acid salt of the title compound as a white solid 0.196 g (58% yield), MS m/z 585.5 (M+1)

EXAMPLE 42

N,β,β-trimethyl-L-phenylalanyl-N$^1$-{(1S,2E)-4-[(2S,4R)-2-carboxy-4-hydroxypyrrolidin-1-yl]-1-isopropyl-3-methyl-4-oxobut-2-enyl}-N$^1$,3-dimethyl-L-valinamide Following General Procedure II N,β,β-trimethyl-L-phenylalanyl-N$^1$-{(1S,2E)-4-[(2S,4R)-2-(methoxycarbonyl)-4-hydroxypyrrolidin-1-yl]-1-isopropyl-3-methyl-4-oxobut-2-enyl}-N$^1$,3-dimethyl-L-valinamide (0.133 g, 0.221 mmol) from Example 40 is hydrolyzed and the product isolated by HPLC (0.01% trifluoroacetic acid in water/acetonitrile) to give the trifluoroacetic acid salt of the title compound as a light yellow solid, 0.078 g (60% yield), MS: m/z 585.3 (M−H)

EXAMPLE 43

N,β,β-trimethyl-L-phenylalanyl-N$^1$-{(1S,2E)-4-[(2R)-2-carboxypyrrolidin-1-yl]-1-isopropyl-3-methyl-4-oxobut-2-enyl}-N$^1$,3-dimethyl-L-valinamide Following General Procedure II, N,β,β-trimethyl-L-phenylalanyl-N$^1$-{(1S,2E)-4-[(2R)-2-(methoxycarbonyl)pyrrolidin-1-yl]-1-isopropyl-3-methyl-4-oxobut-2-enyl}-N$^1$,3-dimethyl-L-valinamide (0.159g, 0.273 mmol) from Example 41 is hydrolyzed and the product isolated by HPLC (0.01% trifluoroacetic acid in water/acetonitrile) to give the trifluoroacetic acid salt of the title compound as a white solid, 0.138 g (88% yield), MS: m/z 569.4 (M−1)

EXAMPLE 44

3-cyclohexyl-N-methyl-L-valyl-N$^1$-{(1S,2E)-1-isopropyl-4-[(2S)-2-((1R,2R)-1methoxy-2-methyl-3-oxo-3-{[(1S)-2-phenyl-1-(1,3-thiazol-2-yl)ethyl]amino}propyl)pyrrolidin-1-yl]-3-methyl-4-oxobut-2-enyl}-N$^1$,3-dimethyl-L-valinamide Following General Procedure I Method C, 3-cyclohexyl-N-methyl-L-valyl-N-1-[(1S,2E)-3-carboxy-1-isopropyl-2-butenyl]-N-1,3-dimethyl-L-valinamide (0.083 g, 0.173 mmol) and (2R,3R,4S)-dolaproine-(S)-dolaphenine (0.077 g, 0.208 mmol, from Example 29) are coupled to give the trifluoroacetic acid salt of the title compound as a white solid 0.064 g (44% yield), MS m/z 835.7 (M+H)

EXAMPLE 45

3-cyclohexyl-N-methyl-L-valyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide Following General Procedure I Method C, 3-cyclohexyl-N-methyl-L-valyl-N-1-[(1S,2E)-3-carboxy-1-isopropyl-2-butenyl]-N-1,3-dimethyl-L-valinamide (0103 g, 0.215 mmol) and L-proline methyl ester hydrochloride salt (0.043 g, 0.257 mmol, Aldrich) are coupled to give the trifluoroacetic acid salt of the title compound as a light yellow solid 0.068 g (53% yield), MS m/z 591.4 (M+1)

EXAMPLE 46

3-cyclohexyl-N-methyl-L-valyl-N$^1$-{(1S,2E)-4-[(2S)-2-carboxypyrrolidin-1-yl]-1-isopropyl-3-methyl-4-oxobut-2-enyl}-N$^1$,3-dimethyl-L-valinamide Following the General Procedure II 3-cyclohexyl-N-methyl-L-valyl-N$^1$-{(1S,2E)-4-[(2S)-2-(methoxycarbonyl)pyrrolidin-1-yl]-1-isopropyl-3-methyl-4-oxobut-2-enyl}-N$^1$,3-dimethyl-L-valinamide (0.091 g, 0.154 mmol, from Example 45) is hydrolyzed and the product isolated by HPLC (0.01% trifluoroacetic acid in water/acetonitrile) to give the trifluoroacetic acid salt of the title compound as white solid, 0.070 g (79% yield), MS: m/z 575.5 (M−H)

EXAMPLE 47

N,β,β-trimethyl-L-phenylalanyl-N$^1$-{(1S,2E)-1-isopropyl-4-[(2S)-2-(methoxycarbonyl)-2,5-dihydro-1H-pyrrol-1-yl]-3-methyl-4-oxobut-2-enyl}-N$^1$,3-dimethyl-L-valinamide To the solution of BOC-3,4-dehydro-L-proline (1.03 g, 4.84 mmol) in diethylether (3 ml) at room temperature is added (trimethylsilyl)diazomethane (6.8 ml, 13.7 mmol). The reaction mixture is stirred at room temperature for 35 minute. Solvent is removed in vacuo. The residue is purified by preparative TLC (2000 micron silica plate, eluted with 3.5:1 hexane/ethyl acetate) to give BOC-3,4-dehydro-L-proline-methyl ester as a colorless oil 0.426 g. Then this oil is treated with 4 N hydrogen chloride in dioxane (11.3 ml, 27.62 mmol) to give 3,4-dehydro-L-proline methyl ester hydrochloride salt. Following General Procedure I Method C, 4-[[(2S)-3,3-Dimethyl-2-[[(2S)-3-methyl-2-(methylamino)-1-oxo-3-phenylbutyl]amino)]-1-oxobutyl]methylamino]-2,5-dimethyl-(E, 4S)-2-hexenoic acid (0.672 g, 1.42 mmol) and 3,4-dehydro-L-proline methyl ester hydrochloride salt (0.281 g, 1.71 mmol,) are coupled to give the trifluoroacetic acid salt of the title compound as a white solid 0.608 g (73% yield), MS m/z 583.4 (M+1)

EXAMPLE 48

N,β,β-trimethyl-L-phenylalanyl-N$^1$-{(1S,2E)-4-[(2S)-2-carboxy-2,5-dihydro-1H-pyrrol-1-yl]-1-isopropyl-3-methyl-4-oxobut-2-enyl}-N$^1$,3-dimethyl-L-valinamide Following General Procedure I Method B, 4-[[(2S)-3,3-Dimethyl-2-[[(2S)-3-methyl-2-(methylamino)-1-oxo-3-phenylbutyl]amino)]-1-oxobutyl]methylamino]-2,5-dimethyl-(E, 4S)-2-hexenoic acid (0.262 g, 0.55 mmol) and 3,4-dehydro-L-proline methyl ester hydrochloride salt (0.099 g, 0.66 mmol,) are coupled to give the trifluoroacetic acid salt of the title compound as a white solid 0.196 g (58% yield), MS m/z 569.3 (M+1)

EXAMPLE 49

N,β,β-trimethyl-L-phenylalanyl-N$^1$-{(1S,2E)-1-isopropyl-4-[(2S)-2-(methoxycarbonyl)piperidin-1-yl]-3-methyl-4-oxobut-2-enyl}-N$^1$,3-dimethyl-L-valinamide Following General Procedure I Method C, 4-[[(2S)-3,3-Dimethyl-2-[[(2S)-3-methyl-2-(methylamino)-1-oxo-3-phenylbutyl]amino)]-1-oxobutyl]methylamino]-2,5-dimethyl-(E, 4S)-2-hexenoic acid (0.476 g, 1.00 mmol) and L-pipecolic acid methyl ester hydrochloride salt (0.099 g, 0.66 mmol,) are coupled to give the trifluoroacetic acid salt of the title compound as a white solid 0.514 g (85% yield), MS m/z 599.3 (M+1)

EXAMPLE 50

N,β,β-trimethyl-L-phenylalanyl-N$^1$-{(1S,2E)-4-[(2S)-2-carboxypiperidin-1-yl]-1-isopropyl-3-methyl-4-oxobut-2-enyl}-N$^1$,3-dimethyl-L-valinamide Following the General Procedure II, N,β,β-trimethyl-L-phenylalanyl-N$^1$-{(1S,2E)-1-isopropyl-4-[(2S)-2-(methoxycarbonyl)piperidin-1-yl]-3-methyl-4-oxobut-2-enyl}-N$^1$,3-dimethyl-L-valinamide (0.241 g, 0.402 mmol) from Example 49 is hydrolyzed and the product isolated by HPLC (0.01% trifluoroacetic acid in water/acetonitrile) to give the trifluoroacetic acid salt of the title compound as white solid, 0.232 g (99% yield), MS: m/z 585.3 (M+H)

EXAMPLE 51

3-cyclohexyl-N-methyl-L-valyl-N$^1$-[(1S,2E)-1-isopropyl-4-((2S)-2-{(1R,2R)-1-meyhoxy-2-methyl-3-[(4R,5S)-4-methyl-2-oxo-5-phenyl-1,3-oxazolidin-3-yl]-3-oxopropyl}pyrrolidin-1-yl)-3-methyl-4-oxobut-2-enyl]-N$^1$,3-dimethyl-L-valinamide Following the diethyl cyanophosphonate coupling procedure described in Example 29, 3-cyclohexyl-N-methyl-L-valyl-N-1-[(1S,2E)-3-carboxy-1-isopropyl-2-butenyl]-N-1,3-dimethyl-L-valinamide (0.135 g, 0.282 mmol) and (2S)-2-{(1R,2R)-1-methoxy-2-methyl-3-[(4R,5S)-4-methyl-2-oxo-5-phenyl-1,3-oxazolidin-3-yl]-3-oxopropyl}pyrrolidine (0.117 g, 0.34 mmol, from Example 32) are coupled to give the title compound as a white solid 0.041 g (18% yield), MS m/z 808.4 (M+1)

EXAMPLE 52

N,β,β-trimethyl-L-phenylalanyl-N$^1$-{(1S,2E)-1-isopropyl-4-[methoxy(methyl)-amino]-3-methyl-4-oxobut-2-enyl}-N$^1$,3-dimethyl-L-valinamide A solution of N,β,β-trimethyl-L-phenylalanyl-N$^1$-[(1S, 2E)-3-carboxy-1-isopropylbut-2-enyl]-N$^1$,3-dimethyl-L-valinamide (473 mg, 1 mmol, WO 99/32509) in tetrahydrofuran (2 mL) is added a solution of N,O-dimethylhydroxylamine hydrochloride (166 mg, 1.7 mmol) in water (2 mL), adjusting the reaction mixture to pH 4.5 by adding dropwise 1.0 N sodium hydroxide solution. To this is added dropwise a solution of 1-(3-dimethylaminopropyl)-3-ethylcarbodiimine hydrochloride (479 mg, 2.5 mmol) in water (7 mL) over a period of 7 min, maintaining pH 4.5 by using 1.0 N sodium hydroxide solution. The reaction mixture is stirred at room temperature for 2.5 h, adjusting the pH to 6-7. To this is added brine (10 mL) and extracted with dichloromethane. The combined organic layers are washed with brine, dried (Na$_2$SO$_4$), filtered and concentrated to give 491 mg (95%) of the title compound as a white solid. HRMS (ESI) calcd for C$_{29}$H$_{48}$N$_4$O$_4$ (M+H$^+$) 517.3748, found 517.3750.

EXAMPLE 53

N,β,β-trimethyl-L-phenylalanyl-N-1-{(1S,2E)-4-[(1, 1'-biphenyl-4-ylmethyl)amino]-1-isopropyl-3-methyl-4-oxobut-2-enyl}-N$^1$,3-dimethyl-L-valinamide Following General Procedure I Method A N,β,β-trimethyl-L-phenylalanyl-N$^1$-[(1S,2E)-3-carboxy-1-isopropylbut-2-enyl]-N$^1$,3-dimethyl-L-valinamide (256 mg, 0.542 mmol, WO 99/32509) and 4-phenylbenzylamine (119 mg, 0.65 mmol) are coupled to give the title compound as a yellow oil, 83 mg, MS: m/z 639.4 (M+1).

EXAMPLE 54

N,β,β-trimethyl-L-phenylalanyl-N¹-((1R,2E)-4-{[4-(benzyloxy)benzyl]oxy}-1-isopropyl-3-methyl-4-oxobut-2-enyl)-N¹,3-dimethyl-L-valinamide A mixture of N,β,β-trimethyl-L-phenylalanyl-N¹-[(1S,2E)-3-carboxy-1-isopropylbut-2-enyl]-N¹,3-dimethyl-L-valinamide (287 mg, 0.607 mmol), 1-(3-dimethylaminopropyl)-3-ethylcarbodiimine hydrochloride (0.728 mmol), 4-(benzyloxy)benzyl alcohol (137 mg, 0.638 mmol) and dimethylaminopyridine (0.12 mmol) in anhydrous dichloromethane (12 mL) are stirred under a nitrogen atmosphere at room temperature for 20 hours. The solvent is removed, the residue taken up in methanol, and the product purified by reverse phase HPLC (0.01% trifluoroacetic acid in water/acetonitrile) to give the title compound as a white gum, 208 mg, MS: m/z 670.4 (M+1).

REFERENCE EXAMPLE 6

Adamantan-1-yl-methylamino-acetic acid

Adamantan-1-yl-iodo-acetic acid (7.86 g, 24.55 mmol, P. A. Krasutskii. et. Al.;J. Org. Chem. USSR (Engl. Trans.); 1985; 1327-1332) is refluxed with 100 mL of 2M methylamine in tetrahydrofuran for 18 hours. The solvent is evaporated in vacuo, and the residue treated with water. The pH is adjusted to 6 and the resulting solid collected and dried to give 2.16 g of the title compound as a white solid. MS: m/z 224.2 (M+1).

REFERENCE EXAMPLE 7

Ethyl (2E,4S)-4-[{N-[(2S)-2-(1-adamantyl)-2-(methylamino)ethanoyl]-3-methyl-L-valy}(methyl)amino]-2,5-dimethyl-2-hexenoate and

REFERENCE EXAMPLE 8

Ethyl (2E,4S)-4-[{N-[(2R)-2-(1-adamantyl)-2-(methylamino)ethanoyl]-3-methyl-L-valy}(methyl)amino]-2,5-dimethyl-2-hexenoate To adamantan-1-yl-methylamino-acetic acid (0.447 g, 2.0 mmol, from Reference Example 6) in dichloromethane (17 mL) is added PyBOP (1.04 g, 2.0 mmol). After 15 min ethyl (2E,4S)-2,5-dimethyl-4-[methyl(3-methyl-L-valyl)amino]hex-2-enoate (0.625 g, 2.0 mmol, WO 99/32509) in dichlormethane (5 mL) is added, followed by diisopropylethylamine (0.75 mL, 4.3 mmol). This is stirred at room temperature overnight. The reaction mixture is evaporated in vacuo and the residue treated with ethyl acetate and water. The ethyl acetate layer is dried over sodium sulfate and purified by hplc. The two diastereomers are partially separated. The first isomer is assigned the SSS configuration and contained 33.4% of the RSS isomer. MS: m/z 518.3 (M+1). The second isomer is assigned the RSS configuration and contained 8.9% of the SSS isomer. MS: m/z 518.3 (M+1).

EXAMPLE 55

(2E,4S)-4-[{N-[(2S)-2-(1-adamantyl)-2-(methylamino)ethanoyl]-3-methyl-L-valyl}(methyl)amino]-2,5-dimethyl-2-hexenoic acid According to General Procedure II ethyl (2E,4S)-4-[{N-[(2S)-2-(1-adamantyl)-2-(methylamino)ethanoyl]-3-methyl-L-valyl}(methyl)amino]-2,5-dimethyl-2-hexenoate (303 mg, 0.59 mmol, from Reference Example 7) in water (1.5 mL) and methanol (6.0 mL) is treated with aqueous 1 M lithium hydroxide solution (2.9 mL, 2.9 mmol) to provide the trifluoroacetic acid salt of the title compound (49 mg) as a white solid after preparative HPLC. MS (ES): m/z 490.24 (M+H).

EXAMPLE 56

(2E,4S)-4-[{N-[(2R)-2-(1-adamantyl)-2-(methylamino)ethanoyl]-3-methyl-L-valyl}(methyl)amino]-2,5-dimethyl-2-hexenoic acid According to General Procedure II ethyl (2E,4S)-4-[{N-[(2R)-2-(1-adamantyl)-2-(methylamino)ethanoyl]-3-methyl-L-valyl}(methyl)amino]-2,5-dimethyl-2-hexenoate (359 mg, 0.69 mmol, from Reference Example 8) in water (1.7 mL) and methanol (7.0 mL) is treated with aqueous 1 M lithium hydroxide solution (3.5 mL, 3.5 mmol) to provide the trifluoroacetic acid salt of the title compound (62 mg) as a white solid after preparative HPLC. MS (ES): m/z 490.24 (M+H).

EXAMPLE 57

(2E,4S)-2,5-dimethyl-4-(methyl{3-methyl-N-[(2S)-2-(methylamino)-2-phenylethanoyl]-L-valyl}amino)-2-hexenoic acid To N-methyl phenylglycine (330 mg, 2.0 mmol) in dichloromethane (15 mL) is added PyBOP (1.04 g, 2.0 mmol). After 15 mins, ethyl (2E,4S)-2,5-dimethyl-4-[methyl(3-methyl-L-valyl)amino]hex-2-enoate (0.624 g, 2.0 mmol, WO 99/32509) in dichlormethane (5 mL) is added followed by diisopropylethylamine (0.8 mL, 4.4 mmol). After 18 h the reaction mixture is concentrated in vacuo and the residue treated with ethyl acetate and water. The ethyl acetate layer is dried over sodium sulfate, filtered and concentrated to give 772 mg of a white solid, MS: m/z 460.46 (M+1). According to General Procedure II this solid (689 mg, 1.5 mmol) in water (3.6 mL) and methanol (15 mL) is treated with aqueous 1 M lithium hydroxide solution (7.5 mL, 7.5 mmol), to provide the trifluoroacetic acid salt of the title compound (541 mg) as a white solid after preparative HPLC. MS (ES): m/z 432.42 (M+H).

EXAMPLE 58

(2E,4S)-2,5-dimethyl-4-(methyl{3-methyl-N-[(2,2,4-trimethylthiomorpholin-3-yl)carbonyl]-L-valyl}amino)hex-2-enoic acid A mixture of 2,2-Dimethyl-thiomorpholine-3-carboxylic acid (3.51 g, 20 mmol, BE 893025), formic acid (5.12 g of 90%) and formalin (4.5 mL of 37%) is heated at reflux for 8 hours. The reaction mixture is then cooled and treated with hydrochloric acid (10 mL of 4N) and evaporated to dryness. A portion of this residue is purified by HPLC to give 2,2,4-trimethyl-thiomorpholine-3-carboxylic acid, which is used as is. 2,2,4-Trimethyl-thiomorpholine-3-carboxylic acid (388 mg, 2.05 mmol) is stirred with dichloromethane (4 mL) and dimethylformamide (4 mL). To this is added (benzotriazol-1-yloxy)tripyrrolidinophosphonium hexafluorophosphate (PyBOP, 1.07 g, 2.05 mmol). After 15 min, ethyl (2E,4S)-2,5-dimethyl-4-[methyl(3-methyl-L-valyl)amino]hex-2-enoate (0.640 g, 2.05 mmol, WO 99/32509) is added in dichlormethane (5 mL) followed by diisopropylethylamine (0.8 mL, 4.4 mmol). This is stirred at room temperature overnight. The reaction mixture is evaporated in vacuo and the residue treated with ethyl acetate and water. The ethyl acetate layer is dried over sodium sulfate, filtered and concentrated. The resulting material (314 mg, 0.65 mmol) is treated with aqueous 1 M lithium hydroxide solution (3.3 mL, 3.3 mmol), water (1.6 mL) and methanol (6.5 mL), to provide the trifluoroacetic acid salt of the title compound as a white solid after preparative HPLC, MS (ES): m/z 456.29 (M+H).

REFERENCE EXAMPLE 9

Ethyl (2Z)-3,4-dihydro-1 (2H)-naphthalenylidene(formylamino)ethanoate

To a stirred slurry of potassium t-butoxide (4.7 g, 42.0 mmol) in 30 mL tetrahydrofuran at 0° C. is added ethyl isocyanoacetate (4.53 g, 40.0 mmol). This is stirred for 30 mins whereupon a solution of β-tetralone (5.88 g, 40.0 mmol) in tetrahydrofuran (20 mL) is added dropwise. The reaction mixture is allowed to warm to room temperature and stirred for 3 hours. The reaction mixture is then recooled in an ice bath and to this is added acetic acid (2.5 g, 41.6 mmol), allowed to warm to room temperature and stirred for an additional 30 mins. The solvent is removed in-vacuo and the residue partitioned between water and ethyl acetate. The organic layer is washed with water and brine, dried over sodium sulfate, filtered, evaporated and crystallized from cyclohexane to give 4.67 g of a white solid (contains some E-isomer), MS: m/z 260.2 (M+1).

REFERENCE EXAMPLE 10

Methyl (1-methyl-1,2,3,4-tetrahydro-1-naphthalenyl) (oxo)acetate

Ethyl (2Z)-3,4-dihydro-1(2H)-naphthalenylidene(formylamino)ethanoate (1.31 g, 5.05 mmol, from Reference Example 9) is refluxed with 6N HCL (10 mL) for 1 hour. The mixture is evaporated, dried and the residue taken up in tetrahydrofuran (8 mL) and water (1.7 mL). To this is added 5 N sodium hydroxide solution (3.6 mL, 18.0 mmol) and iodomethane (0.9 mL, 14.5 mmol). While stirring under a nitrogen atmosphere, the reaction mixture is heated in a 70° C. oil bath for 5½ hours. Additional volumes of 5 N sodium hydroxide solution (2.0 mL) and iodomethane (0.3 mL, 4.8 mmol) are added. The reaction mixture is allowed to stir for 2 days at room temperature, then evaporated in vacuo to remove most of the tetrahydrofuran. This is extracted with ethyl acetate and the organic layer then dried over anhydrous sodium sulfate, filtered, and concentrated in vacuo to give a clear oil, 0.49 g, MS: m/z 233.2 (M+1).

EXAMPLE 59

(2E,4S)-2,5-dimethyl-4-(methyl{3-methyl-N-[(2S)-2-(methylamino)-2-(1-methyl-1,2,3,4-tetrahydro-1-naphthalenyl)ethanoyl]-L-valyl}amino)-2-hexenoic acid and

EXAMPLE 60

(2E,4S)-2,5-dimethyl-4-(methyl{3-methyl-N-[(2R)-2-(methylamino)-2-(1-methyl-1,2,3,4-tetrahydro-1-naphthalenyl)ethanoyl]-L-valyl}amino)-2-hexenoic acid Methyl (1-methyl-1,2,3,4-tetrahydro-1-naphthalenyl) (oxo)acetate (0.400 g, 1.72 mmol, from Reference Example 10) is treated with 1 M lithium hydroxide solution (6.9 mL, 6.9 mmol) and methanol (15 mL) and stirred overnight. The reaction mixture is then acidified and extracted with ethyl acetate, dried over sodium sulfate, filtered and evaporated. The product is dissolved in tetrahydrofuran (4 mL) and treated with methylamine (4.0 mL of 2M in tetrahydrofuran, 8.0 mmol) and stirred for 1 hour then a solution of borane-pyridine complex (0.26 mL of 8M solution, 2.08 mmol) is added. The mixture is heated at 50° C. for 2.5 hours and cooled to room temperature. Methanol (5 mL) is added and the reaction mixture then evaporated to dryness and triturated with tetrahydrofuran to give a white solid. This solid (116 mg, 0.50 mmol) is stirred with dichloromethane (2 mL) and dimethylformamide (2 mL). To this is added PyBOP (0.260 g, 0.50 mmol) and stirred for 15 mins, the BCD ester (0.156 g, 0.50 mmol) is added in dichlormethane (1 mL) followed by diisopropylethylamine (0.2 mL, 1.1 mmol). This is stirred at room temperature overnight. The reaction mixture is evaporated in vacuo and the residue treated with ethyl acetate and water. The ethyl acetate layer is dried over sodium sulfate, filtered and concentrated giving the ester. This ester (169 mg, 0.32 mmol) is treated with aqueous 1M lithium hydroxide solution (1.6 mL, 1.6 mmol), water (0.8 mL) and methanol (3.2 mL), to provide after preparative HPLC two components. The first isomer eluted is arbitrarily assigned as the S-isomer (Example 59) (11 mg of a white solid), MS (ES): m/z 500.32 (M+H). The second component (Example 60) is 43 mg of a white solid, MS (ES): m/z 500.33 (M+H), which has 27% of Example 59 present.

REFERENCE EXAMPLE 11

Ethyl-3-hydroxy-L-valyl-N$^1$-[(1S,2E)-4-ethoxy-1-isopropyl-3-methyl-4-oxo-2-butenyl]-N$^1$-L-valinamide To a cooled (0° C., ice bath) solution of (S)-(+)-2-amino-3-hydroxy-3-methylbutanoic acid (42.7 mg, 0.32 mmol) and benzotriazole-1-yl-oxy-tris-pyrrolidinophosphonium hexafluorophosphate (192.3 mg, 0.37 mmol) in anhydrous dimethylformamide (3-5 ml) is added diisopropylethylamine (0.167 ml, 0.96 mmol). To this solution is added a solution of ethyl (E,4S)-4-[[(2S)-2-amino-3,3-dimethylbutanoyl](methyl)amino]-2,5-dimethyl-2-hexenoate (0.10 g, 0.32 mmol, WO 99/32509) in anhydrous dimethylformamide (3 ml). After stirring at 0° C. for 5-10 minutes, the cooling bath is removed, and the resulting reaction mixture is stirred at room temperature for 15-20 hours. The mixture is diluted with water, and the aqueous layer is extracted with ethyl acetate (3 times). The combined extracts are washed with saturated aqueous sodium chloride, dried over sodium sulfate, filtered and concentrated in vacuo. The residue is chromatographed (silica gel, flash column), to give the title compound as a white solid. (70 mg, 76%). MS (ES) m/z 425.29 [M+H]

EXAMPLE 61

3-hydroxy-N-methyl-L-valyl-N$^1$-[(1S,2E)-4-ethoxy-1-isopropyl-3-methyl-4-oxo-2-butenyl]-N$^1$,3-dimethyl-L-valinamide and 3-hydroxy-N,N-dimethyl-L-valyl-N$^1$-[(1S,2E)-4-ethoxy-1-isopropyl-3-methyl-4-oxo-2-butenyl]-N$^1$,3-dimethyl-L-valinamide To a vigorously stirred solution of ethyl-3-hydroxy-L-valyl-N$^1$-[(1S,2E)-4-ethoxy-1-isopropyl-3-methyl-4-oxo-2-butenyl]-N$^1$-L-valinamide (50 mg, 0.12 mmol, from Reference Example 11) in anhydrous dimethylformamide (1 ml) at 0° C. (ice bath) is added iodomethane (0.017 ml, 0.12 mmol).

After 30 minutes diisopropylethylamine (0.042 ml, 0.24 mmol) is added dropwise. The reaction mixture is allowed to warm to room temperature. After 2 hours water is added and the mixture is acidified by dropwise addition of 1.0M aqueous citric acid. The acidic mixture is extracted 3× with ethyl acetate. The combined organic layers are dried over sodium sulfate and concentrated in vacuo to give a mixture of ethyl 3-hydroxy-N-methyl-L-valyl-$N^1$-[(1S,2E)-4-ethoxy-1-isopropyl-3-methyl-4-oxo-2-butenyl]-$N^1$,3-dimethyl-L-valinamide compound and ethyl-3-hydroxy-N,N-dimethyl-L-valyl-$N^1$-[(1S,2E)-4-ethoxy-1-isopropyl-3-methyl-4-oxo-2-butenyl]-$N^1$,3-dimethyl-L-valinamide. This material (50 mg) is dissolved in methanol (1 ml) and tetrahydrofuran (1 ml). To the resulting solution is added 2.0 M aqueous lithium hydroxide solution (0.1 mL). After 15 hours the volatiles are removed in vacuo, and the residual aqueous mixture is cooled with an ice water bath, and acidified to pH 5.5-6.0 with aqueous 1N aqueous citric acid solution. The resulting precipitate is collect by filtration, and the solid is washed with a cold water, and dried over high vacuum. The crude material is purified by reverse phase HPLC to give the trifluoroacetic acid salt of the title compounds as a white solid (40 mg, 80%). A 1:1 mixture of components is present by analytical HPLC/MS: m/z 3-hydroxy-N-methyl-L-valyl-$N^1$-[(1S,2E)-4-ethoxy-1-isopropyl-3-methyl-4-oxo-2-butenyl]-$N^1$,3-dimethyl-L-valinamide: [M+H] 414.3 3-hydroxy-N,N-dimethyl-L-valyl-$N^1$-[(1S,2E)-4-ethoxy-1-isopropyl-3-methyl-4-oxo-2-butenyl]-$N^1$,3-dimethyl-L-valinamide: [M+H] 428.4

EXAMPLE 62

1-methyl-L-prolyl-$N^1$-[(1S,2E)-3-carboxy-1-isopropylbut-2-enyl]-$N^1$,3-dimethyl-L-valinamide To a solution of N-methyl-L-proline monohydrate (0.26 g, 1.79 mmol) and benzotriazole-1-yl-oxy-tris-pyrrolidino-phosphonium hexafluorophosphate (1.4 g, 2.69 mmol) in anhydrous dichloromethane (3.0 ml) at 25° C. is added diisopropylethylamine (0.63 ml, 3.62 mmol) under an inert atmosphere. To this solution is added a solution of ethyl (2E,4S)-2,5-dimethyl-4-[methyl(3-methyl-L-valyl)amino]hex-2-enoate (0.39 g, 1.27 mmol, WO 99/32509) in anhydrous dichloromethane (2.0 ml). The resulting reaction mixture is stirred at room temperature overnight. The reaction mixture is evaporated in vacuo. The residue (300 mg, 0.78 mmol) is dissolved in methanol (6.85 ml), water (1.8 ml) and tetrahydrofuran (3.25 ml). To this reaction mixture is added aqueous lithium hydroxide solution (3.54 ml, 3.54 mol) The resulting mixture is stirred at room temperature overnight. The reaction mixture is diluted with dichloromethane/water. The organic layer is washed with citric acid, brine, dried over sodium sulfate and filtered. The solvent is removed in vacuo, and the residue is chromatographed by HPLC (0.01% trifluoroacetic acid in water/acetonitrile) to give the product as a yellow oil, 0.08 g (28% yield). MS: m/z 396.28 (M+1)

REFERENCE EXAMPLE 12

N-{1-[(1-Formyl-2-methyl-propyl)-methyl-carbamoyl]-2,2-dimethyl-propyl}-3-methyl-2-methylamino-3-phenyl-butyramide A solution of N,β,β-trimethyl-L-phenylalanyl-$N^1$-[(1S,2E)-3-carboxy-1-isopropylbut-2-enyl]-$N^1$,3-dimethyl-L-valinamide (1.0 g) in methanol (20 mL) is added to 100 mL of methanol (−78° C. which had been treated with ozone until the solution is blue. The resulting colorless reaction mixture is treated with ozone at −78° C. until the blue color remained. After 5 min dimethylsulfide (2 mL) is added. The reaction mixture is allowed to warm to room temperature and then concentrated in vacuo to give the title compound as an oil. MS (ES): m/z 418.4 (M+H).

EXAMPLE 63

N,β,β-trimethyl-L-phenylalanyl-$N^1$-[(1S,2E)-3-(ethoxysulfonyl)-1-isopropylprop-2-enyl]-$N^1$,3-dimethyl-L-valinamide To a solution of ethyl diethylphosphorylmethanesulfonate (260 mg, 1.0 mmol) in anhydrous THF (3 mL) at −78° C. is added n-butyllithium (in hexanes, 0.44 mL, 1.1 mmol). After stirring for 20 min at −78° C., a solution of N-{1-[(1-Formyl-2-methyl-propyl)-methyl-carbamoyl]-2,2-dimethyl-propyl}-3-methyl-2-methylamino-3-phenyl-butyramide (1.0 mmol) in anhydrous THF (7 mL), which is freshly prepared as described in Reference Example 12, is added. The reaction mixture is stirred at −78° C. for additional 30 min, and then gradually warmed to room temperature. After 40 h, the reaction is quenched with water and extracted with $CH_2Cl_2$. The combined organic layers are washed with brine, dried ($Na_2SO_4$), filtered and concentrated. The residue is chromatographed on a silica gel column, eluting with 4:1 $CH_2Cl_2$/EtOAc to give 160 mg (31%) of the title compound as a yellow oil. HRMS (ESI) calcd for $C_{27}H_{45}N_3O_5S$ [M+H] 524.3153, found 524.3157.

EXAMPLE 64

N,β,β-trimethyl-L-phenylalanyl-$N^1$-[(1S,2E)-1-isopropyl-3-sulfoprop-2-enyl]-$N^1$,3-dimethyl-L-valinamide A solution of N,β,β-trimethyl-L-phenylalanyl-$N^1$-[(1S,2E)-3-(ethoxysulfonyl)-1-isopropylprop-2-enyl]-$N^1$,3-dimethyl-L-valinamide (30 mg, 0.057 mmol) from Example 63 in acetone (1 mL) is treated with tetrabutylammonium iodide (21 mg, 0.057 mmol). The reaction mixture is refluxed for 9 h, and then stirred at room temperature overnight. The solvent is removed. The residue is purified by reversal phase HPLC (mobile phase A: 0.1% TFA/5% acetonitrile/$H_2O$, mobile phase B: 100% acetonitrile) to give 10 mg (28%) of the title compound as a white solid. HRMS (ESI) calcd for $C_{25}H_{41}N_3O_5S$ [M+H] 496.2840, found 498.2840.

EXAMPLE 65

N,β,β-trimethyl-L-phenylalanyl-$N^1$-[(1S,2E)-3-(ethoxysulfonyl)-1-isopropylbut-2-enyl]-$N^1$,3-dimethyl-L-valinamide To a solution of ethyl 1-(diethoxyphosphoryl)ethanesulfonate (210 mg, 0.77 mmol) in anhydrous THF (4 mL) cooled to −78° C. is added butyllithium (0.4 mL, 1.0 mmol). After stirring for 20 min at −78° C., a solution of N-{1-[(1-Formyl-2-methyl-propyl)-methyl-carbamoyl]-2,2-dimethyl-propyl}-3-methyl-2-methylamino-3-phenyl-butyramide (0.77 mmol, from Reference Example 12) in anhydrous THF (4 mL), is added. The reaction mixture is stirred at −78° C. for an additional 3 h, and then gradually warmed to room temperature overnight. The reaction is quenched with water, extracted with $CH_2Cl_2$. The combined organic layers are washed with brine, dried ($Na_2SO_4$), filtered and concentrated. The residue is separated by reversal phase HPLC (mobile phase A: 0.1% TFA/5% acetonitrile/H₂O, mobile phase B: 100% acetonitrile) to give 97 mg (19%) of white solids which contains the trifluoroacetic acid salt of the title compound along with a small amount of its diastereoisomers. HRMS (ESI) calcd for $C_{28}H_{47}N_3O_5S$ [M+H] 538.3309, found 538.3302.

EXAMPLE 66

N,β,β-trimethyl-L-phenylalanyl-N¹-[(1S,2E)-1-isopropyl-3-sulfobut-2-enyl] N¹,3-dimethyl-L-valinamide and

EXAMPLE 67

N,β,β-trimethyl-L-phenylalanyl-N¹-[(1S,2Z)-1-isopropyl-3-sulfobut-2-enyl]-N¹,3-dimethyl-L-valinamide A solution of N,β,β-trimethyl-L-phenylalanyl-N¹-[(1S,2E)-3-(ethoxysulfonyl)-1-isopropylbut-2-enyl]-N¹,3-dimethyl-L-valinamide (30 mg, 0.046 mmol, from Example 65) in acetone (2 mL) is treated with tetrabutylammonium iodide (20 mg, 0.055 mmol). The reaction mixture is refluxed for 7 h, and then stirred at room temperature overnight. The solvent is removed. The residue is purified by reversal phase HPLC (mobile phase A: 0.1% TFA/5% acetonitrile/H₂O, mobile phase B: 100% acetonitrile) to give 12 mg (28%) of N,β,β-trimethyl-L-phenylalanyl-N¹-[(1S,2E)-1-isopropyl-3-sulfobut-2-enyl] N¹,3-dimethyl-L-valinamide as a white solid and 2 mg of N,β,β-trimethyl-L-phenylalanyl-N¹-[(1S,2Z)-1-isopropyl-3-sulfobut-2-enyl]-N¹,3-dimethyl-L-valinamide HRMS (ESI) for N,β,β-trimethyl-L-phenylalanyl-N¹-[(1S,2E)-1-isopropyl-3-sulfobut-2-enyl]-N¹,3-dimethyl-L-valinamide, calcd for $C_{26}H_{43}N_3O_5S$ [M+H] 510.2996, found 510.2986.

HRMS (ESI) for N,β,β-trimethyl-L-phenylalanyl-N¹-[(1S,2Z)-1-isopropyl-3-sulfobut-2-enyl]-N¹,3-dimethyl-L-valinamide, calcd for $C_{26}H_{43}N_3O_5S$ [M+H] 510.2996, found 510.2991.

EXAMPLE 68

N,β,β-trimethyl-L-phenylalanyl-N¹-[(1S,2E)-3-(dimethoxyphosphoryl)-1-isopropylprop-2-enyl]-N¹,3-dimethyl-L-valinamide To a solution of tetramethyl methylenediphosphonate (97 mg, 0.42 mmol) in anhydrous THF (2 mL) cooled to −78° C. is added butyllithium (0.17 mL, 0.42 mmol). After stirring for 20 min at −78° C., a solution of N-{1-[(1-Formyl-2-methyl-propyl)-methyl-carbamoyl]-2,2-dimethyl-propyl}-3-methyl-2-methylamino-3-phenyl-butyramide (100 mg, 0.21 mmol, from Reference Example 12) in anhydrous THF (1 mL), is added. The reaction mixture is stirred at −78° C. for additional 30 min, and then gradually warmed to room temperature for 40 h. The reaction is quenched with water, extracted with CH₂Cl₂. The combined organic layers are washed with brine, dried (Na₂SO₄), filtered and concentrated. The residue is purified by reversal phase HPLC (mobile phase A: 0.1% TFA/5% acetonitrile/H₂O, mobile phase B: 100% acetonitrile) to give 30 mg (22%) of the trifluoroacetic acid salt of the title compound as a white solid. HRMS (ESI) calcd for $C_{27}H_{46}N_3O_5P$ [M+H] 524.3248, found 524.3244.

EXAMPLE 69

N,β,β-trimethyl-L-phenylalanyl-N¹-{(1S,2E)-3-[hydroxy(methoxy)phosphoryl]-1-isopropylprop-2-enyl}-N¹,3-dimethyl-L-valinamide A solution of N,β,β-trimethyl-L-phenylalanyl-N¹-[(1S,2E)-3-(dimethoxyphosphoryl)-1-isopropylprop-2-enyl]-N¹,3-dimethyl-L-valinamide (7 mg, 0.013 mmol, from Example 68) in CH₂Cl₂ (0.3 mL) is treated with TMSBr (3.5 mg, 0.023 mmol). The reaction mixture is stirred at room temperature for 2 h, then concentrated. The residue is purified by reverse phase HPLC (mobile phase A: 0.1% TFA/5% acetonitrile/H₂O, mobile phase B: 100% acetonitrile) to give 2 mg (24%) of the trifluoroacetic acid salt of the title compound as a white solid. HRMS (ESI) calcd for $C_{26}H_{44}N_3O_5P$ [M−H] 508.2946, found 508.2939.

EXAMPLE 70

N,β,β-trimethyl-L-phenylalanyl-N¹-[(1S,2E)-1-isopropyl-3-phosphonoprop-2-enyl]N¹,3-dimethyl-L-valinamide A solution of N,β,β-trimethyl-L-phenylalanyl-N¹-[(1S,2E)-3-(dimethoxyphosphoryl)-1-isopropylprop-2-enyl]-N¹,3-dimethyl-L-valinamide (7 mg, 0.013 mmol, from Example 68) in CH₃CN (0.3 mL) is treated with TMSBr (6.1 mg, 0.04 mmol). The reaction mixture is stirred at room temperature for 4 h. Additional TMSBr (6.1 mg) is added. The reaction mixture is stirred for additional 4 h, then concentrated. The residue is purified by reverse phase HPLC (mobile phase A: 0.1% TFA/5% acetonitrile/H₂O, mobile phase B: 100% acetonitrile) to give 2 mg (25%) of the trifluoroacetic acid salt of the title compound as a white solid. HRMS (ESI) calcd for $C_{25}H_{42}N_3O_5P$ [M−H] 494.2789, found 494.2790.

EXAMPLE 71

N,β,β-trimethyl-L-phenylalanyl-N¹-[(1S,2E)-3-(diethoxyphosphoryl)-1-isopropyl-but-2-enyl]-N¹,3-dimethyl-L-valinamide To a solution of tetraethyl ethyl-1,1-bisphosphonate (65 mg, 0.215 mmol) in anhydrous THF (1 mL) cooled to −78° C. is added butyllithium (0.11 mL, 0.268 mmol). After stirring for 20 min at −78° C., a solution of N-{1-[(1-Formyl-2-methyl-propyl)-methyl-carbamoyl]-2,2-dimethyl-propyl}-3-methyl-2-methylamino-3-phenyl-butyramide (100 mg, 0.215 mmol, from Reference Example 12), in anhydrous THF (1 mL), is added. The reaction mixture is stirred at −78° C. for an additional 30 min, and then gradually warmed to room temperature for 60 h. The reaction is quenched with water, extracted with CH₂Cl₂. The combined organic layers are washed with brine, dried (Na₂SO₄), filtered and concentrated. The residue is purified by reversal phase HPLC (mobile phase A: 0.1% TFA/5% acetonitrile/H₂O, mobile phase B: 100% acetonitrile) to give 16 mg (11%) of a mixture of the major desired product along with small amount of its diastereoisomers as a white solid. HRMS (ESI) calcd for $C_{30}H_{52}N_3O_5P$ [M+H] 566.3717, found 566.3720.

EXAMPLE 72

N,β,β-trimethyl-L-phenylalanyl-N$^1$-[(1S,2E)-1-isopropyl-3-phosphonobut-2-enyl]-N$^1$,3-dimethyl-L-valinamide A solution of N,β,β-trimethyl-L-phenylalanyl-N$^1$-[(1S,2E)-3-(diethoxyphosphoryl)-1-isopropyl-but-2-enyl]-N$^1$,3-dimethyl-L-valinamide (11 mg, 0.02 mmol, from Example 71) in CH$_2$Cl$_2$ (0.5 mL) is treated with TMSBr (23 mg, 0.15 mmol). The reaction mixture is stirred at room temperature for 20 h, then concentrated. The residue is purified by reversal phase HPLC (mobile phase A: 0.02% TFA/H$_2$O, mobile phase B: 0.02% TFA/CH$_3$CN) to give 2.4 mg (19%) of desired product as a white solid. HRMS (ESI) calcd for C$_{26}$H$_{44}$N$_3$O$_5$P [M+H] 510.3091, found 510.3086.

EXAMPLE 73

N,β,β-trimethyl-L-phenylalanyl-N$^1$-[(1S,2E)-1-isopropyl-3-methyl-4-oxo-4-(1,3-thiazol-2-yl)but-2-enyl]-N$^1$,3-dimethyl-L-valinamide To a solution of thiazole (0.035 mL, 0.5 mmol) and TMEDA (0.068 mL, 0.45 mmol) in anhydrous THF (1.0 mL) cooled to −60° C. is added n-BuLi (0.17 mL, 0.43 mmol). After stirring for 20 min at −60° C., a solution of N,β,β-trimethyl-L-phenylalanyl-N$^1$-{(1S,2E)-1-isopropyl-4-[methoxy(methyl)-amino]-3-methyl-4-oxobut-2-enyl}-N$^1$,3-dimethyl-L-valinamide (52 mg, 0.1 mmol, from Example 52, in anhydrous THF (0.5 mL) is added. The purple reaction mixture is stirred for 2 h from −60° C. to room temperature, quenched with saturated aqueous ammonium chloride (1.5 mL). The reaction mixture is extracted with ethyl acetate three times. The combined organic layers are dried (Na$_2$SO$_4$), filtered and concentrated. The residue is purified by reversal phase HPLC (mobile phase A: 0.1% TFA/5% acetonitrile/H$_2$O, mobile phase B: 100% acetonitrile) to give 56 mg (86%) of desired product as a yellow solid.

HRMS (ESI) calcd for C$_{30}$H$_{44}$N$_4$O$_3$S [M+H] 541.3207, found 541.3203.

EXAMPLE 74

N,β,β-trimethyl-L-phenylalanyl-N-1-[(1S,2E)-4-hydroxy-1-isopropyl-3-methyl-4-phenylbut-2-enyl}-N-1,3-dimethyl-L-valinamide To a slurry of lithium aluminum hydride (12 mg, 0.32 mmole) in ether (5 mL) cooled to −30° C. is added a solution of N,β,β-trimethyl-L-phenylalanyl-N$^1$-{(1S,2E)-1-isopropyl-4-[methoxy(methyl)-amino]-3-methyl-4-oxobut-2-enyl}-N$^1$,3-dimethyl-L-valinamide (129 mg, 0.25 mmole, from Example 52) keeping the temperature below −25° C. The reaction mixture is allowed to warm to 0° C., stir for 15 mins then recooled to −30° C. and carefully quenched with ethyl acetate (2 mL) and water (2 mL). The mixture is allowed to warm to room temperature and partitioned between water and ether. The ether layer is dried over sodium sulfate, filtered and evaporated. The residue is dissolved in dry tetrahydrofuran (5 mL), cooled to 0° C. and a solution of 1 M phenylmagnesium bromide in tetrahydrofuran (0.75 mL, 0.75 mmole) added via syringe. The reaction mixture is stirred for 1 hour quenched with saturated ammonium chloride and partitioned between water and ether. The ether layer is washed with water, brine, dried over sodium sulfate, filtered and the solid chromatographed on silica gel with 4:1 hexane/ethyl acetate to give 22 mg of a white solid a mixture of epimeric alcohols, MS (ES): m/z 536.2 (M+H).

EXAMPLE 75

N,β,β-trimethyl-L-phenylalanyl-N-1-[(1S,2E,4R)-4-hydroxy-1-isopropyl-3-methyl-4-phenylbut-2-enyl}-N-1,3-dimethyl-L-valinamide and

EXAMPLE 76

N,β,β-trimethyl-L-phenylalanyl-N-1-[(1S,2E,4S)-4-hydroxy-1-isopropyl-3-methyl-4-phenylbut-2-enyl}-N-1,3-dimethyl-L-valinamide The reaction described in Example 74 is repeated on twice the scale and the mixture of alcohols are separated by hplc using acetonitrile/water with 0.02% formic acid from 5/95 to 100/0 over 1 hour. The first isomer isolated is arbitrarily assigned as the R alcohol, 45 mg of a white solid, as the formic acid salt which contains 7.2% of the S isomer, MS (ES): m/z 536.4 (M+H). The second isomer isolated is arbitrarily assigned as the R alcohol, 83 mg of a white solid, as the formic acid salt which contains 14.5% of the R isomer, MS (ES): m/z 536.4 (M+H).

EXAMPLE 77

N,β,β-trimethyl-L-phenylalanyl-N-1-[(1S,2E)-4-hydroxy-1-isopropyl-3-methyl-4-(1,3-thiazol-2-yl)but-2-enyl]-N-1,-3-dimethyl-L-valinamide To a slurry of lithium aluminum hydride (12 mg, 0.32 mmole) in ether (5 mL) cooled to −30° C. is added a solution of N,β,β-trimethyl-L-phenylalanyl-N$^1$-{(1S,2E)-1-isopropyl-4-[methoxy(methyl)-amino]-3-methyl-4-oxobut-2-enyl}-N$^1$,3-dimethyl-L-valinamide (129 mg, 0.25 mmole, Example 52) keeping the temperature below −25° C. The reaction mixture is allowed to warm to 0° C., stir for 15 mins then recooled to −30° C. and carefully quenched with ethyl acetate (2 mL) and water (2 mL). The mixture is allowed to warm to room temperature and partitioned between water and ether. The ether layer is dried over sodium sulfate, filtered and evaporated. The residue is dissolved in dry tetrahydrofuran (5 mL), cooled to 0° C. and a solution of 2-lithiothiazole (prepared from thiazole (85 mg, 1.0 mmole) in tetrahydrofuran (3 mL) at −78° C. and 2.5 M n-butyllithium (0.5 mL, 1.25 mmole)) is added via syringe. The reaction mixture is stirred for 1 hour quenched with saturated ammonium chloride and partitioned between water and ether. The ether layer is washed with water, brine, dried over sodium sulfate, filtered and the solid purified by HPLC to give 68 mg of a white solid a mixture of epimeric alcohols, MS (ES): m/z 543.4 (M+H).

EXAMPLE 78

N,β,β-trimethyl-L-phenylalanyl-N-1-[(1S,2E)-4-hydroxy-1-isopropyl-3-methylpent-2-enyl]-N-1,3-dimethyl-L-valinamide To a slurry of lithium aluminum hydride (12 mg, 0.32 mmole) in ether (5 mL) cooled to −30° C. is added a solution of N,β,β-trimethyl-L-phenylalanyl-N$^1$-{(1S,2E)-1-isopropyl-4-[methoxy(methyl)-amino]-3-methyl-4-oxobut-2-enyl}-N$^1$,3-dimethyl-L-valinamide (129 mg, 0.25 mmole, Example 52) keeping the temperature below −25°C. The reaction mixture is allowed to warm to 0° C., stir for 15 mins then recooled to −30° C. and carefully quenched with ethyl acetate (2 mL) and water (2 mL). The mixture is allowed to warm to room temperature and partitioned between water and ether. The ether layer is dried over sodium sulfate, filtered and evaporated. The residue is dissolved in dry tetrahydrofuran (5 mL), cooled to 0° C. and a solution of 3.0M methyl magnesium bromide (0.25 mL, 0.75 mmole) is added via syringe. The reaction mixture is stirred for 1 hour quenched with saturated ammonium chloride and partitioned between water and ether. The ether layer is washed with water, brine, dried over sodium sulfate, filtered and the solid purified by HPLC to give 70 mg of a white solid a mixture of epimeric alcohols, MS (ES): m/z 474.4 (M+H).

EXAMPLE 79

6-{[3,3-Dimethyl-2-(3-methyl-2-methylamino-3-phenyl-butyrylamino)-butyryl]-methyl-amino}-2,4,7-trimethyl-octa-2,4-dienoic acid To a slurry of lithium aluminum hydride (48 mg, 1.28 mmole) in ether (20 mL) cooled to −30° C. is added a solution of N,β,β-trimethyl-L-phenylalanyl-$N^1$-{(1S,2E)-1-isopropyl-4-[methoxy(methyl)-amino]-3-methyl-4-oxobut-2-enyl}-$N^1$,3-dimethyl-L-valinamide (516 mg, 1.0 mmole, Example 52) keeping the temperature below −25° C. The reaction mixture is allowed to warm to 0° C., stir for 15 min then recooled to −30° C. and carefully quenched with ethyl acetate (8 mL) and water (8 mL). The mixture is allowed to warm to room temperature and partitioned between water and ether. The ether layer is dried over sodium sulfate, filtered and evaporated. The residue is dissolved in dichloromethane (10 mL), (carboethoxyehylidene)triphenylphosphorane (1.09 g, 3.0 mmole) is added. The reaction mixture is stirred for 1 hour, then refluxed overnight. The reaction mixture is cooled to room temperature, evaporated to dyness and the residue purified by chromatography on silica gel eluting with 4:1 hexane/ethyl acetate to give 220 mg of a white solid. This solid 0.41 mmol) is treated with aqueous 1M lithium hydroxide solution (2.0 mL, 2.0 mmol), water (1.0 mL) and methanol (4.0 mL), to provide 6-{[3,3-Dimethyl-2-(3-methyl-2-methylamino-3-phenyl-butyrylamino)-butyryl]-methyl-amino}-2,4,7-trimethyl-octa-2,4-dienoic acid (112 mg) as the corresponding trifluoroacetic acid salt as a white solid after preparative HPLC, MS (ES): m/z 514.4 (M+H).

EXAMPLE 80

N,β,β-trimethyl-L-phenylalanyl-N-1-[(1S,2E)-1-isopropyl-3-methyl-4-oxo-4-phenylbut-2-enyl]-N-1,3-dimethyl-L-valinamide To a solution of N,β,β-trimethyl-L-phenylalanyl-$N^1$-{(1S,2E)-1-isopropyl-4-[methoxy(methyl)-amino]-3-methyl-4-oxobut-2-enyl}-$N^1$,3-dimethyl-L-valinamide (129 mg, 0.25 mmole, Example 52) in tetrahydrofuran (5 mL) at 0° C. is added 1M phenylmagnesium bromide in tetrahydrofuran (0.75 mL, 0.75 mmole) via syringe. The reaction mixture is stirred for 1 hour quenched with saturated ammonium chloride and partitioned between water and ether. The ether layer is washed with water, brine, dried over sodium sulfate, filtered and the residue purified by HPLC to give 36 mg of a white solid, MS (ES): m/z 534.4 (M+H).

EXAMPLE 81

(2S)-N-[(1S,2E)-4-hydroxy-1-isopropyl-3-methyl-2-butenyl]-N,3,3-trimethyl-2-{{[(2S)-3-methyl-2-(methylamino)-3-phenylbutanoyl]amino}butanamide To N,β,β-trimethyl-L-phenylalanyl-$N^1$-[(1S,2E)-3-carboxy-1-isopropylbut-2-enyl]-$N^1$,3-dimethyl-L-valinamide (200 mg) in acetonitrile (20 mL) at 25° C. is added 1-hydroxybenzotriazole hydrate (68 mg) and 1-(3-dimethylaminopropyl)-3-ethylcarbodiimide hydrochloride (108 mg). After 2 hours sodium borohydride (92 mg) is added. After 18 hours, to the heterogeneous reaction mixture is added water followed by 2N aqueous hydrochloric acid. Concentration in vacuo and purification by reverse phase HPLC (0.01% aqueous trifluoroacetic acid/acetonitrile gradient system) gave the trifluoracetic acid salt of the title compound as a white powder (148 mg). MS (ES): m/z 460.4 (M+H).

EXAMPLE 82

N,β,β-trimethyl-L-phenylalanyl-$N^1$-[(1S,2E)-1-isopropyl-3-methyl-4-oxo-2-butenyl]-$N^1$,3-dimethyl-L-valinamide

EXAMPLE 83

4-(dimethylsulfonio)-N,β,β-trimethyl-L-phenylalanyl-$N^1$-[(1S,2E)-1-isopropyl-3-methyl-4-oxo-2-butenyl]-$N^1$,3-dimethyl-L-valinamide trifluoroacetic acid Following the procedure described in *J. Org. Chem.* 1994, 59(7), 1771, to a solution of oxalyl chloride (0.17 mmol) in dichloromethane at −78° C. is added a solution of dimethylsulfoxide (0.348 mmol, 0.025 mL) in dichloromethane dropwise. After 10 min a solution of (2S)-N-[(1S,2E)-4-hydroxy-1-isopropyl-3-methyl-2-butenyl]-N,3,3-trimethyl-2-{[(2S)-3-methyl-2-(methylamino)-3-phenylbutanoyl]amino}butanamide trifluoroacetic acid (83 mg, from Example 81) in dichloromethane is added dropwise. After 20 min triethylamine (0.725 mmol, 0.1 mL) is added dropwise. The reaction mixture is allowed to warm to 25° C. then washed with water and dried over anhydrous sodium sulfate. Concentration in vacuo and purification by reverse phase HPLC (0.01% aqueous trifluoroacetic acid/acetonitrile gradient system) gave the trifluoroacetic acid salt of N,β,β-trimethyl-L-phenylalanyl-$N^1$-[(1S,2E)-1-isopropyl-3-methyl-4-oxo-2-butenyl]-$N^1$,3-dimethyl-L-valinamide as a white powder (43 mg) MS (ES): m/z 458.1 (M+H) and 4-(dimethylsulfonio)-N,β,β-trimethyl-L-phenylalanyl-$N^1$-[(1S,2E)-1-isopropyl-3-methyl-4-oxo-2-butenyl]-$N^1$,3-dimethyl-L-valinamide trifluoroacetate as a clear glass (28 mg) MS (ES): m/z 518.0 ($M^+$).

EXAMPLE 84

N,β,β-trimethyl-L-phenylalanyl-$N^1$-[(1S,2E)-1-isopropyl-3-methyl-4-oxo-2-pentenyl]-$N^1$-3-dimethyl-L-valinamide According to the procedures in J. Am. Chem. Soc., 1980, 3270 and *Tetrahedron Letters,* 1984, 5733 a solution of ethyl (E,4S)-4-[((2S)-3,3-dimethyl-2-{[(2S)-3-methyl-2-(methylamino)-3-phenylbutanoyl]amino}butanoyl)(methyl) amino]-2,5-dimethyl-2-hexenoate (250 mg) in tetrahydrofuran (5 mL) at −40° C. under nitrogen atmosphere is treated with Tebbe reagent (0.5 M in toluene, 0.55 mL, 1.1 mmol)

dropwise over 1 min. After 15 min the reaction mixture is allowed to warm to 25° C. After 2 h 15% aqueous sodium hydroxide (0.15 mL) is added to the red solution at −10° C. The reaction mixture is allowed to warm to 25° C. After 10 min gas evolution ceased and the green mixture is diluted with ether, dried over anhydrous sodium sulfate and filtered through diatomaceous earch. Concentration in vacuo gave a yellow oil (385 mg) (MS m+h=500). A portion of this material (285 mg) is dissolved in tetrahydrofuran (8 mL) and treated with 1N aqueous hydrochloric acid (0.4 mL). After 18 h the mixture is filtered through diatomaceous earth and purified by reverse phase HPLC (0.01% aqueous trifluoroacetic acid/acetonitrile gradient system) to give the trifuoroacetic acid salt of the title compound as a pale yellow powder. MS (ES): m/z 472.6 (M+H)

EXAMPLE 85

N,β,β-trimethyl-L-phenylalanyl-$N^1$-{(1S)-1-[(Z)-(2,5-dioxo-4-imidazolidinylidene)methyl]-2-methylpropyl}-$N^1$,3-dimethyl-L-valinamide To a solution of diethyl 2,4-dioxoimidazolidine-5-phosphonate (N. A. Meanwell et. al. *J. Org. Chem.* 1991, 56(24), 6897) (192 mg, 0.81 mmol) in ethanol (2 mL) is added a solution of lithium hydroxide hydrate (31 mg, 0.73 mmol) in water (0.2 mL). The resulting solution is transferred, using a minimum of ethanol, to a solution of N-{1-[(1-Formyl-2-methyl-propyl)-methyl-carbamoyl]-2,2-dimethyl-propyl}-3-methyl-2-methylamino-3-phenyl-butyramide (114 mg, 0.27 mmol, Reference Example 12) in ethanol (0.5 mL). After 3 days the reaction mixture is concentrated in vacuo and purified by reverse phase HPLC (0.01% aqueous trifluoroacetic acid/acetonitrile gradient system) to give the trifluoroactic acid salt of the title compound (3:1 mixture with its double bond isomer) as a white powder (17 mg).

HRMS (ESI) calcd for $C_{27}H_{41}N_5O_4$ 499.31602, found 500.32152 [M+H]

REFERENCE EXAMPLE 13 tert-butyl (1S,2E)-3-cyano-1-isopropyl-2-propenyl(methyl)carbamate

To a solution of tert-butyl (1S)-1-formyl-2-methylpropyl (methyl)carbamate (WO 99/32509) (500 mg, 202 mmol) in diclomethane (5 mL) is added (triphenylphosphoranylidene)acetonitrile (700 mg, 2.32 mmol). After 1 h additional (triphenylphosphoranylidene)acetonitrile is added (350 mg, 1.16 mmol). After 24 h the reaction mixture is concentrated in vacuo and chromatographed (silica gel, hexane/ether) to give the title compound as an oil (410 mg). Analysis for C13H22N2O2: Calc'd: C, 65.52; H, 9.3; N 11.75. Found: C, 65.3; H, 9.05; N,11.51. MS (ES): m/z 239.1 (M+H)

REFERENCE EXAMPLE 14

(E,4S)-5-methyl-4-(methylamino)-2-hexenenitrile

To a solution of tert-butyl (1S,2E)-3-cyano-1-isopropyl-2-propenyl(methyl)carbamate (400 mg, 1.68 mmol, from Reference Example 13) in dichloromethane (5 mL) is added trifluoroacetic acid (2 mL). After 2 h the reaction mixture is concentrated in vacuo. Dissolution in dichloromethane followed by concentration in vacuo (3×) gave the trifluoroacetic acid salt of the title compound as an oil. MS (ES): m/z 139.1 (M+H)

REFERENCE EXAMPLE 15 tert-butyl (1S)-1-{[[(1S,2E)-3-cyano-1-isopropyl-2-propenyl](methyl)amino]carbonyl}-2,2-dimethylpropylcarbamate To a solution of (E,4S)-5-methyl-4-(methylamino)-2-hexenenitrile trifluoroacetic acid (−1.68 mmol, from Reference Example 14), 2-tert-Butoxycarbonylamino-3,3-dimethyl-butyric acid (389 mg, 1.68 mmol), (benzotriazol-1-yloxy)tripyrrolidinophosphonium hexafluorophosphate (PyBOP, 916 mg, 1.76 mmol) in dichloromethane (5 mL) at OC is added Hunig's base (0.877 mL, 5.04 mmol). After 5 min the cooling bath is removed. After 24 h 5% aqueous citric acid is added. The aqueous phase is washed with dichloromethane three times. The combined organic extracts are dried over anhydrous magnesium sulfate and concentrated in vacuo to give an oil. Chromatography (silica gel, hexane/ether) gave the title compound as a yellow foam (200 mg). MS (ES): m/z 352.0 (M+H)

REFERENCE EXAMPLE 16

(2S)-2-amino-N-[(1S,2E)-3-cyano-1-isopropyl-2-propenyl]-N,3,3-trimethylbutanamide To a solution of tert-butyl (1S)-1-{[[(1S,2E)-3-cyano-1-isopropyl-2-propenyl](methyl)amino]carbonyl}-2,2-dimethylpropylcarbamate (180 mg, from Reference Example 15) in dichloromethane (5 mL) is added trifluoroacetic acid (2 mL). After 20 min the reaction mixture is concentrated in vacuo. Dissolution in dichloromethane followed by concentration in vacuo (3×) gave the trifluoroacetic acid salt of the title compound as a yellow foam (210 mg). MS (ES): m/z 252.2 (M+H)

REFERENCE EXAMPLE 17 tert-butyl (1S)-1-{[((1S)-1-{[[(1S,2E)-3-cyano-1-isopropyl-2-propenyl](methyl)amino]carbonyl}-2,2-dimethylpropyl)amino]carbonyl}-2-methyl-2-phenylpropyl(methyl)carbamate To (2S)-2-amino-N-[(1S,2E)-3-cyano-1-isopropyl-2-propenyl]-N,3,3-trimethylbutanamide trifluoroacetic acid (179 mg, from Reference Example 16), O-(7-azabenzotriazol-1-yl)-N,N, N′,N′-tetramethyluronium hexafluorophosphate (HATU, 297 mg) and 1-Hydroxy-7-azabenzotriazole (HOAt, 6.8 mg) is added diisopropylethylamine (252 uL) followed by dichloromethane (9 mL) and (2S)-2-[(tert-butoxycarbonyl) (methyl)amino]-3-methyl-3-phenylbutanoic acid (162 mg). After 18 h 5% aqueous citric acid is added. The aqueous phase is washed with dichloromethane three times. The combined organic extracts are dried over anhydrous magnesium sulfate and concentrated in vacuo to give a yellow oil. Chromatography (silica gel, hexane/ether) gave the title compound as a yellow foam (176 mg). MS (ES): m/z 541.1 (M+H)

EXAMPLE 86

(2S)-N-[(1S,2E)-1-isopropyl-3-(1H-tetraazol-5-yl)-2-propenyl]-N,3,3-trimethyl-2-{[(2S)-3-methyl-2-(methylamino)-3-phenylbutanoyl]amino}butanamide Following the procedure outlined in *J. Org. Chem.*, 1993, 58, 4139, tert-butyl (1S)-1-{[((1S)-1-{[[(1S,2E)-3-cyano-1-isopropyl-2-propenyl](methyl)amino]carbonyl}-2,2-dimethylpropyl)amino]carbonyl}-2-methyl-2-phenylpropyl (methyl)carbamate (40 mg, from Reference Example 17), azidotrimethylsilane (20 uL, 17 mg) and dibutyltin oxide (2 mg) in toluene (1.6 mL) is heated at 100° C. for 18 h. Additional azidotrimethylsilane (10 uL) and dibutyltin oxide (0.5 mg) is added and the reaction mixture heated further. The reaction mixture is concentrated in vacuo. Dissolution in methanol followed by concentration in vacuo (3×) gave an oil. Chromatography (silica gel, dichloromethane/methanol) gave an oil (20 mg). A solution of this material in dichloromethane (2 mL) is treated with trifluoroacetic acid (1 mL). After 1 h the reaction mixture is concentrated in vacuo. Dissolution in dichloromethane followed by concentration in vacuo (3×) gave the trifluoroacetic acid salt of the title compound as a pink solid (14 mg). MS (ES): m/z 484.0 (M+H)

REFERENCE EXAMPLE 18 tert-butyl methyl[(1S)-2-methyl-1-(4-morpholinyl-carbonyl)-2-phenylpropyl]carbamate To a cooled (0°C., ice bath) solution of (2S)-2-[(tert-butoxycarbonyl)(methyl)amino]-3-methyl-3-phenylbutanoic acid (1.0 g, 3.30 mmol, WO 99/32509) and benzotriazole-1-yl-oxy-tris-pyrrolidinophosphonium hexafluorophosphate (1.46 g, 3.30 mmol) in anhydrous dichloromethane (5 ml) is added diisopropylethylamine (1.15 ml, 6.60 mmol) under an inert atmosphere. To this solution is added a solution of morpholine (0.313 ml, 3.60 mmol) in dichloromethane (2.5 ml). After stirring at 0° C. for 5-10 minutes, the cooling bath is removed, and the resulting reaction mixture is stirred at room temperature for 15-20 hours. The mixture is diluted with water, and the aqueous layer is extracted with ethyl acetate (3 times). The combined extracts are washed with saturated sodium chloride solution, dried over sodium sulfate, filtered and concentrated in vacuo. The residue is chromatographed (silica gel, flash column), to give a dark yellow oil. (0.943 g, 76%) MS [M+H] 377.2

REFERENCE EXAMPLE 19 tert-butyl (1S)-1-formyl-2-methyl-2-phenylpropyl (methyl)carbamate

To a cooled solution (0° C., ice bath) of tert-butyl methyl [(1S)-2-methyl-1-(4-morpholinylcarbonyl)-2-phenylpropyl] carbamate (0.870 g, 2.32 mmol, from Reference Example 18) in anhydrous tetrahydrofuran (3.0 ml), 1.0M lithium aluminum hydride (5.8 ml, 5.8 mmol) in tetrahydrofuran is added dropwise over 30 minutes. The reaction mixture stirred at room temperature for 30 minutes and is quenched with 5% potassium hydrogen sulfate and stirred at room temperature for 15 minutes. The mixture is washed with ether (3 times). The organic layer is then collected and dried with sodium sulfate and concentrated in vacuo to give a colorless oil. The crude product is used without further purification. (0.940 g, 80%) MS [M+H] 292.2

REFERENCE EXAMPLE 20 ethyl(2E,4S)-4-[(N-{(2S)-2-[(tert-butoxycarbonyl) (methyl)amino]-3-methyl-3-phenylbutyl}-3-methyl-L-valyl)(methyl)amino]-2,5-dimethyl-2-hexenoate To a stirred slurry of tert-butyl (1S)-1-formyl-2-methyl-2-phenylpropyl(methyl) carbamate (104 mg, 0.40 mmole, Reference Example 19) with ethyl 4-[(2-Amino-3,3-dimethyl-butyryl)-methyl-amino]-2,5-dimethyl-hex-2-enoic acid ethyl ester (122 mg, 0.40 mmole) in MeOH (2.5 ml), a solution of zinc chloride (32.7 mg, 0.6 eq) and sodium cyanoborohydride (34.4 mg, 0.48 mmol) in MeOH (2.5 ml) is added over 5 minutes at room temperature. The resulting mixture is stirred for 15-24 hours at room temperature under an inert atmosphere. After concentration, the residue is taken up in ethylacetate, washed with sodium bicarbonate. The aqueous phase is extracted with ethylacetate. The combined organic layers is washed with brine, dried and is chromatographed (silica gel, flash column) to give a white solid. (0.164 mg, 81%) M.W. 587.8 [M+H] 588.3

REFERENCE EXAMPLE 21

(2E,4S)-4-[(N-{(2S)-2-[(tert-butoxycarbonyl)(methyl)amino]-3-methyl-3-phenylbutyl}-3-methyl-L-valyl)(methyl)amino]-2,5-dimethyl-2-hexenoic acid Ethyl (2E,4S)-4-[(N-{(2S)-2-[(tert-butoxycarbonyl)(methyl)amino]-3-methyl-3-phenyl butyl}-3-methyl-L-valyl) (methyl)amino]-2,5-dimethyl-2-hexenoate (50 mg, 0.085 mmol, Reference Example 20) is dissolved in methanol (1 ml), tetrahydrofuran (1 ml). To this solution is added water (0.5 ml) and solid lithium hydroxide (4.1 mg). The resulting mixture is stirred at room temperature for 15 hours. The organic solvents are removed in vacuo, and the residual aqueous mixture is cooled with an ice water bath, and acidified to pH 5.5-6.0 with aqueous 1 N aqueous citric acid solution. The precipitate is collect by filtration, and the solid is washed with a cold water, and dried over high vacuum. Alternatively, the product can be purified by using preparative HPLC. (40 mg, 80%) MS [M+H] 588.2

EXAMPLE 87

(2E,4S)-2,5-dimethyl-4-(methyl{3-methyl-N-[(2S)-3-methyl-2-(methylamino)-3-phenylbutyl]-L-valyl}amino)-2-hexenoic acid (2E,4S)-4-[(N-{(2S)-2-[(tert-butoxycarbonyl)(methyl) amino]-3-methyl-3-phenylbutyl}-3-methyl-L-valyl)(methyl)amino]-2,5-dimethyl-2-hexenoic acid (40 mg, 0.068 mmol, from reference example 21) is dissolved in dichloromethane (3 ml) and treated with 4N hydrogen chloride (0.068 ml, 0.27 mmol) at room temperature for 30 minutes. The reaction mixture is then concentrated in vacuo and triturated with ether to give a white solid (29 mg, 87%). The crude material is purified by reverse phase HPLC. MS [M+H] 488.62

EXAMPLE 88

(2S)-N-[(1S,2E)-4-(1H-imidazol-2-yl)-1-isopropyl-3-methyl-4-oxobut-2-enyl]- -trimethyl-2-{[(2S)-3-methyl-2-(methylamino)-3-phenylbutanoyl] amino}butanamide To a solution of ethyl (E,4S)-4-[tert-butoxycarbonyl)(methyl)amino]-2,5-dimethyl-2-hexenoate (2.8 g, 9.35 mmole) in 43 ml anhydrous tetrahydrofuran is added 1 M aqueous lithium hydroxide (46.7 ml, 46.76 mmole), methanol (90.5 mL) and water (23.8 ml). The reaction mixture is stirred at room temperature overnight. The solvent is removed in vacuo. The residue is partition between ethyl acetate and water. The aqueous layer is acidified with 1 N hydrochloric acid dropwise in ice bath until pH 4.5. Organic layer is separated. The aqueous layer is extracted twice with ethyl acetate. The combined organic extracts are washed with brine, dried over sodium sulfate, filtered, concentrated in vacuo to give 2.42 g (95%) of (2E,4S)-4-[(tert-butoxycarbonyl)(methyl) amino]-2,5-dimethylhex-2-enoic acid as a white solid. MS(ES$^-$): (M−H)=270.2

A solution of this carboxylic acid (1.56 g, 5.75 mmole) in 11.61 ml tetrahydrofuran is treated with N,O-dimethylhydroxylamine hydrochloride (954 mg, 9.8 mmol) which is dissolved in 11.61 ml water. The pH is adjusted to 4.5 with 1 N sodium hydroxide solution. 1-[3-(dimethylamino)propyl]-3-ethylcarbodiimidehydrochloride (2.76 g, 14.4 mmol) in water (39.4 ml) is added dropwise over a period of 25 minutes to the solution of carboxylic acid and N,O-dimethylhydroxylamine, while the pH is maintained to a constant value of 4.5. After 2.5 hours, the solution is saturated with sodium chloride and extracted with ethyl acetate. The organic extract is dried over sodium sulfate, filtered, concentrated in vacuo to give (1S,2E)-1-isopropyl-4-[methoxy(methyl)amino]-3-methyl-4-oxobut-2-enyl(methyl)carbamate 903.9 mg (50%) as a light yellow oil. MS(ES$^+$): (M+Na)=337.1

To a solution of imidazole (10.0 g, 146.9 mmole) in 100 ml dimethyl sulfoxide at room temperature under nitrogen is added sodium hydride (6.46 g, 161.6 mmole). The solution is stirred at 80° C. for 2 hours. Chloromethyl ethyl ether (16.35 ml, 176.3 mmole) is added dropwise. The reaction mixture is stirred for another 2 hour at 80° C., cooled to room temperature, poured into 5% aqueous solution and extracted with dichloromethane (4×200 ml). The combined organic extracts are dried over sodium sulfate, filtered, concentrated in vacuo. The residue is fresh chromatographed in hexane/ethyl acetate from 5:1 to 2:1 to give 1-ethoxymethyl-1H-imidazole as a brown oil 1.68 g (90%) MS(ES$^+$): (M+H)=127.0 To the solution of 1-ethoxymethyl-1H-imidazole (1.24 g, 0.98 mmole) in 3.92 ml anhydrous tetrahydrofuran at −78° C. is added n-butyllithium (1.6 M in hexane) over 5 minutes. Reaction mixture is stirred at −78° C. for 1.5 hour, then (1S,2E)-1-isopropyl-4-[methoxy(methyl)amino]-3-methyl-4-oxobut-2-enyl(methyl)carbamate (427 mg, 1.36 mmole) in 2 ml anhydrous tetrahydrofuran is added over 10 minutes. The reaction mixture is stirred at −78° C. for 1 hour. Then, it is warmed to room temperature, stirred for 1 hour at room temperature. The reaction mixture is diluted with dichloromethane/water. The organic layer is washed with 5% sodium bicarbonate, dried over sodium sulfate, filtered, concentrated in vacuo. The residue is fresh chromatographed in hexane/ethyl acetate from 3:1 to 1:1 to give light yellow oil: [4-(1-Ethoxymethyl-1H-imidazol-2-yl)-1-isopropyl-3-methyl-4-oxo-but-2-enyl]-methyl-carbamic acid tert-butyl ester (120 mg, 23%) MS(ES$^+$): (M+H)=380.2

[4-(1-Ethoxymethyl-1H-imidazol-2-yl)-1-isopropyl-3-methyl-4-oxo-but-2-enyl]-methyl-carbamic acid tert-butyl ester (496 mg, 1.31 mmole) is stirred in 4N hydrochloric acid/dioxane at room temperature under nitrogen for 2 hours. The solvent is removed in vacuo. Dichloromethane is added to the residue and evaporated (this step is repeated twice) to give a white solid amino intermediate which then stirred with 2-tert-Butoxycarbonylamino-3,3-dimethyl-butyric acid (410.5 mg, 1.78 mmole), 3-(diethoxyphosphoryloxy)-1,2,3-benzotriazin-4(3H)-one (DEPBT, 531 mg, 1.77 mmole) and triethylamine (0.49 ml, 3.55 mmole) in 4 ml dichloromethane at room temperature overnight. The reaction mixture is diluted with dichloromethane/water. Organic layer is separated. The aqueous layer is extracted twice with dichloromethane. The combined organic extracted are washed with citric acid (4 ml), sodium carbonate (6 ml) and brine, dried over sodium sulfate, filtered, concentrated in vacuo. The residue is flash chromatographed with hexane/ethyl acetate from 5:1 to 1:1 to give a white crystals, (1-{[4-(-Ethoxymethyl-1H-imidazol-2-yl)-1-isopropyl-3-methyl-4-oxo-but-2-enyl]-methyl-carbonyl}-2,2-dimethyl-propyl)-carbamic acid tert-butyl ester: 171 mg (26%). MS(ES$^+$): (M+H)=493.2

Following above procedure, (1-{[4-(-Ethoxymethyl-1H-imidazol-2-yl)-1-isopropyl-3-methyl-4-oxo-but-2-enyl]-methyl-carbonyl}-2,2-dimethyl-propyl)-carbamic acid tert-butyl ester (171 mg, 0.34 mmole) is coupled with (2S)-2-(tert-Butoxycarbonyl-methyl-amino)-3-phenyl-3-methyl-butyric acid (128 mg, 0.42 mmole) in the presence of 3-(diethoxyphosphoryloxy)-1,2,3-benzotriazin-4(3H)-one (DEPBT, 104 mg, 0.35 mmole) and triethylamine (1.4 ml, 0.69 mmole) and 2.5 ml dichloromethane. The product isolated by reverse phase HPLC (0.01% trifluoroacetic acid in water/acetonitrile) to give a yellow oil, [1-(1-{[4-(-Ethoxymethyl-1H-imidazol-2-yl)-1-isopropyl-3-methyl-4-oxo-but-2-enyl]-methyl-carbamoyl}-2,2-dimethyl-propylcarbamoyl)-2-methyl-2-phenyl-propyl]-methyl-carbamic acid tert-butyl ester: 46 mg (20%) MS(ES$^+$): (M+H)=682.4

[1-(1-{[4-(-Ethoxymethyl-1H-imidazol-2-yl)-1-isopropyl-3-methyl-4-oxo-but-2-enyl]-methyl-carbamoyl}-2,2-dimethyl-propylcarbamoyl)-2-methyl-2-phenyl-propyl]-methyl-carbamic acid tert-butyl ester (45 mg, 0.066 mmole) is treated with 2 ml trifluoroacetic acid in 2 ml dichloromethane at room temperature for 2 hours. The solvent is evaporated and pumped in oven overnight to give 8 mg white solid product, (2S)-N-[(1S,2E)-4-(1H-imidazol-2-yl)-1-isopropyl-3-methyl-4-oxobut-2-enyl]-N,3,3-trimethyl-2-{[(2S)-3-methyl-2-(methylamino)-3-phenylbutanoyl]amino}butanamide: 8 mg (16%). MS(ES$^+$): (M+H)=524.4

EXAMPLE 89

N,β,β-trimethyl-L-phenylalanyl-N$^1$,3-dimethyl-N$^1$-{(1S)-2-methyl-1-[(Z)-(3-methyl-2,5 -dioxoimidazolidin-4-ylidene)methyl]propyl}-L-valinamide A mixture of 1-methylhydantoin (20.25 g, 180 mmole) and acetic acid (100 ml) is heated to 90° C. Bromine (10 ml, 195 mmole) is introduced dropwise at such a rate that instant decolorization occurred. After the addition is completed, the reaction mixture is stirred at 90° C. for 60 minute and at room temperature overnight. The acetic acid is decanted from white precipitate and removed in vacuo. The residue is combined with the precipitate and suspended in diethylether (200 ml). Triethylphosphite (32 ml, 180 mmole) is added portionwise with stirring and cooling. A solution resulted which on continued stirring, yield trace of white precipitate. The mixture is diluted with diethyl ether and allowed to stand overnight. Decanted the solvent, and pumped in vacuum oven to give white crystal ylide, (3-Methyl-2,5-dioxo-imidazolidin-4-yl)-phosphonic acid diethyl ester: 16.57 g (36.8%) MS(ES$^+$): (M+H)=251.0

The yield, (3-methyl-2,5-dioxo-imidazolidin-4-yl)-phosphonic acid diethyl ester (0.915 g, 3.0 mmol) in ethanol (9 mL) is added to lithium hydroxide monohydrate (139 mg, 2.1 mmol) in 0.9 ml water to give a yellow solution. It is then added to N-{1-[(1-formyl-2-methyl-propyl)-methyl-carbamoyl]-2,2-dimethyl-propyl}-3-methyl-2-methylamino-3-phenyl-butyramide (~1 mmol, from Reference Example 12) in 3 mL ethanol. The reaction mixture is stirred at room temperature for 60 hours. Solvent is evaporated. The residue is diluted with dichloromethane/water. The aqueous layer is extracted twice with dichloromethane. The combined organic extracts are washed with brine, dried oversodium sulfate, filtered and concentrated in vacuo. The residue is chromatographed by reverse phase HPLC (0.01% trifluoroacetic acid in water/acetonitrile) to give the product as a white solid, N,beta,beta-trimethyl-L-phenylalanyl-N$^1$,3-dimethyl-N$^1$-{(1S)-2-methyl-1-[(Z)-(3-methyl-2,5-dioxoimidazolidin-4-ylidene)methyl]propyl}-L-valinamide:25 mg (4%) MS(ES$^+$): (M+H)=514.3

EXAMPLE 90

N-{1-[(5-Hydroxy-1-isopropyl-3-methyl-4-oxo-pent-2-enyl)-methyl-carbamoyl]-2,2-dimethyl-propyl}-3-methyl-2-methylamino-3-phenyl-butyramide To a solution of trimethyl-(2-tributylstannanyl-methoxymethoxy-ethyl)-silane (933 mg, 2.07 mmole, E. Fernandez-Megia and S. V. Ley; Synlett 2000, 4, 455-8) in 6 mL tetrahydrofuran at −78° C. is added dropwise 1.6 M n-butyllithium solution in hexanes (1.25 mL, 2.0 mmole). The resulting yellow solution is stirred for 10 mins at −78° C. Then a solution of N,β,β-trimethyl-L-phenylalanyl-N$^1$ {(1S, 2E)-1-isopropyl-4-[methoxy(methyl)amino]-3-methyl-4-oxobut-2-enyl}-N$^1$,3-dimethyl-L-valinamide (258 mg, 0.5 mmole, Example 52) in tetrahydrofuan (5 mL) at −78° C. is added dropwise and the reaction mixture stirred at −78° C. for 15 mins and then at −60° C. for 45 mins. The reaction is quenched with a saturated aqueous solution of ammonium chloride (2 mL), warmed to room temperature and partioned between ethyl acetate (50 mL) and saturated aqueous solution of ammonium chloride (50 mL). The aqueous layer is extracted with ethyl acetate (30 mL) and the combined organic layer is washed with water, brine, dried over sodium sulfate, filtered and the residue treated with a mixture of trifluoroacetic acid (10 mL) and dichloromethane (5 mL) at 0° C. and stirred for 1 hour, evaporated and then purified by HPLC to give 52 mg of an off-white solid, MS (ES): m/z 488.4 (M+H).

REFERENCE EXAMPLE 22

3,3-dimethyl-3-phenyl propionic acid

Following a literature procedure, (Leffler, J. E.; Barbas, J. T. *JACS*. 1981, 103(26), 7768-7773), to a mixture of magnesium turnings (9.5 g) and neophyl chloride (7.5 mL) in tetrahydrofuran (100 mL) is added a spatula tip of iodine and 1,2-dibromoethane (1 mL). The mixture is heated gently with under a heat gun to initiate a vigorous reaction. A solution of neophyl chloride (57 mL) in tetrahydrofuran (360 mL) is added dropwise over the course of 90 minutes. Following completion of the addition, the reaction mixture is stirred for an additional five hours, then solid carbon dioxide (25 g) is added to the flask. After 10 minutes, the flask is transferred to a 40° C. water bath until all carbon dioxide had sublimed. The solvent is then removed under reduced pressure to afford the title compound (58 g, 81%) as a white paste. MS (ES$^+$): (M+H)=178.8

REFERENCE EXAMPLE 23

(4S)-4-isopropyl-3-(3-methyl-3-phenylbutanoyl)-1,3-oxazolidin-2-one

To a solution of 3,3-dimethyl-3-phenyl propionic acid (2.1 g, 12 mmol, from Reference Example 22) in anhydrous tetrahydrofuran (24 mL) is added under inert atmosphere triethylamine (2.0 mL) and the mixture is cooled to −78° C. in a dry-ice acetone bath. Pivaloyl chloride (1.5 mL, 13 mmol) is added dropwise, causing the immediate formation of a white precipitate. The reaction mixture is allowed to sit for 15 minutes at −78° C. and is then stirred at 0° C. in an ice-water bath. In a separate flask, a solution of (S)-4-isopropyl-2-oxazolidinone (1.5 g, 12 mmol) in anhydrous tetrahydrofuran (27 mL) is prepared under inert atmosphere and cooled to −35° C. in a dry-ice/acetone bath. A small amount of triphenylmethane (<5 mg) is added as an indicator of deprotonation. n-Butyllithium (1.6 M solution in hexanes, 7.7 mL, 12 mmol) is added dropwise via syringe. After 30 minutes of stirring at 0° C., the flask containing the mixed anhydride is re-cooled to −78° C. in a dry-ice/acetone bath. The solution of the lithium anion of the oxazolidinone is added to the mixed anhydride solution via cannula. The source flask is washed twice with tetrahydrofuran (4 mL×2) and these washings are also transferred via cannula to the mixed anhydride solution. The reaction mixture is stirred at −78° C. for 1 hour, 0° C. for 1 hour, and allowed to warm to room temperature overnight. The following morning, water (~15 mL) is added and stirring is continued for 20 minutes. The aqueous phase is extracted thrice with diethyl ether. The combined extracts are washed with saturated aqueous sodium chloride, dried over sodium sulfate, decanted, and concentrated under reduced pressure to afford (3.6 g,>100% crude) of a pale yellow oil. The crude material is purified by flash chromatography (ethyl acetate/hexanes) to afford 1.5 g (44%) of a clear, colorless oil. MS (ES$^+$): (M+H)=290.0

REFERENCE EXAMPLE 24

(4S)-3-[(2S)-2,3-dimethyl-3-phenylbutanoyl]-4-isopropyl-1,3-oxazolidin-2-one

A solution of (4S)-4-isopropyl-3-(3-methyl-3-phenylbutanoyl)-1,3-oxazolidin-2-one (0.23 g, 0.79 mmol, from Reference Example 23) in anhydrous tetrahydrofuran (3 mL) is cooled to −78° C. in a dry-ice/acetone bath while stirring under a nitrogen atmosphere. Sodium hexamethylsilazide (1.0 M solution in tetrahydrofuran, 0.95 mL, 0.95 mmol) is added dropwise to the solution via syringe. After stirring for 30 minutes at −78° C., iodomethane (0.25 mL, 4.0 mmol) in tetrahydrofuran (1 mL) is added dropwise. The reaction mixture is stirred overnight (18 hours) while warming to room temperature. The reaction mixture is diluted with water (10 mL) and ethyl acetate (10 mL). The aqueous phase is extracted thrice with ethyl acetate. The combined extracts are washed with saturated aqueous sodium hydrogen carbonate and saturated aqueous sodium chloride, dried over sodium sulfate, decanted, and concentrated under reduced pressure to afford a clear yellow oil, which slowly solidified to an amorphous solid under high vacuum. The crude material is purified by flash chromatography (ethyl acetate/hexanes) to afford a crystalline solid (0.17 g, 71%). MS (ES$^+$): (M+H)=303.9

REFERENCE EXAMPLE 25

(2S)-2,3-dimethyl-3-phenylbutanoic acid

To a 0° C. solution of (4S)-3-[(2S)-2,3-dimethyl-3-phenylbutanoyl]-4-isopropyl-1,3-oxazolidin-2-one (0.13 g, 0.43 mmol, from Reference Example 24) in tetrahydrofuran (6 mL) and water (2 mL) is added 30% aqueous hydrogen peroxide (2.4 mL). After one to two minutes of stirring, lithium hydroxide monohydrate (36 mg) is added and the reaction mixture is allowed to stir overnight while warming to room temperature. On the following day, the reaction mixture is cooled to 0° C. and aqueous sodium sulfite solution (1.5 M,

89

1.3 mL) is added. After stirring for an hour at room temperature, the reaction mixture is concentrated under reduced pressure. The aqueous residue is extracted twice with dichloromethane, then acidified to pH 1 with 10% aqueous hydrochloric acid solution. The acidified aqueous phase is then extracted thrice with ethyl acetate. The combined organic extracts are washed with saturated aqueous sodium chloride, dried over anhydrous sodium sulfate, decanted, and concentrated under reduced pressure to give a white crystalline solid (60 mg, 72%). Mp 69-72° C. MS (ES$^-$): (M−H)=191.0

EXAMPLE 91

Ethyl (E,4S)-4-[((2S)-2-{[(2S)-2,3-dimethyl-3-phenylbutanoyl]amino}-3,3-dimethylbutanoyl)(methyl)amino]-2,5-dimethyl-2-hexenoate To a cooled (0° C., ice bath) solution of (2S)-2,3-dimethyl-3-phenylbutanoic acid (0.11 g, 0.57 mmol, from Reference Example 25), hydroxybenzotriazole (93 mg, 0.69 mmol) and 1-(3-dimethylaminopropyl)-3-ethylcarbodiimine hydrochloride (0.15 g, 0.80 mmol) in anhydous dimethylformamide (2 ml) is added N-methylmorpholine (95 uL, 0.86 mmol) via syringe under an inert atmosphere. After stirring for 15 minutes at 0° C., the cooling bath is removed, and the resulting mixture is stirred for 1 hour. The solution is cooled at 0° C. (ice water bath), and to this mixture is added a solution of ethyl (2E,4S)-2,5-dimethyl-4-[methyl(3-methyl-L-valyl)amino]hex-2-enoate hydrochloride (0.56 mmol) in anhydrous dimethylformamide (2 ml). The cooling bath is removed, and the resulting mixture is stirred for 22 hours at room temperature under an inert atmosphere. The mixture is diluted with water, and the aqueous layer is extracted with ethyl acetate (3 times). The combined extracts are washed with saturated aqueous sodium chloride, dried over anhydrous sodium sulfate, filtered and concentrated in vacuo. The residue is chromatographed (silica gel, flash column), to provide a white foam (0.20 g, 71%). MS (ES$^+$): (M+H)=487.0

EXAMPLE 92

(E,4S)-4-[((2S)-2-{[(2S)-2,3-dimethyl-3-phenylbutanoyl]amino}-3,3-dimethylbutanoyl)(methyl)amino]-2,5-dimethyl-2-hexenoic acid Ethyl (E,4S)-4-[((2S)-2-{[(2S)-2,3-dimethyl-3-phenylbutanoyl]amino}-3,3-dimethylbutanoyl)(methyl)amino]-2,5-dimethyl-2-hexenoate (0.17 g, 0.35 mmol, from Example 91) is dissolved in methanol (1.2 mL) and tetrahydrofuran (1.2 mL) and cooled to 0° C. (ice water bath). To this solution is added water (0.6 mL) and aqueous lithium hydroxide monohydrate (30 mg, 0.70 mmol). The cooling bath is removed, and the resulting mixture is stirred at 50° C. for 15 hours. Solvents are removed in vacuo to provide a beige foam, which is then dissolved in water. The solution is acidfied to pH 1 with 10% aqueous hydrochloric acid solution and then extracted thrice with ethyl acetate. The combined extracts are washed with saturated sodium chloride solution, dried over anhydrous sodium sulfate, decanted, and concentrated under reduced pressure to afford a white solid (0.16 g, 100%). MS (ES$^+$): (M+H)=459.0

REFERENCE EXAMPLE 26

(4S)-4-benzyl-3-(3-methyl-3-phenylbutanoyl)-1,3-oxazolidin-2-one

To a solution of 3,3-dimethyl-3-phenyl propionic acid (10 g, 57 mmol, from Reference Example 22) in anhydrous tetrahydrofuran (120 mL) is added under inert atmosphere triethylamine (10 mL) and the mixture is cooled to −78° C. in a dry-ice acetone bath. Pivaloyl chloride (7.4 mL, 60 mmol) is added dropwise, causing the immediate formation of a white precipitate. The reaction mixture is allowed to sit for 15 minutes at −78° C. and is then stirred at 0° C. in an ice-water bath. In a separate flask, a solution of (S)-4-benzyl-2-oxazolidinone (9.9 g, 56 mmol) in anhydrous tetrahydrofuran (130 mL) is prepared under inert atmosphere and cooled to −35° C. in a dry-ice/acetone bath. A small amount of triphenylmethane (<5 mg) is added as an indicator of deprotonation. n-Butyllithium (1.6 M solution in hexanes, 40 mL, 64 mmol) is added dropwise via syringe. After 30 minutes of stirring at 0° C., the flask containing the mixed anhydride is re-cooled to −78° C. in a dry-ice/acetone bath. The solution of the lithium anion of the oxazolidinone is added to the mixed anhydride solution via cannula. The source flask is washed twice with tetrahydrofuran (4 mL×2) and these washings are also transferred via cannula to the mixed anhydride solution. The reaction mixture is stirred at −78° C. for 1 hour and at 0° C. for 1 hour. Water (100 mL) is added and stirring is continued for 15 minutes. The aqueous phase is extracted thrice with diethyl ether. The combined extracts are washed with saturated aqueous sodium bicarbonate and saturated aqueous sodium chloride, dried over sodium sulfate, decanted, and concentrated under reduced pressure to afford 20 g of a white paste. The crude material is purified by flash chromatography (ethyl acetate/hexanes) to afford 11 g (56%) of a flocculent white solid. MS (ES$^+$): (M+H)=338.1

REFERENCE EXAMPLE 27

(4S)-3-[(2S)-2-azido-3-methyl-3-phenylbutanoyl]-4-benzyl-1,3-oxazolidin-2-one

A solution of (4S)-4-benzyl-3-(3-methyl-3-phenylbutanoyl)-1,3-oxazolidin-2-one (1.0 g, 3.0 mmol, from Reference Example 26) in anhydrous tetrahydrofuran (16 mL) is cooled to −78° C. in a dry-ice/acetone bath while stirring under a nitrogen atmosphere. Potassium hexamethylsilazide (0.5 M solution in toluene, 6.6 mL, 3.3 mmol) is added dropwise to the solution via syringe. After stirring for 1 hour at −78° C., trisyl azide (1.2 g, 3.8 mmol) in tetrahydrofuran (8 mL) is added dropwise. The reaction mixture is stirred for 2-3 minutes at −78° C. and then quenched by the addition of glacial acetic acid (0.8 mL). Stirring is continued for 1 hour at 40° C. The reaction mixture is diluted with brine and diethyl ether. The aqueous phase is extracted thrice with diethyl ether. The combined extracts are washed with saturated aqueous sodium hydrogen carbonate and saturated aqueous sodium chloride, dried over sodium sulfate, decanted, and concentrated under reduced pressure to afford a white/yellow solid. The crude material is purified by flash chromatography (ethyl acetate/hexanes) to afford a clear, straw colored oil (1.1 g, 79%). TOF MS (ES$^+$): (M+H)=379.2

REFERENCE EXAMPLE 28

(2S)-2-azido-3-methyl-3-phenylbutanoic acid

2:1 Mixture of S to R

To a 0° C. solution (4S)-3-[(2S)-2-azido-3-methyl-3-phenylbutanoyl]-4-benzyl-1,3-oxazolidin-2-one (0.40 g, 1.1 mmol, from Reference Example 27) in tetrahydrofuran (16 mL) and water (5 mL) is added 30% aqueous hydrogen peroxide (0.26 mL). After one to two minutes of stirring, lithium hydroxide monohydrate (92 mg) is added and the reaction mixture is allowed to stir overnight while warming to room temperature.

On the following day, the reaction mixture is cooled to 0° C. and aqueous sodium sulfite solution (1.5 M, 5 mL) is added. After stirring for an hour at room temperature, the reaction mixture is concentrated under reduced pressure. The aqueous residue is extracted twice with dichloromethane, then acidified to pH 1 with 10% aqueous hydrochloric acid solution. The acidified aqueous phase is then extracted thrice with ethyl acetate. The combined organic extracts are washed with saturated aqueous sodium chloride, dried over anhydrous sodium sulfate, decanted, and concentrated under reduced pressure to give a clear light blond oil (0.25 mg,>100%). MS (ES$^-$): (M−H)=217.9

EXAMPLE 93

Ethyl (E,4S)-4-[((2S)-2-{[(2S)-2-azido-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-azido-3-methyl-3-phenylbutanoyl]amino}-3,3-dimethylbutanoyl)(methyl)amino]-2,5-dimethyl-2-hexenoate a 2:1 Mixture of S,S,S to R,S,S Diastereomers To a cooled (0° C., ice bath) solution of a 2:1 mixture of (2S)-2-azido-3-methyl-3-phenylbutanoic acid to (2R)-2-azido-3-methyl-3-phenylbutanoic acid (0.25 g, 1.1 mmol, from Reference Example 28), hydroxybenzotriazole (0.19 g, 1.4 mmol) and 1-(3-dimethylaminopropyl)-3-ethylcarbodiimine hydrochloride (0.31 g, 1.6 mmol) in anhydous dimethylformamide (4 ml) is added N-methylmorpholine (0.19 mL, 1.4 mmol) via syringe under an inert atmosphere. After stirring for 15 minutes at 0° C., the cooling bath is removed, and the resulting mixture is stirred for 1 hour. The solution is cooled at 0° C. (ice water bath), and to this mixture is added a solution of ethyl (2E,4S)-2,5-dimethyl-4-[methyl(3-methyl-L-valyl)amino]hex-2-enoate hydrochloride (1.1 mmol) in anhydrous dimethylformamide (4 ml). The cooling bath is removed, and the resulting mixture is stirred for 22 hours at room temperature under an inert atmosphere. The mixture is diluted with water, and the aqueous layer is extracted with ethyl acetate (3 times). The combined extracts are washed thrice with saturated aqueous sodium bicarbonate solution and twice with saturated aqueous sodium chloride, dried over anhydrous sodium sulfate, filtered and concentrated in vacuo. The residue is chromatographed (silica gel, flash column), to provide a clear, colorless semisolid (0.35 g, 61%). MS (ES$^+$): (M+H)=514.0

EXAMPLE 94

(E,4S)-4-[((2S)-2-{[(2S)-2-azido-3-methyl-3-phenylbutanoyl]amino}-3,3-dimethylbutanoyl)(methyl)amino]-2,5-dimethyl-2-hexenoic acid and (E,4S)-4-[((2S)-2-{[(2R)-2-azido-3-methyl-3-phenylbutanoyl]amino}-3,3-dimethylbutanoyl)(methyl)amino]-2,5-dimethyl-2-hexenoic acid A 2:1 mixture of ethyl (E,4S)-4-[((2S)-2-{[(2S)-2-azido-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-azido-3-methyl-3-phenylbutanoyl]amino}-3,3-dimethylbutanoyl)(methyl)amino]-2,5-dimethyl-2-hexenoate (0.17 g, 0.35 mmol, from Example 93) is dissolved in methanol (1.5 mL) and tetrahydrofuran (1.5 mL) and cooled to 0° C. (ice water bath). To this solution is added water (0.6 mL) and aqueous lithium hydroxide monohydrate (30 mg, 0.70 mmol). The cooling bath is removed, and the resulting mixture is stirred at 50° C. for 15 hours. Solvents are removed in vacuo to provide a beige foam, which is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a hard white foam (0.20 g, 95%). MS (ES$^+$): (M+H)=486.0

REFERENCE EXAMPLE 29

2-benzyl-3-methyl-3-phenylbutanoic acid

In accordance with a modified literature procedure (Pfeffer, P. E.; Silbert, L. S.; Chirinko, J. M. *J. Org. Chem.* 37(3), 1972, 451-458), a solution of 3,3-dimethyl-3-phenyl propionic acid (0.22 g, 1.2 mmol, from Reference Example 22) in tetrahydrofuran (2 mL) is cooled to −40° C. (dry ice/acetone) while stirring under a nitrogen atmosphere. Lithium diisopropylamide (Aldrich, 2.0 M solution in tetrahydrofuran/ethylbenzene/heptane, 1.4 mL, 2.8 mmol) is added dropwise via syringe, followed by 1,3-dimethyl-3,4,5,6-tetrahydro-2(1H)-pyrimidinone (DMPU, 0.16 mL, 1.3 mmol). The reaction mixture is then allowed to warm to room temperature and to stir for 30 minutes before being re-cooled to 0° C. (ice water bath). Benzyl bromide (0.15 mL, 1.3 mmol) is then added neat via syringe and the reaction mixture is allowed to stir overnight while warming to room temperature. The reaction is quenched by the addition of 10% aqueous hydrochloric acid solution and extracted thrice with ethyl acetate. The combined extracts are washed twice with 10% aqueous hydrochloric acid solution and once with saturated sodium chloride solution, dried over anhydrous sodium sulfite, and concentrated under reduced pressure. Flash chromatography (silica gel, ether/hexanes) is performed to give a straw colored gum (0.91 g, 70% for two combined reactions). MS (ES$^-$): (M−H)=266.9

REFERENCE EXAMPLE 30

2-ethyl-3-methyl-3-phenylbutanoic acid

In accordance with a modified literature procedure (Pfeffer, P. E.; Silbert, L. S.; Chirinko, J. M. *J. Org. Chem.* 37(3), 1972, 451-458), a solution of 3,3-dimethyl-3-phenyl propionic acid (0.47 g, 2.6 mmol, from Reference Example 22) in tetrahydrofuran (4.5 mL) is cooled to −40° C. (dry ice/acetone) while stirring under a nitrogen atmosphere. Lithium diisopropylamide (Aldrich, 2.0 M solution in tetrahydrofuran/ethylbenzene/heptane, 2.9 mL, 5.8 mmol) is added dropwise via syringe, followed by 1,3-dimethyl-3,4,5,6-tetrahydro-2(1 H)-pyrimidinone (DMPU, 0.35 mL, 2.9 mmol). The reaction mixture is then allowed to warm to room temperature and to stir for 30 minutes before being re-cooled to 0° C. (ice water bath). Ethyl iodide (0.31 mL, 3.9 mmol) is then added neat via syringe and the reaction mixture is allowed to stir overnight while warming to room temperature. The reaction is quenched by the addition of 10% aqueous hydrochloric acid solution and extracted thrice with ethyl acetate. The combined extracts are washed twice with 10% aqueous hydrochloric acid solution and once with saturated sodium chloride solution, dried over anhydrous sodium sulfite, and concentrated under reduced pressure. The crude solid is recrystallized from hexanes to afford pure material as a white solid (0.16 g, 30%). MS (ES$^-$): (M−H)=205.0

REFERENCE EXAMPLE 31

2-allyl-3-methyl-3-phenylbutanoic acid

In accordance with a modified literature procedure (Pfeffer, P. E.; Silbert, L. S.; Chirinko, J. M. *J. Org. Chem.* 37(3), 1972, 451-458), a solution of 3,3-dimethyl-3-phenyl propionic acid (0.50 g, 2.8 mmol, from Reference Example 22) in tetrahydrofuran (5 mL) is cooled to −40° C. (dry ice/acetone) while stirring under a nitrogen atmosphere. Lithium diisopropylamide (Aldrich, 2.0 M solution in tetrahydrofuran/ethylbenzene/heptane, 3.1 mL, 6.2 mmol) is added dropwise via syringe, followed by 1,3-dimethyl-3,4,5,6-tetrahydro-2(1 H)-pyrimidinone (DMPU, 0.37 mL, 4.2 mmol). The reaction mixture is then allowed to warm to room temperature and to stir for 30 minutes before being re-cooled to 0° C. (ice water bath). Allyl iodide (0.15 mL, 1.3 mmol) is then added neat via syringe and the reaction mixture is allowed to stir overnight while warming to room temperature. The reaction is quenched by the addition of 10% aqueous hydrochloric acid solution and extracted thrice with ethyl acetate. The combined extracts are washed twice with 10% aqueous hydrochloric acid solution and once with saturated sodium chloride solution, dried over anhydrous sodium sulfite, and concentrated under reduced pressure. Flash chromatography (silica gel, hexane/dichloromethane/ethyl acetate) is performed to give a clear blond oil (0.39 g, 64%). MS (ES$^-$): (M−H)=217.0

REFERENCE EXAMPLE 32

3-methyl-2-(methylsulfanyl)-3-phenylbutanoic acid

In accordance with a modified literature procedure (Pfeffer, P. E.; Silbert, L. S.; Chirinko, J. M. *J. Org. Chem.* 37(3), 1972, 451-458), a solution of 3,3-dimethyl-3-phenyl propionic acid (0.50 g, 2.8 mmol, from Reference Example 22) in tetrahydrofuran (5 mL) is cooled to −40° C. (dry ice/acetone) while stirring under a nitrogen atmosphere. Lithium diisopropylamide (Aldrich, 2.0 M solution in tetrahydrofuran/ethylbenzene/heptane, 3.1 mL, 6.2 mmol) is added dropwise via syringe, followed by 1,3-dimethyl-3,4,5,6-tetrahydro-2(1 H)-pyrimidinone (DMPU, 0.37 mL, 3.1 mmol). The reaction mixture is then allowed to warm to room temperature and to stir for 30 minutes before being re-cooled to 0° C. (ice water bath). Dimethyl disulfide (0.38 mL, 4.2 mmol) is then added neat via syringe and the reaction mixture is allowed to stir for two days while warming to room temperature. The reaction is quenched by the addition of 10% aqueous hydrochloric acid solution and extracted thrice with ethyl acetate. The combined extracts are washed twice with 10% aqueous hydrochloric acid solution and once with saturated sodium chloride solution, dried over anhydrous sodium sulfite, and concentrated under reduced pressure. Flash chromatography (silica gel, hexanes/dichloromethane/methanol) is performed to give a clear light brown oil which solidified upon standing (0.54 g, 86%). TOF MS (ES$^-$): (M−H)=222.9

REFERENCE EXAMPLE 33

3-methyl-2-(methylsulfonyl)-3-phenylbutanoic acid

A solution of 3-methyl-2-(methylsulfanyl)-3-phenylbutanoic acid (0.28 g, 1.2 mmol, from Example 32) in dichloromethane (10 mL) is cooled to 0° C. (ice water bath). Peracetic acid (32% aqueous solution, 0.76 mL, 3.6 mmol) is added quickly via pipette. The cooling bath is then removed and the reaction mixture is stirred at room temperature. After three hours, an additional quantity of peracetic acid (32% aqueous solution, 0.76 mL, 3.6 mmol) is added. After stirring overnight, the reaction is concentrated under reduced pressure, while maintaining a bath temperature of less than 33° C. To the residue, 1.5 M aqueous sodium sulfite solution (20 mL) is added. The quenched reaction mixture is extracted thrice with ethyl acetate. The combined extracts are washed with 10% aqueous hydrochloric acid and saturated aqueous sodium chloride solution, dried over anhydrous sodium sulfate, and concentrated under reduced pressure to give a white powder (0.29 g, 94%). MS (ES$^-$): (M−H)=255.0

EXAMPLE 95

Ethyl (E,4S)-4-[((2S)-3,3-dimethyl-2-{[3-methyl-2-(benzyl)-3-phenylbutanoyl]amino}butanoyl)(methyl)amino]-2,5-dimethyl-2-hexenoate SSS Configuration and RSS Configuration To a solution of 2-benzyl-3-methyl-3-phenylbutanoic acid (0.16 g, 0.60 mmol, from Reference Example 29) in anhydrous dichloromethane (2.5 mL) is added triethylethylamine (0.17 mL, 1.2 mmol) under an inert atmosphere. To this solution is added a solution of ethyl (2E,4S)-2,5-dimethyl-4-[methyl(3-methyl-L-valyl)amino]hex-2-enoate hydrochloride (0.60 mmol, prepared by using the literature procedures: Ref. Andersen, R, WO 96/33211) in anhydrous dichloromethane (4 mmol), containing triethylamine (0.25 mL, 1.8 mmol). To the mixture of acid and amine is added, bis(2-oxo-3-oxazolidinyl)phosphinic chloride (0.17 g, 0.66 mmol). After stirring at room temperature for 15-20 hours, the mixture is diluted with water, and the aqueous layer is extracted with ethyl acetates (3 times). The combined extracts are washed with 10% aqueous hydrochloric acid, 2 M aqueous sodium carbonate solution, and saturated aqueous sodium chloride solution, dried over anhydrous sodium sulfate, filtered and concentrated in vacuo. The residue is chromatographed (silica gel, flash column), to provide a 1:1 mixture of two diastereoisomers (SSS and RSS). MS (ES$^+$): (M+H)=562.9

EXAMPLE 96

(E,4S)-4-[((2S)-3,3-dimethyl-2-{[3-methyl-2-benzyl-3-phenylbutanoyl]amino}butanoyl)(methyl)amino]-2,5-dimethyl-2-hexenoic acid SSS Configuration and RSS Configuration According to General Procedure II, a 1:1 mixture of ethyl (E,4S)-4-[((2S)-2-{[(2S)-2-benzyl-3-methyl-3-phenylbutanoyl]amino}-3,3-dimethylbutanoyl)(methyl)amino]-2,5-dimethyl-2-hexenoate and of ethyl (E,4S)-4-[((2S)-2-{[(2R)-2-azido-3-methyl-3-phenylbutanoyl]amino}-3,3-dimethylbutanoyl)(methyl)amino]-2,5-dimethyl-2-hexenoate (0.17 g, 0.35 mmol, from Example 95) is dissolved in methanol (1.5 mL) and tetrahydrofuran (1.5 mL), and cooled to 0° C. (ice water bath). To this solution is added water (0.75 mL) and lithium hydroxide monohydrate (23 mg, 0.54 mmol). The cooling bath is removed, and the resulting mixture is stirred at 60° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a hard white foam, which is crushed to a powder (0.14 g, 100%). MS (ES$^-$): (M−H)=533.0

EXAMPLE 97

Ethyl (E,4S)-4-[((2S)-3,3-dimethyl-2-{[3-methyl-2-allyl-3-phenylbutanoyl]amino}butanoyl)(methyl)amino]-2,5-dimethyl-2-hexenoate SSS Configuration and RSS Configuration To a solution of 2-allyl-3-methyl-3-phenylbutanoic acid (0.36 g, 1.6 mmol, from Reference Example 31) in anhydrous dichloromethane (7 mL) is added triethylethylamine (0.45 mL, 3.2 mmol) under an inert atmosphere. To this solution is added a solution of ethyl (2E,4S)-2,5-dimethyl-4-[methyl(3-methyl-L-valyl)amino]hex-2-enoate hydrochloride (1.6 mmol, prepared by using the literature procedures: Ref. Andersen, R, WO 96/33211) in anhydrous dichloromethane (15 mL), containing triethylamine (0.66 mL, 4.8 mmol). To the mixture of acid and amine is added, bis(2-oxo-3-oxazolidinyl)phosphinic chloride (0.45 g, 1.8 mmol). After stirring at room temperature for 16 hours, the mixture is diluted with water, and the aqueous layer is extracted with ethyl acetates (3 times). The combined extracts are washed with 10% aqueous hydrochloric acid, 2 M aqueous sodium carbonate solution, and saturated aqueous sodium chloride solution, dried over anhydrous sodium sulfate, filtered and concentrated in vacuo. The residue is chromatographed (silica gel, flash column, hexanes/dichloromethane/ethyl acetate), to provide 0.43 g (52%) of a 1:1 mixture of two diastereoisomers (SSS and RSS). MS (ES$^+$): (M+H)=513.0

EXAMPLE 98

(E,4S)-4-[((2S)-3,3-dimethyl-2-{[3-methyl-2-allyl-3-phenylbutanoyl]amino}butanoyl)(methyl)amino]-2,5-dimethyl-2-hexenoic acid SSS Configuration and RSS Configuration According to general procedure 11, a 1:1 mixture of ethyl (E,4S)-4-[((2S)-2-{[(2S)-2-allyl-3-methyl-3-phenylbutanoyl]amino}-3,3-dimethylbutanoyl)(methyl)amino]-2,5-dimethyl-2-hexenoate and of ethyl (E,4S)-4-[((2S)-2-{[(2R)-2-allyl-3-methyl-3-phenylbutanoyl]amino}-3,3-dimethylbutanoyl)(methyl)amino]-2,5-dimethyl-2-hexenoate (0.38 g, 0.74 mmol, from Example 97) is dissolved in methanol (4 mL) and tetrahydrofuran (4 mL), and cooled to 0° C. (ice water bath). To this solution is added water (2 mL) and lithium hydroxide monohydrate (62 mg, 1.5 mmol). The cooling bath is removed, and the resulting mixture is stirred at 60° C. for 15 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a hard white foam, which is crushed to a powder (0.32 g, 89%). MS (ES$^+$): (M+H)=485.0

EXAMPLE 99

Ethyl (E,4S)-4-[((2S)-3,3-dimethyl-2-{[3-methyl-2-ethyl-3-phenylbutanoyl]amino}butanoyl)(methyl)amino]-2,5-dimethyl-2-hexenoate SSS Configuration and RSS Configuration To a solution of 2-ethyl-3-methyl-3-phenylbutanoic acid (0.22 g, 1.1 mmol, obtained from Reference Example 30) in anhydrous dichloromethane (5 mL) is added triethylethylamine (0.30 mL, 2.2 mmol) under an inert atmosphere. To this solution is added a solution of ethyl (2E,4S)-2,5-dimethyl-4-[methyl(3-methyl-L-valyl)amino]hex-2-enoate hydrochloride (1.1 mmol, prepared by using the literature procedures: Ref. Andersen, R, WO 96/33211) in anhydrous dichloromethane (8 mL), containing triethylamine (0.45 mL, 3.3 mmol). To the mixture of acid and amine is added, bis(2-oxo-3-oxazolidinyl)phosphinic chloride (0.30 g, 1.2 mmol). After stirring at room temperature for 16 hours, the mixture is diluted with water, and the aqueous layer is extracted with ethyl acetates (3 times). The combined extracts are washed with 2% aqueous hydrochloric acid, twice with saturated aqueous sodium bicarbonate solution, and saturated aqueous sodium chloride solution, dried over anhydrous sodium sulfate, filtered and concentrated in vacuo. The residue is chromatographed (silica gel, flash column, hexanes/dichloromethane/ethyl acetate), to provide 0.25 g (45%) of a 1:1 mixture of two diastereoisomers (SSS and RSS) as a hard white foam, which is crushed to a powder. MS (ES$^+$): (M+H)=501.0

EXAMPLE 100

(E,4S)-4-[((2S)-3,3-dimethyl-2-{[3-methyl-2-ethyl-3-phenylbutanoyl]amino}butanoyl)(methyl)amino]-2,5-dimethyl-2-hexenoic acid SSS Configuration and RSS Configuration According to General Procedure II, a 1:1 mixture of ethyl (E,4S)-4-[((2S)-2-{[(2S)-2-ethyl-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-ethyl-3-methyl-3-phenylbutanoyl]amino}-3,3-dimethylbutanoyl)(methyl)amino]-2,5-dimethyl-2-hexenoate (0.22 g, 0.44 mmol, from Example 99) is dissolved in methanol (2 mL) and tetrahydrofuran (2 mL), and cooled to 0° C. (ice water bath). To this solution is added water (1 mL) and lithium hydroxide monohydrate (37 mg, 0.88 mmol). The cooling bath is removed, and the resulting mixture is stirred at 60° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a tan foam (0.21 g, 100%). MS (ES$^+$): (M+H)=473.0

EXAMPLE 101

Ethyl (E,4S)-4-[((2S)-3,3-dimethyl-2-{[3-methyl-2-methylsulfanyl-3-phenylbutanoyl]amino}butanoyl)(methyl)amino]-2,5-dimethyl-2-hexenoate SSS Configuration and RSS Configuration To a solution of 2-methylsulfanyl-3-methyl-3-phenylbutanoic acid (0.25 g, 1.1 mmol, obtained from Reference Example 32) in anhydrous dichloromethane (5 mL) is added triethylethylamine (0.30 mL, 2.2 mmol) under an inert atmosphere. To this solution is added a solution of ethyl (2E,4S)-2,5-dimethyl-4-[methyl(3-methyl-L-valyl)amino]hex-2-enoate hydrochloride (1.1 mmol, prepared by using the literature procedures: Ref. Andersen, R, WO 96/33211) in anhydrous dichloromethane (8 mL), containing triethylamine (0.45 mL, 3.3 mmol). To the mixture of acid and amine is added, bis(2-oxo-3-oxazolidinyl)phosphinic chloride (0.30 g, 1.2 mmol). After stirring at room temperature for 16 hours, the mixture is diluted with water, and the aqueous layer is extracted with ethyl acetates (3 times). The combined extracts are washed with 2% aqueous hydrochloric acid, twice with saturated aqueous sodium bicarbonate solution, and saturated aqueous sodium chloride solution, dried over anhydrous sodium sulfate, filtered and concentrated in vacuo. The residue is chromatographed (silica gel, flash column, hexanes/dichloromethane/ethyl acetate), to provide 0.24 g (42%) of a 1:1 mixture of two diastereoisomers (SSS and RSS) as a sticky, tan foam. MS (ES$^+$): (M+H)=519.0

EXAMPLE 102

(E,4S)-4-[((2S)-3,3-dimethyl-2-{[3-methyl-2-methylsulfanyl-3-phenylbutanoyl]amino}butanoyl)(methyl)amino]-2,5-dimethyl-2-hexenoic acid SSS Configuration and RSS Configuration According to General Procedure II, a 1:1 mixture of ethyl (E,4S)-4-[((2S)-2-{[(2S)-2-methylsulfanyl-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-methylsulfanyl-3-methyl-3-phenylbutanoyl]amino}-3,3-dimethylbutanoyl)(methyl)amino]-2,5-dimethyl-2-hexenoate (0.20 g, 0.39 mmol, from Example 101) is dissolved in methanol (2 mL) and tetrahydrofuran (2 mL), and cooled to 0° C. (ice water bath). To this solution is added water (1 mL) and lithium hydroxide monohydrate (33 mg, 0.78 mmol). The cooling bath is removed, and the resulting mixture is stirred at 60° C. for 15 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a light tan powder (0.20 g,>100%). MS (ES$^+$): (M+H)=490.9

REFERENCE EXAMPLE 34

Ethyl (E,4S)-4-[((2S)-3,3-dimethyl-2-{[3-methyl-2-methylsulfonyl-3-phenylbutanoyl]amino}butanoyl)(methyl)amino]-2,5-dimethyl-2-hexenoate SSS Configuration and RSS Configuration To a solution of 2-methylsulfonyl-3-methyl-3-phenylbutanoic acid (0.27 g, 1.1 mmol, from Reference Example 33) in anhydrous dichloromethane (5 mL) is added triethylethylamine (0.30 mL, 2.2 mmol) under an inert atmosphere. To this solution is added a solution of ethyl (2E,4S)-2,5-dimethyl-4-[methyl(3-methyl-L-valyl)amino]hex-2-enoate hydrochloride (1.1 mmol, prepared by using the literature procedures: Ref. Andersen, R, WO 96/33211) in anhydrous dichloromethane (8 mL), containing triethylamine (0.45 mL, 3.3 mmol). To the mixture of acid and amine is added, bis(2-oxo-3-oxazolidinyl)phosphinic chloride (0.30 g, 1.2 mmol). After stirring at room temperature for 16 hours, the mixture is diluted with water, and the aqueous layer is extracted with ethyl acetates (3 times). The combined extracts are washed with 2% aqueous hydrochloric acid, twice with saturated aqueous sodium bicarbonate solution, and saturated aqueous sodium chloride solution, dried over anhydrous sodium sulfate, filtered and concentrated in vacuo. The residue is purified by reverse-phase HPLC (water/acetonitrile) to provide 0.20 g (33%) of a 1:1 mixture of two diastereoisomers (SSS and RSS) as a white powder. MS (ES$^+$): (M+H)=551.3

EXAMPLE 103

(E,4S)-4-[((2S)-3,3-dimethyl-2-{[3-methyl-2-methylsulfonyl-3-phenylbutanoyl]amino}butanoyl)(methyl)amino]-2,5-dimethyl-2-hexenoic acid SSS Configuration and RSS Configuration According to General Procedure II, a 1:1 mixture of ethyl (E,4S)-4-[((2S)-2-{[(2S)-2-methylsulfonyl-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-methylsulfonyl-3-methyl-3-phenylbutanoyl]amino}-3,3-dimethylbutanoyl)(methyl)amino]-2,5-dimethyl-2-hexenoate (0.17 g, 0.31 mmol, from Reference Example 34) is dissolved in methanol (1.5 mL) and tetrahydrofuran (1.5 mL), and cooled to 0° C. (ice water bath). To this solution is added water (0.75 mL) and lithium hydroxide monohydrate (26 mg, 0.62 mmol). The cooling bath is removed, and the resulting mixture is stirred at 55-60° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a hard white foam, which is crushed to a powder (0.17 g, >100%). TOF MS (ES$^-$): (M−H)=521.0

REFERENCE EXAMPLE 35

3-phenyl-3-methyl-2-oxobutanoic acid

To a 500 mL 3-neck round-bottom flask equipped with a reflux condenser and magnetic stirrer containing 3-phenyl-2-oxopropanoic acid (25 g, 150 mmol) as a solution in tetrahydrofuran (130 mL) and water (50 mL) is added 5 M sodium hydroxide solution (80 mL) and iodomethane (25 mL, 400 mmol). While stirring under a nitrogen atmosphere, the reaction mixture is heated in a 68-71° C. oil bath for 5½ hours. After this interval had passed, additional volumes of 5 N NaOH (50 mL) and iodomethane (10 mL) are added. The reaction mixture is allowed to stir for 2 days at room temperature, then volatiles are evaporated under reduced pressure. The aqueous residue is extracted thrice with ethyl acetates and then acidified to pH 1 by the addition of concentrated hydrochloric acid. The acidified phase is extracted thrice with ethyl acetates. The combined extracts are washed twice with saturated aqueous sodium chloride solution, dried over anhydrous sodium sulfate, decanted, and concentrated under reduced pressure to afford a dark burgundy liquid (31 g,>100%). MS (ES$^-$): (M−H)=190.8

REFERENCE EXAMPLE 36

Methyl 3-phenyl-3-methyl-2-oxobutanoate

To a 0° C. (ice water bath) solution of 3-phenyl-3-methyl-2-oxobutanoate (9.0 g, 47 mmol, from Reference Example 35) in ether (40 mL) and methanol (60 mL). Trimethylsilyl diazomethane (2.0 M solution in hexanes, 35 mL, 70 mmol, Aldrich) is added dropwise until the evolution of gas ceased and the yellow color of the reagent persisted in solution. The solvents are evaporated under reduced pressure and the residue is taken up in ether/hexanes (1:1) and washed with 2% aqueous hydrochloric acid, saturated aqueous sodium bicarbonate solution, and saturated aqueous sodium chloride solution. The combined extracts are then dried over anhydrous sodium sulfate, and concentrated under reduced pressure to give a straw-colored liquid (8.5 g, 88%). MS (ES$^+$): (M+H)=206.9

REFERENCE EXAMPLE 37

Methyl 2-hydroxy-3-methyl-3-phenylbutanoate

Following a procedure found in the literature (Ferguson, C. G.; Money, T.; Pontillo, J.; Whitelaw, P. D. M.; Wong, M. K. C. *Tetrahedron*. 52(47), 1996, 14661-14627) a solution of methyl 3-phenyl-3-methyl-2-oxobutanoate (2.5 g, 12 mmol, from Reference Example 36) in methanol (144 mL) is cooled to 0° C. (ice water bath). Sodium borohydride (0.21 g, 5.5 mmol) is added in three portions over 3 minutes. The reaction mixture is stirred at 0° C. for 10 minutes and then at room temperature for 30 minutes. The reaction mixture is quenched by the addition of 10% aqueous hydrochloric acid solution until pH=6 and then extracted thrice with diethyl ether. The combined extracts are washed with water and saturated aqueous sodium chloride solution, dried over anhydrous sodium sulfite, and concentrated under reduced pressure to give a light blond liquid, which is combined with the crude material from another reaction. The combined crude material is subjected to flash chromatography to (silica gel, hexanes/ethyl acetate) and provided 2.4 g (80% combined yield) of a clear, colorless oil. TOF MS (ES$^+$): (M+H)=209.1

REFERENCE EXAMPLE 38

Methyl 2-methoxy-3-methyl-3-phenylbutanoate

To a solution of methyl 2-hydroxy-3-methyl-3-phenylbutanoate (0.50 g, 2.4 mmol, from Reference Example 37) in diethyl ether (11 mL) is added silver (I) oxide (4.3 g) and iodomethane (8.7 mL). The reaction mixture is stirred in a 40° C. oil bath under nitrogen atmosphere for 26 hours. The reaction mixture is combined with that from a previous run conducted under the same conditions and filtered through a plug of diatomaceous earth. The filtrate is concentrated under reduced pressure and then purified by flash chromatograhy (silica gel, hexanes/ethyl acetate) to furnish 0.52 g of a clear, colorless liquid (68% combined yield). MS (ES$^+$): (M+H)=222.9

REFERENCE EXAMPLE 39

2-methoxy-3-methyl-3-phenylbutanoic acid

According to General Procedure II, methyl 2-methoxy-3-methyl-3-phenylbutanoic acid (0.49 g, 2.2 mmol, from Reference Example 38) is dissolved in methanol (10 mL) and tetrahydrofuran (10 mL). To this solution is added water (5 mL) and lithium hydroxide monohydrate (0.18 g, 4.4 mmol), and the resulting mixture is stirred at 60° C. for 16 hours. Solvents are removed in vacuo and the residue is then dissolved in water. The solution is acidified to pH 1 with 10% aqueous hydrochloric acid solution and then extracted thrice with ethyl acetate. The combined extracts are washed with saturated sodium chloride solution, dried over anhydrous sodium sulfate, decanted, and concentrated under reduced pressure to afford a light orange oil, which solidified to a straw colored crystalline solid (0.46 g, 100%). MS (ES$^-$): (M−H)=207.0

EXAMPLE 104

Ethyl (E,4S)-4-[{(2S)-2-[(2-methoxy-3-methyl-3-phenylbutanoyl)amino]-3,3-dimethylbutanoyl}(methyl)amino]-2,5-dimethyl-2-hexenoate SSS Configuration and RSS Configuration To a solution of 2-methoxy-3-methyl-3-phenylbutanoic acid (0.43 g, 2.1 mmol, from Reference Example 39), hydroxybenzotriazole (0.33 g, 2.5 mmol) and 1-(3-dimethylaminopropyl)-3-ethylcarbodiimide hydrochloride (0.55 g, 2.9 mmol) in anhydrous dimethylformamide (7 ml) is added N-methylmorpholine (0.34 mL, 3.1 mmol) via syringe under an inert atmosphere. After stirring for 1 hour at room temperature, a solution of ethyl (2E,4S)-2,5-dimethyl-4-[methyl (3-methyl-L-valyl)amino]hex-2-enoate hydrochloride (2.1 mmol) is added. The resulting mixture is stirred for 70 hours at room temperature under an inert atmosphere. The mixture is diluted with water, and the aqueous layer is extracted with diethyl ether (3 times). The combined extracts are washed with 2% aqueous hydrochloric acid (×2), saturated aqueous sodium bicarbonate solution (×2), water, and saturated aqueous sodium chloride. The extracts are dried over anhydrous sodium sulfate, filtered and concentrated in vacuo to give a 1:1 SSS to RSS mixture of ethyl (E,4S)-4-[{(2S)-2-[(2-methoxy-3-methyl-3-phenylbutanoyl)amino]-3,3-dimethylbutanoyl}(methyl)amino]-2,5-dimethyl-2-hexenoate as a pale straw colored gum (1.0 g, 91%). MS (ES$^+$): (M+H)=503.0

EXAMPLE 105

(E,4S)-4-[{N-[(2S)-2-methoxy-3-methyl-3-phenylbutanoyl]-3-methyl-L-valyl}(methyl)amino]-2,5-dimethyl-2-hexenoic acid According to General Procedure II, a 1:1 mixture of ethyl (E,4S)-4-[((2S)-2-{[(2S)-2-methoxy-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-methoxy-3-methyl-3-phenylbutanoyl]amino}-3,3-dimethylbutanoyl)(methyl)amino]-2,5-dimethyl-2-hexenoate (1.0 g, 2.0 mmol, from Reference Example 104) is dissolved in methanol (10 mL) and tetrahydrofuran (10 mL). To this solution is added water (5 mL) and lithium hydroxide monohydrate (0.17 g, 4.0 mmol), and the resulting mixture is stirred at 60° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a white foam. A sample of this crude material (240 mg) is subjected to HPLC purification (Prodigy OS3 column, acetonitrile/water/TFA) to give (E,4S)-4-[{N-[(2S)-2-methoxy-3-methyl-3-phenylbutanoyl]-3-methyl-L-valyl}(methyl)amino]-2,5-dimethyl-2-hexenoic acid as a hard white foam (50 mg). MS (ES$^+$): (M+H)=475.0

EXAMPLE 106

(E,4S)-4-[{N-[(2R)-2-methoxy-3-methyl-3-phenylbutanoyl]-3-methyl-L-valyl}(methyl)amino]-2,5-dimethyl-2-hexenoic acid According to General Procedure II, a 1:1 mixture of ethyl (E,4S)-4-[((2S)-2-{[(2S)-2-methoxy-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-methoxy-3-methyl-3-phenylbutanoyl]amino}-3,3-dimethylbutanoyl)(methyl)amino]-2,5-dimethyl-2-hexenoate (1.0 g, 2.0 mmol, from Reference Example 104) is dissolved in methanol (10 mL) and tetrahydrofuran (10 mL). To this solution is added water (5 mL) and lithium hydroxide monohydrate (0.17 g, 4.0 mmol), and the resulting mixture is stirred at 60° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a white foam. A sample of this crude material (240 mg) is subjected to HPLC purification (Prodigy OS3 column, acetonitrile/water/TFA) to give (E,4S)-4-[(N-[(2R)-2-methoxy-3-methyl-3-phenylbutanoyl]-3-methyl-L-valyl}(methyl)amino]-2,5-dimethyl-2-hexenoic acid as a clear colorless oil (80 mg). MS (ES$^+$): (M+H)=475.0

REFERENCE EXAMPLE 40

2-hydroxy-3-methyl-3-phenylbutanoic acid

According to general procedure, methyl 2-hydroxy-3-methyl-3-phenylbutanoic acid (0.27 g, 1.3 mmol, from Reference Example 37) is dissolved in methanol (6 mL) and tetrahydrofuran (6 mL). To this solution is added water (3 mL) and lithium hydroxide monohydrate (0.12 g, 2.9 mmol), and the resulting mixture is stirred at 60-65° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a light pink oil, which solidified under vacuum (0.25 g, 100%). TOF MS (ES$^-$): (M−H)=193.0

REFERENCE EXAMPLE 41

Ethyl (E,4S)-4-[{(2S)-2-[(2-hydroxy-3-methyl-3-phenylbutanoyl)amino]-3,3-dimethylbutanoyl}(methyl)amino]-2,5-dimethyl-2-hexenoate SSS Configuration and RSS Configuration To a solution of 2-hydroxy-3-methyl-3-phenylbutanoic acid (0.23 g, 1.2 mmol, from Reference Example 40), hydroxybenzotriazole (0.19 g, 1.4 mmol) and 1-(3-dimethylaminopropyl)-3-ethylcarbodiimine hydrochloride (0.33 g, 1.7 mmol) in anhydrous dimethylformamide (4 ml) is added N-methylmorpholine (0.20 mL, 1.8 mmol) via syringe under an inert atmosphere. After stirring for 1 hour at room temperature, a solution of ethyl (2E,4S)-2,5-dimethyl-4-[methyl (3-methyl-L-valyl)amino]hex-2-enoate hydrochloride (1.2 mmol) in anhydrous dimethylformamide (4 ml) is added. The resulting mixture is stirred for 15 hours at room temperature under an inert atmosphere. The mixture is diluted with water, and the aqueous layer is extracted with diethyl ether (3 times). The combined extracts are washed thrice with 2% aqueous hydrochloric acid, saturated aqueous sodium bicarbonate solution, and saturated aqueous sodium chloride. The extracts are dried over anhydrous sodium sulfate, filtered and concentrated in vacuo to give a white powder (0.39 g, 66%). MS (ES$^+$): (M+H)=489.6

EXAMPLE 107 AND EXAMPLE 108

(E,4S)-4-[{(2S)-2-[(2-hydroxy-3-methyl-3-phenylbutanoyl)amino]-3,3-dimethylbutanoyl}(methyl) amino]-2,5-dimethyl-2-hexenoic acid SSS Configuration and RSS Configuration

EXAMPLE 107

(E,4S)-4-[{N-[(2S)-2-hydroxy-3-methyl-3-phenylbutanoyl]-3-methyl-L-valyl}(methyl)amino]-2,5-dimethyl-2-hexenoic acid A 1:1 mixture of ethyl (E,4S)-4-[((2S)-2-{[(2S)-2-hydroxy-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-hydroxy-3-methyl-3-phenylbutanoyl]amino}-3,3-dimethylbutanoyl)(methyl)amino]-2,5-dimethyl-2-hexenoate (0.34 g, 0.70 mmol, from Reference Example 41) is dissolved in methanol (3.2 mL) and tetrahydrofuran (3.2 mL). To this solution is added water (1.6 mL) and lithium hydroxide monohydrate (64 mg, 1.5 mmol), and the resulting mixture is stirred at 65° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a white foam. A sample of this crude material (200 mg) is subjected to HPLC purification (Prodigy OS3 column, acetonitrile/water/TFA) to give (E,4S)-4-[{N-[(2S)-2-hydroxy-3-methyl-3-phenylbutanoyl]-3-methyl-L-valyl}(methyl)amino]-2,5-dimethyl-2-hexenoic acid as a hard white foam, which is crushed into a powder (50 mg). MS (ES$^+$): (M+H)=461.0

EXAMPLE 108

(E,4S)-4-[{N-[(2R)-2-hydroxy-3-methyl-3-phenylbutanoyl]-3-methyl-L-valyl}(methyl)amino]-2,5-dimethyl-2-hexenoic acid A 1:1 mixture of ethyl (E,4S)-4-[((2S)-2-{[(2S)-2-hydroxy-3-methyl-3-phenylbutanoyl]amino}-3,3-dimethylbutanoyl)(methyl)amino]-2,5-dimethyl-2-hexenoate and ethyl (E,4S)-4-[((2S)-2-{[(2R)-2-hydroxy-3-methyl-3-phenylbutanoyl]amino}-3,3-dimethylbutanoyl)(methyl)amino]-2,5-dimethyl-2-hexenoate (0.34 g, 0.70 mmol, from Reference Example 41) is dissolved in methanol (3.2 mL) and tetrahydrofuran (3.2 mL). To this solution is added water (1.6 mL) and lithium hydroxide monohydrate (64 mg, 1.5 mmol), and the resulting mixture is stirred at 65° C. for 16 hours. Solvents are removed in vacuo and the residue is then dissolved in water. The solution is acidified to pH 1 with 2 M aqueous hydrochloric acid solution and then extracted thrice with ethyl acetate. The combined extracts are washed with saturated sodium chloride solution, dried over anhydrous sodium sulfate, decanted, and concentrated under reduced pressure to afford a white foam. A sample of this crude material (200 mg) is subjected to HPLC purification (Prodigy OS3 column, acetonitrile/water/TFA) to give (E,4S)-4-[{N-[(2R)-2-hydroxy-3-methyl-3-phenylbutanoyl]-3-methyl-L-valyl}(methyl)amino]-2,5-dimethyl-2-hexenoic acid as a white foam, which is crushed to a powder (50 mg). MS (ES$^+$): (M+H)=461.0

EXAMPLE 109

(2S)-N-[(1S,2E)-4-hydrazino-1-isopropyl-3-methyl-4-oxo-2-butenyl]-N,3,3-trimethyl-{[(2S)-3-methyl-2-(methylamino)-3-phenylbutanoyl]amino}butanamide To 150 mg of 4-[[(2S)-3,3-dimethyl-2-[[(2S)-3-methyl-2-(methylamino)-1-oxo-3-phenylbutyl]amino)]-1-oxobutyl]methylamino]-2,5-dimethyl-(E, 4S)-2-hexenoic acid in 25 mL of acetonitrile at 0° C. is added 95 mg of N-hydroxysuccinimide and 150 mg of 1-[3-(dimethylamino)propyl]-3-ethylcarbodiimide hydrochloride. This reaction is allowed to stir overnight at ambient temperature before adding 200 uL of hydrazine hydrate in 5 mL of methanol. After an additional 3 hours at ambient temperature the reaction is poured into a mixture of brine and saturated aqueous sodium bicarbonate, and this aqueous mixture is extracted three times with chloroform. The combined chloroform is dried with magnesium sulfate and purified by flash chromatography on silica gel with a gradient of 0-4% methanol in chloroform. The concentrated, pooled fractions containing product are precipitated from ether into hexanes and then filtered and dried to give 91 mg of (2S)-N-[(1S,2E)-4-hydrazino-1-isopropyl-3-methyl-4-oxo-2-butenyl]-N,3,3-trimethyl-2-{[(2S)-3-methyl-2-(methylamino)-3-phenylbutanoyl]amino}butanamide as an off-white powder and 37 mg of the same product from the concentrated mother liquor as a yellowish solid foam (83% total yield). HRMS (ESI): (M+H)=488.35952 (−0.34 mmu).

What is claimed is:

1. A compound represented by Formula I:

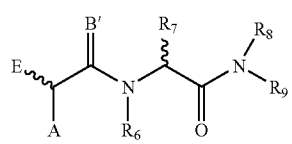

wherein:

A is selected from the group consisting of an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —CN, —CO$_2$H, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, —SO$_2$R$_{10}$, wherein R$_{10}$ is an alkyl moiety of 1 to 10 carbon atoms, alkenyl moiety of 2 to 10 carbon atoms, aryl and a cyclic hydrocarbon moiety of 3 to 10 carbon atoms, aryl-R— and heteroaryl-R; or A is OR, S(O)R, S(O)$_2$R, SO$_2$NR$_2$, NR$_1$R$_2$ or N$_3$;

R is selected from the group consisting of H, an alkyl moiety of 1 to 18 carbon atoms, alkenyl moiety of 2 to 18 carbon atoms, aryl and a cyclic hydrocarbon moiety of 3 to 18 carbon atoms, wherein carbon atoms may optionally be replaced with 0 to 4 nitrogen atoms, 0 to 4 oxygen atoms, and 0 to 4 sulfur atoms, and the carbon atoms are optionally substituted with: =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

B' is O or H$_2$;

E is the moiety

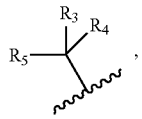

or aryl, a 5 to 14-membered monocyclic, bicyclic or tricyclic saturated or unsaturated hydrocarbon ring moiety wherein carbon atoms may optionally be replaced with 0 to 4 nitrogen atoms, 0 to 4 oxygen atoms, and 0 to 4 sulfur atoms wherein the carbon atoms may optionally be substituted with: R, =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —CN, —CO$_2$H, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SOR$_{10}$;

R$_1$ is selected fmm the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —CN, —CO$_2$H, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SOR$_{10}$;

R$_2$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —ON, —CO$_2$H, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SOR$_{10}$;

R$_1$ and R$_2$ together may optionally form a ring of 3 to 7 carbon atoms wherein carbon atoms may optionally be replaced with 0 to 2 nitrogen atoms, 0 to 2 oxygen atoms and 0 to 2 sulfur atoms;

R$_3$ is selected from the group consisting of H, an alkyl moiety of 1 to 10 carbon atoms, alkenyl moiety, of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —ON, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_4$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —S$_2$R$_{10}$;

R$_3$ and R$_4$ together may optionally form a ring of 3 to 7 carbon atoms wherein carbon atoms may optionally be replaced with 0 to 2 nitrogen atoms, 0 to 2 oxygen atoms and 0 to 2 sulfur atoms;

R$_5$ is selected from the group consisting of H, OH, NHR, SH, aryl, heteroaryl, an alkyl moiety of 1 to 10 carbon atoms, alkenyl moiety of 2 to 10 carbon atoms and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_5$ and A may optionally form a ring of 5 to 7 carbon atoms wherein carbon atoms may optionally be replaced with 0 to 2 nitrogen atoms, 0 to 2 oxygen atoms, and 0 to 2 sulfur atoms;

R$_6$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F, —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SOR$_{10}$;

R$_7$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, Br, —Cl, —F —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

R$_8$ is selected from the group consisting of H, an alkyl moiety of 1 to 10 carbon atoms, alkenyl moiety of 2 to 10 carbon atoms, aryl and a cyclic hydrocarbon moiety of 3 to 10 carbon atoms, wherein carbon atoms may optionally be replaced with 0 to 4 nitrogen atoms, 0 to 4 oxygen atoms, and 0 to 4 sulfur atoms, and the carbon atoms may optionally be substituted with: =O, =S, —OH, —OR$_{10}$, —O$_2$CR$_{10}$, —SH, —SR$_{10}$, —SOCR$_{10}$, —NH$_2$, —NR$_{10}$H, —N(R$_{10}$)$_2$, —NHCOR$_{10}$, —NR$_{10}$COR$_{10}$, —I, —Br, —Cl, —F —CN, —CO$_2$H, —CO$_2$R$_{10}$, —CHO, —COR$_{10}$, —CONH$_2$, —CONHR$_{10}$, —CON(R$_{10}$)$_2$, —COSH, —COSR$_{10}$, —NO$_2$, —SO$_3$H, —SOR$_{10}$, or —SO$_2$R$_{10}$;

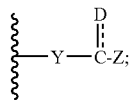

R$_9$ is selected from
D is O or OH;
Y is an alkyl moiety of 1 to 10 carbon atoms optionally substituted with R, AryIR-, or
X, or an alkenyl moiety of 2 to 10 carbon atoms optionally substituted with R, AryIR-, or X;
Z is defined as a moiety selected from the group consisting of: pyrrolidinyl, pyrrolyl and
a moiety of formula

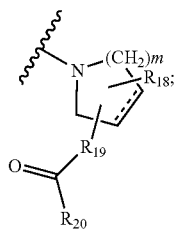

the dotted line is an optional bond;
m is 1;
R$_{18}$ is H or OH;
R$_{19}$ is selected from a bond, an alkyl moiety of 1 to 10 carbon atoms optionally substituted with an alkyl moiety of 1 to 10 carbon atoms, and alkoxy of 1 to 10 carbon atoms;
R$_{20}$ is selected from OR$_{14}$, NH—R$_{21}$, a moiety of the formula

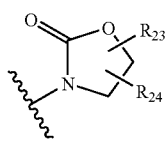

and a moiety of the formula

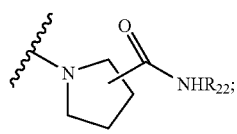

R$_{21}$ is an alkyl moiety of 1 to 10 carbon atoms optionally substituted with aryl and heteroaryl;
R$_{22}$ is an alkyl moiety of 1 to 10 carbon atoms optionally substituted with aryl;
X is defined as a moiety selected from the group consisting of: —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R;

Aryl is defined as an aromatic hydrocarbon moiety having 6, 10 or 14 carbon atoms, optionally substituted with R or Z;
Heteroaryl means a 5- or 6-membered heterocyclic ring, which may be fused to another 5- or 6-membered heterocyclic ring, especially heteroaromatic rings which contain 1 to 3 heteroatoms independently selected from O, N and S optionally substituted with R or X or fused to a cyclic hydrocarbon moiety of 3 to 10 carbon atoms;
or pharmaceutically acceptable salts thereof.

2. A compound according to claim 1 wherein:
(a) R$_1$ is H, methyl, ethyl, propyl, or n-butyl and R$_2$ is methyl, ethyl, propyl, or n-butyl; or
(b) where R$_1$ and R$_2$ taken together with the nitrogen atom to which they are attached form a three to six membered ring.

3. A compound according to claim 2 wherein R$_1$ is H and R$_2$ is CH$_3$.

4. A compound according to claim 1 wherein no more than one of R$_3$ and R$_4$ is H.

5. A compound according to claim 1 wherein R$_3$ and R$_4$ are independently: methyl, ethyl, n-propyl or n-butyl.

6. A compound according to claim 1 wherein R$_3$ and R$_4$ are each methyl.

7. A compound according to claim 1 wherein R$_3$ and R$_4$ are joined together to form a β-cyclopropyl, β-cyclobutyl, β-cyclopentyl or β-cyclohexyl ring.

8. A compound according to claim 1 wherein R$_5$ is aryl.

9. A compound according to claim 1 wherein R$_5$ is phenyl, or naphthyl.

10. A compound according to claim 1 wherein R$_5$ is phenyl.

11. A compound according to claim 1 wherein R$_5$ is cyclohexyl.

12. A compound according to claim 1 wherein E is phenyl, adamantly, or 2,3,4-tetrahydro-1-naphthalenyl.

13. A compound according to claim 1 wherein R$_8$ is H and R$_8$ is methyl.

14. A compound according to claim 1 wherein R$_7$ is a three to six carbon, branched alkyl group.

15. A compound according to claim 14 wherein R$_7$ is —C(CH$_3$)$_3$.

16. A compound according to claim 1 wherein R$_9$ is —C(R$_{15}$)—C=C(R$_{16}$)C(O)-Z wherein R$_{15}$ is methyl, ethyl, n-propyl, isopropyl, tert-butyl, iso-butyl, or sec-butyl and R$_{16}$ is H, methyl, ethyl, propyl, iso-propyl, n-butyl, iso-butyl or sec-butyl.

17. A compound according to claim 1 wherein R$_9$ is:

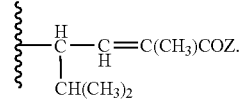

18. A compound according to claim 16 wherein R$_9$ is

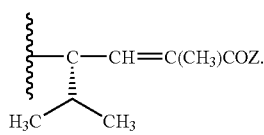

19. A compound according to claim 17 wherein $R_9$ is

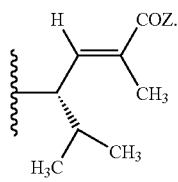

20. A compound according to claim 1 wherein:
A is $NR_1R_2$;
$R_1$ is methyl;
$R_2$ is H;
$R_3$ and $R_4$ are methyl;
$R_5$ is selected from the group consisting of H, an alkyl moiety of 1 to 10 carbon atoms, aryl and a cyclic hydrocarbon moiety of 3 to 10 carbon atoms, said carbon atoms being optionally substituted with: =O, =S, —OH, —$OR_{10}$, —$O_2CR_{10}$, —SH, —$SOCR_{10}$, —$NH_2$, —$NR_{10}H$, —$N(R_{10})_2$, —$NHCOR_{10}$, —$NR_{10}COR_{10}$, —I, —Br, —Cl, —F, —CN, —$CO_2H$, —$CO_2R_{10}$, —CHO, —$COR_{10}$, —$CONH_2$, —$CONHR_{10}$, —$CON(R_{10})_2$, —COSH, —$COSR_{10}$, —$NO_2$, —$SO_3H$, —$SOR_{10}$, or —$SO_2R_{10}$, wherein $R_{10}$ is an alkyl moiety of 1 to 10 carbon atoms, alkenyl moiety of 2 to 10 carbon atoms, aryl and a cyclic hydrocarbon moiety of 3 to 10 carbon atoms, aryl-R— and heteroaryl-R;
$R_7$ is t-butyl;
$R_9$ is —$C(R_{15})$—C=$C(R_{16})C(O)$-Z wherein $R_{15}$ is methyl, ethyl, n-propyl, isopropyl, tert-butyl, iso-butyl, or sec-butyl and $R_{16}$ is H, methyl, ethyl, propyl, isopropyl, n-butyl, iso-butyl or sec-butyl;
or pharmaceutically acceptable salts thereof.

21. A compound according to claim 20 wherein:
$R_9$ is:

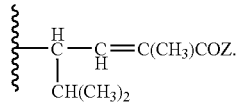

22. A compound according to claim 21 wherein:
$R_9$ is

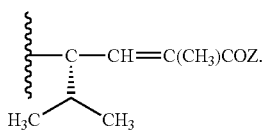

23. A compound according to claim 22 wherein:
$R_9$ is

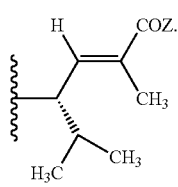

24. A compound according to claim 1 wherein the absolute configurations of moieties a, b and c of Formula (I)

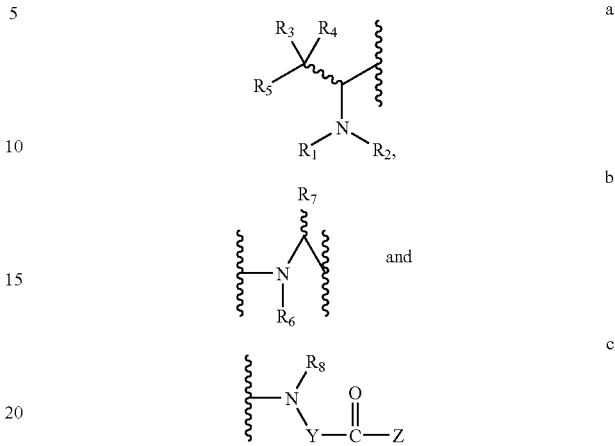

are selected from:

| a | b | c |
|---|---|---|
| S | S | S |
| R | S | S and |
| S | S | R. |

25. The compound according to claim 1, N, β,β,3,4-Pentamethyl-L-phenylalanyl-$N^1$-{(1S,2E)-4-[(2S)-2-(methoxycarbonyl)pyrrolidin-1-yl]-1-isopropyl-3-methyl-4-oxobut-2-enyl}-$N^1$,3-dimethyl-L-valinamide or a pharmaceutically acceptable salt thereof.

26. The compound according to claim 1, N, β,β,3,4-Pentamethyl-L-phenylalanyl-$N^1$-{( 1 S,2E)-4-[(2S)-2-carboxypyrrolidin-1-yl]-1-isopropyl-3-methyl-4-oxobut-2-enyl}$N^1$,3-dimethyl-L-valinamide or a pharmaceutically acceptable salt thereof.

27. The compound according to claim 1, N, β,β,3,5Pentamethyl-L-phenylalanyl-$N^1$-{(1S,2E)-4-[(2S)-2-(methoxycarbonyl)pyrrolidin-1-yl]-1-isopropyl-3-methyl-4-oxobut-2-enyl}$N^1$,3-dimethyl-L-valinamide or a pharmaceutically acceptable salt thereof.

28. The compound according to claim 1, N, ββ,3,5-Pentamethyl-L-phenylalanyl-$N^1$-{(1S,2E)-4-[(2S)-2-carboxypyrrolidin-1-yl]-1-isopropyl-3-methyl-4-oxobut-2-enyl}-$N^1$,3-dimethyl-L-valinamide or a pharmaceutically acceptable salt thereof.

29. The compound according to claim 1, N, ββ,3-Tetramethyl-L-phenylalanyl-$N^1$-{(1S,2E)-4-[(2S)-2-(methoxycarbonyl)pyrrolidin-1-yl]-1-isopropyl-3-methyl-4-oxobut-2-enyl}-$N^1$,3-dimethyl-L-valinamide or a pharmaceutically acceptable salt thereof.

30. The compound according to claim 1, N, ββ,3-Tetramethyl-L-phenylalanyl-$N^1$-{(1S,2E)-4-[(2S)-2-carboxypyrrolidin-1-yl]-1-isopropyl-3-methyl-4-oxobut-2-enyl}-$N^1$,3-dimethyl-L-valinamide or a pharmaceutically acceptable salt thereof.

31. The compound according to claim 1, 3-Chloro-N, ββ-trimethyl-L- phenylalanyl-$N^1$-{(1S,2E)-4-[(2S)-2-(methoxycarbonyl)pyrrolidin-1-yl]-1-isopropyl-3-methyl-4-oxobut-2-enyl}-$N^1$,3-dimethyl-L-valinamide or a pharmaceutically acceptable salt thereof.

32. The compound according to claim 1, 3-Chloro-N,ββ-trimethyl-L-phenylalanyl-N$^1$-{(1S,2E)-4-[(2S)-2-carboxypyrrolidin-1-yl]-1-isopropyl-3-methyl4-oxobut-2-enyl}-N$^1$,3-dimethyl-L-valinamide or a pharmaceutically acceptable salt thereof.

33. The compound according to claim 1, N, ββ-trimethyl-L-phenylalanyl-N$^1$-{(1S,2E)-1-isopropyl-4-[(2S)-2-((1R,2R)-1-methoxy-2-methyl-3-oxo-3{[(1S)-2phenyl-1-(1,3-thiazolyl-2-yl)ethyl]amino}propyl)pyrrolidin-1-yl]-3-methyl-4-oxobut-2-dimethyl-L-valinamide or a pharmaceutically acceptable salt thereof.

34. The compound according to claim 1, N, ββ-trimethyl-L-phenylalanyl-N$^1$-((1S,2E)-4-{(2S)-2-[(1R,2R)-1,3-dimethoxy-2-methyl-3-oxopropyl]pyrrolidin-1-yl}-1-isopropyl-3-methyl-4-oxobut-2-enyl)-N$^1$,3-dimethyl-L-valinamide or a pharmaceutically acceptable salt thereof.

35. The compound according to claim 1, N-methyl-3-phenyl-L-valyl-N$^1$-[(1S,2E)-1-isopropyl-4-((2S)-2-{(1R,2R)-1-methoxy-2-methyl-3-oxo-[(2-phenethyl)amino]propyl}pyrrolidin-1-yl)-3-methyl-4-oxobut-2-enyl]-N$^1$,3-dimethyl-L-valinamide or a pharmaceutically acceptable salt thereof.

36. The compound according to claim 1, N, ββ-trimethyl-L-phenylalanyl—N$^1$-{(1S,2E)-4-[(2S,4R)-2-(methoxycarbonyl)-4-hydroxypyrrolidin-1-yl]-1-isopropyl-3methyl-4oxobut-2-enyl}-N$^1$,3-dimethyl-L-valinamide or a pharmaceutically acceptable salt thereof.

37. The compound according to claim 1, N, β,β-trimethyl-L-phenylalanyl-N$^1$-{(1S,2E)-4-[(2R)-2-(methoxycarbonyl)pyrrolidin-1-yl]-1-isopropyl-3-methyl-4-oxobut-2-enyl}-N$^1$,3-dimethyl-L-valinamide or a pharmaceutically acceptable salt thereof.

38. The compound according to claim 1, N, β,β-trimethyl-L-phenylalanyl-N$^1$-{(1S,2E)-4-[(2S,4R)-2-carboxy4-hydroxypyrrolidin-1-yl]-1-isopropyl-3-methyl-4-oxobut-2-enyl}-N$^1$,3-dimethyl-L-valinamide or a pharmaceutically acceptable salt thereof.

39. The compound according to claim 1, N, β,β-trimethyl-L-phenylalanyl-N$^1$-{(1S,2E)-4-[(2R)-2-carboxypyrrolidin-1-yl]-1-isopropyl-3-methyl-4-oxobut-2-enyl}-N$^1$,3-dimethyl-L-valinamide or a pharmaceutically acceptable salt thereof.

40. The compound according to claim 1, 3-cyclohexyl-N-methyl-L-valyl-N$^1$-{(1S,2E)-1-isopropyl-4-[(2S)-2-((1R,2R)-1-methoxy-2-methyl-3-oxo-3-{[(1S)-2phenyl-1-(1,3-thiazol-2-yl)ethyl]aminol}propyl)pyrrolidin-1-yl]-3-methyl-4-oxobut-2-enyl}-N$^1$, 3-dimethyl-L-valinamide or a pharmaceutically acceptable salt thereof.

41. The compound according to claim 1, 3-cyclohexyl-N-methyl-L-valyl-N1-{(1 S,2E)-4-[(2S)-2-(methoxycarbonyl)pyrrolidin-1-yl]-1-isopropyl-3-methyl-4-oxobut enyl}—N1,3-dimethyl-L-valinamide or a pharmaceutically acceptable salt thereof.

42. The compound according to claim 1, 3-cyclohexyl—N-methyl-L-valyl-N$^1$-{(1S,2E)-4-[(2S)-2-carboxypyrrolidin-1-yl]-1-isopropyl-3-methyl-4-oxobut-2-enyl}-N$^1$,3-dimethyl-L-valinamide or a pharmaceutically acceptable salt thereof.

43. The compound according to claim 1, N,β,β-trimethyl-L-phenylalanyl-N$^1$-{(1 S,2E)-4-[(2S)-2-carboxy-2,5-dihydro-1H-pyrrol-1-yl]-1-isopropyl-3-methyl-4-oxobut-2-enyl}N$^1$,3-dimethyl-L-valinamide or a pharmaceutically acceptable salt thereof.

44. The compound according to claim 1, 3-cyclohexyl-N-methyl-L-valyl-N$^1$-[(1S,2E)-1-isopropyl-4-((2S)-2-{(1R,2R)-1 -methoxy-2-methyl-3-[(4R,5S)-4-methyl-2-oxo-5-phenyl-1,3-oxazolidin-3-yl]-3-oxopropyl}pyrrolidin-1-yl)-3-methyl-4-oxobut-2-enyl]-N$^1$,3-dimethyl-L-valinamide or a pharmaceutically acceptable salt thereof.

45. A pharmaceutical composition comprising an effective amount of a compound as claimed in claim 1 in combination with one or pharmaceutically acceptable carriers.

* * * * *

UNITED STATES PATENT AND TRADEMARK OFFICE
CERTIFICATE OF CORRECTION

PATENT NO. : 7,390,910 B2  Page 1 of 1
APPLICATION NO. : 10/911300
DATED : June 24, 2008
INVENTOR(S) : Zask et al.

It is certified that error appears in the above-identified patent and that said Letters Patent is hereby corrected as shown below:

Title Page Section (73) on the front page of the patent, delete "Wyeth" and insert --Wyeth Holdings Corporation-- in its place Column 107, line 4, insert the phrase --R9 is selected from--

Column 107, line 10, delete the phrase "R9 is selected from"

Column 107, line 14, remove the paragraph-break directly after "or"

Column 108, line 39, delete "R8" and insert --R6-- in its place

Signed and Sealed this

Fifth Day of May, 2009

JOHN DOLL
*Acting Director of the United States Patent and Trademark Office*